United States Patent
Lewis et al.

(10) Patent No.: US 11,142,522 B2
(45) Date of Patent: Oct. 12, 2021

(54) COMPOUNDS, COMPOSITIONS AND METHODS FOR CANCER TREATMENT

(71) Applicants: THE BROAD INSTITUTE, INC., Cambridge, MA (US); DANA-FARBER CANCER INSTITUTE, INC., Boston, MA (US); BAYER AKTIENGESELLSCHAFT, Leverkusen (DE); BAYER PHARMA AKTIENGESELLSCHAFT, Berlin (DE)

(72) Inventors: Timothy A. Lewis, Cambridge, MA (US); Xiaoyun Wu, Cambridge, MA (US); Heidi Greulich, Cambridge, MA (US); Matthew Meyerson, Boston, MA (US); Manuel Ellermann, Berlin (DE); Philip Lienau, Berlin (DE); Knut Eis, Berlin (DE); Antje Margret Wengner, Berlin (DE); Charlotte Christine Kopitz, Falkensee (DE); Martin Lange, Berlin (DE)

(73) Assignees: The Broad Institute, Inc., Cambridge, MA (US); Dana-Farber Cancer Institute, Inc., Boston, MA (US); Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/480,498

(22) PCT Filed: Feb. 1, 2018

(86) PCT No.: PCT/EP2018/052491
§ 371 (c)(1),
(2) Date: Jul. 24, 2019

(87) PCT Pub. No.: WO2018/141835
PCT Pub. Date: Aug. 9, 2018

(65) Prior Publication Data
US 2020/0062741 A1    Feb. 27, 2020

Related U.S. Application Data

(60) Provisional application No. 62/454,407, filed on Feb. 3, 2017.

(51) Int. Cl.
*C07D 413/10*   (2006.01)
*A61P 35/02*    (2006.01)

(52) U.S. Cl.
CPC ............ *C07D 413/10* (2013.01); *A61P 35/02* (2018.01)

(58) Field of Classification Search
CPC .................................................... C07D 413/10
See application file for complete search history.

(56) References Cited

FOREIGN PATENT DOCUMENTS

WO     2014164704 A2     10/2014
WO     2017134231 A1     8/2017

OTHER PUBLICATIONS

Lima, 2005, Current Medicinal Chemistry, vol. 12, p. 23-49.*
International Search Report and Written Opinion for corresponding PCT Patent Application No. PCT/EP2018/052491, dated Apr. 4, 2018 (8 pages).
Maurice et al., "Advances in targeting cyclic nucleotide phosphodiesterases," Nature Reviews: Drug Discovery, Apr. 2014, vol. 13, pp. 290-314.
Savai et al., "Targeting cancer with phosphodiesterase inhibitors," Expert Opinion on Investigational Drugs, 2010, vol. 19, Iss. 1, pp. 117-131.
Office Action issued in corresponding European Patent Application No. 18704189.2, dated Aug. 26, 2020 (5 pages).
U.S. Appl. No. 17/161,612, filed Jan. 28, 2021.

* cited by examiner

*Primary Examiner* — Rebecca L Anderson
(74) *Attorney, Agent, or Firm* — Melissa Hunter-Ensor; Scott Goncher; Greenberg Traurig, LLP

(57) ABSTRACT

The present invention features improved compounds, especially the compound having the structure (1). Compositions and methods of identifying patients having cancer using biomarkers (e.g., PDE3A, PDE3B, SLFN12 and/or CREB3L1) that correlate with drug sensitivity and consequently treating a stratified patient population with an agent of the invention.

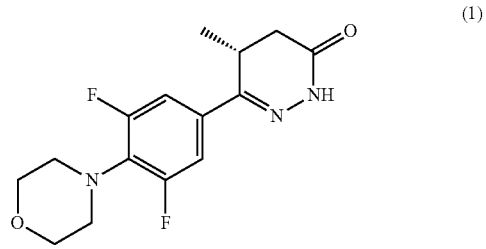

(1)

16 Claims, 4 Drawing Sheets
Specification includes a Sequence Listing.

SEQUENCE LISTING

<160> NUMBER OF SEQ ID NOS: 10

<210> SEQ ID NO 1
<211> LENGTH: 519
<212> TYPE: PRT
<213> ORGANISM: Homo sapiens
<220> FEATURE:
<223> OTHER INFORMATION: Lab host: DH10B-R

<400> SEQUENCE: 1

```
Met Asp Ala Val Leu Glu Pro Phe Pro Ala Asp Arg Leu Phe Pro Gly
1               5                   10                  15

Ser Ser Phe Leu Asp Leu Gly Asp Leu Asn Glu Ser Asp Phe Leu Asn
                20                  25                  30

Asn Ala His Phe Pro Glu His Leu Asp His Phe Thr Glu Asn Met Glu
            35                  40                  45

Asp Phe Ser Asn Asp Leu Phe Ser Ser Phe Phe Asp Asp Pro Val Leu
        50                  55                  60

Asp Glu Lys Ser Pro Leu Leu Asp Met Glu Leu Asp Ser Pro Thr Pro
65                  70                  75                  80

Gly Ile Gln Ala Glu His Ser Tyr Ser Leu Ser Gly Asp Ser Ala Pro
                85                  90                  95

Gln Ser Pro Leu Val Pro Ile Lys Met Glu Asp Thr Thr Gln Asp Ala
            100                 105                 110

Glu His Gly Ala Trp Ala Leu Gly His His Lys Leu Cys Ser Ile Met Val
        115                 120                 125

Lys Gln Glu Gln Ser Pro Glu Leu Pro Val Asp Pro Leu Ala Ala Pro
130                 135                 140

Ser Ala Met Ala Ala Ala Ala Met Ala Thr Thr Pro Leu Leu Gly
145                 150                 155                 160

Leu Ser Pro Leu Ser Arg Leu Pro Ile Pro His Gln Ala Pro Gly Glu
                165                 170                 175

Met Thr Gln Leu Pro Val Ile Lys Ala Glu Pro Leu Glu Val Asn Gln
            180                 185                 190

Phe Leu Lys Val Thr Pro Glu Asp Leu Val Gln Met Pro Pro Thr Pro
        195                 200                 205

Pro Ser His Gly Ser Asp Ser Asp Gly Ser Gln Ser Pro Arg Ser
    210                 215                 220

Leu Pro Pro Ser Ser Pro Val Arg Pro Met Ala Arg Ser Ser Thr Ala
225                 230                 235                 240

Ile Ser Thr Ser Pro Leu Leu Thr Pro Pro His Lys Leu Gln Gly Thr
                245                 250                 255

Ser Gly Pro Leu Leu Leu Thr Glu Glu Glu Lys Arg Thr Leu Ile Ala
            260                 265                 270

Glu Gly Tyr Pro Ile Pro Thr Lys Leu Pro Leu Thr Lys Ala Glu Glu
        275                 280                 285
```

Lys Ala Leu Lys Arg Val Arg Arg Lys Ile Lys Asn Lys Ile Ser Ala
            290                 295                 300

Gln Glu Ser Arg Arg Lys Lys Glu Tyr Val Glu Cys Leu Glu Lys
305                 310                 315                 320

Lys Val Glu Thr Phe Thr Ser Glu Asn Asn Glu Leu Trp Lys Lys Val
                325                 330                 335

Glu Thr Leu Glu Asn Ala Asn Arg Thr Leu Leu Gln Gln Leu Gln Lys
            340                 345                 350

Leu Gln Thr Leu Val Thr Asn Lys Ile Ser Arg Pro Tyr Lys Met Ala
            355                 360                 365

Ala Thr Gln Thr Gly Thr Cys Leu Met Val Ala Ala Leu Cys Phe Val
            370                 375                 380

Leu Val Leu Gly Ser Leu Val Pro Cys Leu Pro Glu Phe Ser Ser Gly
385                 390                 395                 400

Ser Gln Thr Val Lys Glu Asp Pro Leu Ala Ala Asp Gly Val Tyr Thr
                405                 410                 415

Ala Ser Gln Met Pro Ser Arg Ser Leu Leu Phe Tyr Asp Asp Gly Ala
            420                 425                 430

Gly Leu Trp Glu Asp Gly Arg Ser Thr Leu Leu Pro Met Glu Pro Pro
            435                 440                 445

Asp Gly Trp Glu Ile Asn Pro Gly Gly Pro Ala Glu Gln Arg Pro Arg
450                 455                 460

Asp His Leu Gln His Asp His Leu Asp Ser Thr His Glu Thr Thr Lys
465                 470                 475                 480

Tyr Leu Ser Glu Ala Trp Pro Lys Asp Gly Asn Gly Thr Ser Pro
                485                 490                 495

Asp Phe Ser His Ser Lys Glu Trp Phe His Asp Arg Asp Leu Gly Pro
            500                 505                 510

Asn Thr Thr Ile Lys Leu Ser
            515

<210> SEQ ID NO 2
<211> LENGTH: 2741
<212> TYPE: DNA
<213> ORGANISM: Homo sapiens
<220> FEATURE:
<223> OTHER INFORMATION: Lab host: DH10B-R

<400> SEQUENCE: 2
ccagccaggg gttcccggtt tcacagagag gaaagtgaca gaagacgtgc ggagggagac      60
gcagagacag aggagaggcc ggcagccacc cagtctcggg ggagcactta gctccccgc     120 cccggctccc accctgtccg gggggctcct gaagccctca gccccaaccc cgggctcccc    180
atggaagcca gctgtgcccc aggaggagca ggaggaggtg gagtcggctg aatgcccacg    240
gtgcgcccgg ggcccctgag cccatcccgc tcctagccgc tgccctaagg ccccgcgcg    300 cccgcgcccc ccacccgggg ccgcgccgc ctccgtccgc cctccccgg ggcttcgcc      360 ccggacctgc cccccgcccg tttgccagcg ctcaggcagg agctctggac tgggcgcgcc    420
gccgccctgg agtgagggaa gcccagtgga aggggtccc gggagccggc tgcgatggac     480
gccgtcttgg aacccttccc ggccgacagg ctgttccccg gatccagctt cctggacttg    540
ggggatctga cgagtcgga cttcctcaac aatgcgcact tcctgagca cctggaccac    600 tttacgaga catggagga cttctccaat gacctgttca gcagcttctt tgatgaccct    660
gtgctggatg agaagagccc tctattggac atggaactgg actcccctac gccaggcatc    720

-continued

```
caggcggagc acagctactc cctgagcggc gactcagcgc cccagagccc ccttgtgccc      780
atcaagatgg aggacaccac ccaagatgca gagcatggag catgggcgct gggacacaaa      840
ctgtgctcca tcatggtgaa gcaggagcag agcccggagc tgcccgtgga ccctctggct      900 gcccctcgg ccatggctgc cgcggccgcc atggccacca cccgctgct gggcctcagc       960 cccttgtcca ggctgcccat ccccaccag gccccgggag agatgactca gctgccagtg      1020
atcaaagcag agcctctgga ggtgaaccag ttcctcaaag tgacaccgga ggacctggtg     1080
cagatgcctc cgacgccccc cagcagccat ggcagtgaca gcgacggctc ccagagtccc     1140
cgctctctgc ccccctccag ccctgtcagg cccatggcgc gctcctccac ggccatctcc     1200
acctccccac tcctcactgc ccctcacaaa ttacagggga catcagggcc actgctcctg     1260
acagaggagg agaagcggac cctgattgct gagggctacc ccatccccac aaaactcccc     1320
ctcaccaaag ccgaggagaa ggccttgaag agagtccgga ggaaaatcaa gaacaagatc     1380
tcagcccagg agagccgtcg taagaagaag gagtatgtgg agtgtctaga aaagaaggtg     1440
gagacattta catctgagaa caatgaactg tggaagaagg tggagaccct ggagaatgcc     1500
aacaggaccc tgctccagca gctgcagaaa ctccagactc tggtcaccaa caagatctcc     1560
agaccttaca agatggccgc cacccagact gggacctgcc tcatggtggc agccttgtgc     1620
tttgttctgg tgctgggctc cctcgtgccc tgccttcccg agttctcctc cggctcccag     1680
actgtgaagg aagaccccct ggccgcagac ggcgtctaca cggccagcca gatgccctcc     1740
cgaagcctcc tattctacga tgacggggca ggcttatggg aagatggccg cagcaccctg     1800
ctgcccatgg agcccccaga tggctgggaa atcaacccccg gggggccggc agagcagcgg     1860
ccccgggacc acctgcagca tgatcacctg gacagcaccc acgagaccac caagtacctg     1920
agtgaggcct ggcctaaaga cggtggaaac ggcaccagcc ccgacttctc ccactccaag     1980
gagtggttcc acgacaggga tctgggcccc aacaccacca tcaaactctc ctaggccatg     2040
ccaagaccca ggacatagga cggacccctg gtacccagaa gaggagttct tgctcactaa     2100
cccggatccg cctcgtgccc ctgcctcctg gagcttccca ttccaggaga aaaggctcca     2160
cttcccagcc cttccttgcc cctgacattt ggactcttcc cttgggccga ccactctgtt     2220
ctcattctcc ttcccaccaa catccatccg tccttctcag acaaaccact cactgggtac     2280
cccacctcct ctctcatatg cccaaacacga ccactgcctc cctgccccca cacctgcacc     2340
caaacagaca catcaacgca ccccactcac agacacccct taccccaccc ccactgtaca     2400
gagaccaaga acagaaattg tttgtaaata atgaacctta ttttttatta ttgccaatcc     2460
cctaagatat tgtattttac aaatctcccct cttcccttcg cccctccctt gttttatatt     2520
ttatgaagtt agtgcgggct ttgctgctcc ctggcccagg aaagagggac tacctgaccc     2580
tcacctggca cccccctgct gctgcccaag ccgctgggcc ttttttaattg ccaaactgct     2640 ctcttcatca gctcagcaca tgctttaaga aagcaaaacc aaaaaaaaaa aaaaaagat      2700 gcagcatcaa aaaaaaaaaa aaaaaaaaa aaaaaaaaa a                           2741
```

<210> SEQ ID NO 3
<211> LENGTH: 1141
<212> TYPE: PRT
<213> ORGANISM: Homo sapiens
<220> FEATURE:
<223> OTHER INFORMATION: human full-length PDE3A amino acid sequence

<400> SEQUENCE: 3

```
Met Ala Val Pro Gly Asp Ala Ala Arg Val Arg Asp Lys Pro Val His
1               5                  10                  15

Ser Gly Val Ser Gln Ala Pro Thr Ala Gly Arg Asp Cys His His Arg
            20                  25                  30

Ala Asp Pro Ala Ser Pro Arg Asp Ser Gly Cys Arg Gly Cys Trp Gly
        35                  40                  45

Asp Leu Val Leu Gln Pro Leu Arg Ser Ser Arg Lys Leu Ser Ser Ala
    50                  55                  60

Leu Cys Ala Gly Ser Leu Ser Phe Leu Leu Ala Leu Leu Val Arg Leu
65                  70                  75                  80

Val Arg Gly Glu Val Gly Cys Asp Leu Glu Gln Cys Lys Glu Ala Ala
                85                  90                  95

Ala Ala Glu Glu Glu Glu Ala Ala Pro Gly Ala Glu Gly Gly Val Phe
            100                 105                 110

Pro Gly Pro Arg Gly Gly Ala Pro Gly Gly Ala Arg Leu Ser Pro
            115                 120                 125

Trp Leu Gln Pro Ser Ala Leu Leu Phe Ser Leu Leu Cys Ala Phe Phe
    130                 135                 140

Trp Met Gly Leu Tyr Leu Leu Arg Ala Gly Val Arg Leu Pro Leu Ala
145                 150                 155                 160

Val Ala Leu Leu Ala Ala Cys Cys Gly Gly Glu Ala Leu Val Gln Ile
                165                 170                 175

Gly Leu Gly Val Gly Glu Asp His Leu Leu Ser Leu Pro Ala Ala Gly
                180                 185                 190

Val Val Leu Ser Cys Leu Ala Ala Ala Thr Trp Leu Val Leu Arg Leu
            195                 200                 205

Arg Leu Gly Val Leu Met Ile Ala Leu Thr Ser Ala Val Arg Thr Val
    210                 215                 220

Ser Leu Ile Ser Leu Glu Arg Phe Lys Val Ala Trp Arg Pro Tyr Leu
225                 230                 235                 240

Ala Tyr Leu Ala Gly Val Leu Gly Ile Leu Leu Ala Arg Tyr Val Glu
                245                 250                 255

Gln Ile Leu Pro Gln Ser Ala Glu Ala Ala Pro Arg Glu His Leu Gly
                260                 265                 270

Ser Gln Leu Ile Ala Gly Thr Lys Glu Asp Ile Pro Val Phe Lys Arg
    275                 280                 285

Arg Arg Arg Ser Ser Ser Val Val Ser Ala Glu Met Ser Gly Cys Ser
        290                 295                 300

Ser Lys Ser His Arg Arg Thr Ser Leu Pro Cys Ile Pro Arg Glu Gln
305                 310                 315                 320

Leu Met Gly His Ser Glu Trp Asp His Lys Arg Gly Pro Arg Gly Ser
                325                 330                 335

Gln Ser Ser Gly Thr Ser Ile Thr Val Asp Ile Ala Val Met Gly Glu
            340                 345                 350

Ala His Gly Leu Ile Thr Asp Leu Leu Ala Asp Pro Ser Leu Pro Pro
        355                 360                 365

Asn Val Cys Thr Ser Leu Arg Ala Val Ser Asn Leu Leu Ser Thr Gln
    370                 375                 380

Leu Thr Phe Gln Ala Ile His Lys Pro Arg Val Asn Pro Val Thr Ser
385                 390                 395                 400

Leu Ser Glu Asn Tyr Thr Cys Ser Asp Ser Glu Glu Ser Ser Glu Lys
                405                 410                 415

Asp Lys Leu Ala Ile Pro Lys Arg Leu Arg Arg Ser Leu Pro Pro Gly
```

```
              420                 425                 430
Leu Leu Arg Arg Val Ser Ser Thr Trp Thr Thr Thr Ser Ala Thr
        435                 440                 445
Gly Leu Pro Thr Leu Glu Pro Ala Pro Val Arg Arg Asp Arg Ser Thr
    450                 455                 460
Ser Ile Lys Leu Gln Glu Ala Pro Ser Ser Ser Pro Asp Ser Trp Asn
465                 470                 475                 480
Asn Pro Val Met Met Thr Leu Thr Lys Ser Arg Ser Phe Thr Ser Ser
                485                 490                 495
Tyr Ala Ile Ser Ala Ala Asn His Val Lys Ala Lys Gln Ser Arg
            500                 505                 510
Pro Gly Ala Leu Ala Lys Ile Ser Pro Leu Ser Ser Pro Cys Ser Ser
        515                 520                 525
Pro Leu Gln Gly Thr Pro Ala Ser Ser Leu Val Ser Lys Ile Ser Ala
    530                 535                 540
Val Gln Phe Pro Glu Ser Ala Asp Thr Thr Ala Lys Gln Ser Leu Gly
545                 550                 555                 560
Ser His Arg Ala Leu Thr Tyr Thr Gln Ser Ala Pro Asp Leu Ser Pro
                565                 570                 575
Gln Ile Leu Thr Pro Pro Val Ile Cys Ser Ser Cys Gly Arg Pro Tyr
            580                 585                 590
Ser Gln Gly Asn Pro Ala Asp Glu Pro Leu Glu Arg Ser Gly Val Ala
        595                 600                 605
Thr Arg Thr Pro Ser Arg Thr Asp Asp Thr Ala Gln Val Thr Ser Asp
    610                 615                 620
Tyr Glu Thr Asn Asn Asn Ser Asp Ser Ser Asp Ile Val Gln Asn Glu
625                 630                 635                 640
Asp Glu Thr Glu Cys Leu Arg Glu Pro Leu Arg Lys Ala Ser Ala Cys
                645                 650                 655
Ser Thr Tyr Ala Pro Glu Thr Met Met Phe Leu Asp Lys Pro Ile Leu
            660                 665                 670
Ala Pro Glu Pro Leu Val Met Asp Asn Leu Asp Ser Ile Met Glu Gln
        675                 680                 685
Leu Asn Thr Trp Asn Phe Pro Ile Phe Asp Leu Val Glu Asn Ile Gly
    690                 695                 700
Arg Lys Cys Gly Arg Ile Leu Ser Gln Val Ser Tyr Arg Leu Phe Glu
705                 710                 715                 720
Asp Met Gly Leu Phe Glu Ala Phe Lys Ile Pro Ile Arg Glu Phe Met
                725                 730                 735
Asn Tyr Phe His Ala Leu Glu Ile Gly Tyr Arg Asp Ile Pro Tyr His
            740                 745                 750
Asn Arg Ile His Ala Thr Asp Val Leu His Ala Val Trp Tyr Leu Thr
        755                 760                 765
Thr Gln Pro Ile Pro Gly Leu Ser Thr Val Ile Asn Asp His Gly Ser
    770                 775                 780
Thr Ser Asp Ser Asp Ser Asp Ser Gly Phe Thr His Gly His Met Gly
785                 790                 795                 800
Tyr Val Phe Ser Lys Thr Tyr Asn Val Thr Asp Asp Lys Tyr Gly Cys
                805                 810                 815
Leu Ser Gly Asn Ile Pro Ala Leu Glu Leu Met Ala Leu Tyr Val Ala
            820                 825                 830
Ala Ala Met His Asp Tyr Asp His Pro Gly Arg Thr Asn Ala Phe Leu
        835                 840                 845
```

Val Ala Thr Ser Ala Pro Gln Ala Val Leu Tyr Asn Asp Arg Ser Val
    850                 855                 860

Leu Glu Asn His His Ala Ala Ala Trp Asn Leu Phe Met Ser Arg
865                 870                 875                 880

Pro Glu Tyr Asn Phe Leu Ile Asn Leu Asp His Val Glu Phe Lys His
                885                 890                 895

Phe Arg Phe Leu Val Ile Glu Ala Ile Leu Ala Thr Asp Leu Lys Lys
            900                 905                 910

His Phe Asp Phe Val Ala Lys Phe Asn Gly Lys Val Asn Asp Val
        915                 920                 925

Gly Ile Asp Trp Thr Asn Glu Asn Asp Arg Leu Leu Val Cys Gln Met
    930                 935                 940

Cys Ile Lys Leu Ala Asp Ile Asn Gly Pro Ala Lys Cys Lys Glu Leu
945                 950                 955                 960

His Leu Gln Trp Thr Asp Gly Ile Val Asn Glu Phe Tyr Glu Gln Gly
                965                 970                 975

Asp Glu Glu Ala Ser Leu Gly Leu Pro Ile Ser Pro Phe Met Asp Arg
            980                 985                 990

Ser Ala Pro Gln Leu Ala Asn Leu Gln Glu Ser Phe Ile Ser His Ile
        995                 1000                 1005

Val Gly Pro Leu Cys Asn Ser Tyr Asp Ser Ala Gly Leu Met Pro
    1010                1015                1020

Gly Lys Trp Val Glu Asp Ser Asp Glu Ser Gly Asp Thr Asp Asp
    1025                1030                1035

Pro Glu Glu Glu Glu Glu Ala Pro Ala Pro Asn Glu Glu Glu
    1040                1045                1050

Thr Cys Glu Asn Asn Glu Ser Pro Lys Lys Lys Thr Phe Lys Arg
    1055                1060                1065

Arg Lys Ile Tyr Cys Gln Ile Thr Gln His Leu Leu Gln Asn His
    1070                1075                1080

Lys Met Trp Lys Lys Val Ile Glu Glu Glu Gln Arg Leu Ala Gly
    1085                1090                1095

Ile Glu Asn Gln Ser Leu Asp Gln Thr Pro Gln Ser His Ser Ser
    1100                1105                1110

Glu Gln Ile Gln Ala Ile Lys Glu Glu Glu Glu Lys Gly Lys
    1115                1120                1125

Pro Arg Gly Glu Glu Ile Pro Thr Gln Lys Pro Asp Gln
    1130                1135                1140

<210> SEQ ID NO 4
<211> LENGTH: 7319
<212> TYPE: DNA
<213> ORGANISM: Homo sapiens
<220> FEATURE:
<223> OTHER INFORMATION: transcript variant 1

<400> SEQUENCE: 4
gggggccact gggaattcag tgaagagggc accctatacc atggcagtgc ccggcgacgc    60
tgcacgagtc agggacaagc ccgtccacag tggggtgagt caagccccca cggcgggccg   120
ggactgccac catcgtgcgg accccgcatc gccgcgggac tcgggctgcc gtggctgctg   180
gggagacctg gtgctgcagc cgctccggag ctctcggaaa ctttcctccg cgctgtgcgc   240
gggctccctg tcctttctgc tggcgctgct ggtgaggctg gtccgcgggg aggtcggctg   300
tgacctggag cagtgtaagg aggcggcggc ggcggaggag gaggaagcag ccccgggagc   360

```
agaaggggc gtcttcccgg ggcctcgggg aggtgctccc gggggcggtg cgcggctcag    420
cccctggctg cagccctcgg cgctgctctt cagtctcctg tgtgccttct tctggatggg    480
cttgtacctc ctgcgcgccg gggtgcgcct gcctctggct gtcgcgctgc tggccgcctg    540
ctgcgggggg gaagcgctcg tccagattgg gctgggcgtc ggggaggatc acttactctc    600
actccccgcc gcggggggtgg tgctcagctg cttggccgcc gcgacatggc tggtgctgag    660
gctgaggctg ggcgtcctca tgatcgcctt gactagcgcg gtcaggaccg tgtccctcat    720
ttccttagag aggttcaagg tcgcctggag accttacctg gcgtacctgg ccggcgtgct    780
ggggatcctc ttggccaggt acgtggaaca aatcttgccg cagtccgcgg aggcggctcc    840
aagggagcat ttggggtccc agctgattgc tgggaccaag aagatatcc cggtgtttaa    900 gaggaggagg cggtccagct ccgtcgtgtc cgccgagatg tccggctgca gcagcaagtc    960
ccatcggagg acctccctgc cctgtatacc gagggaacag ctcatggggc attcagaatg   1020
ggaccacaaa cgaggccaa gaggatcaca gtcttcagga accagtatta ctgtggacat   1080
cgccgtcatg ggcgaggccc acggcctcat taccgacctc ctggcagacc cttctcttcc   1140
accaaacgtg tgcacatcct tgagagccgt gagcaacttg ctcagcacac agctcacctt   1200
ccaggccatt cacaagccca gagtgaatcc cgtcacttcg ctcagtgaaa actataccctg   1260 ttctgactct gaagagagct ctgaaaaaga caagcttgct attccaaagc gcctgagaag   1320
gagtttgcct cctggcttgt tgagacgagt ttcttccact tggaccacca ccacctcggc   1380
cacaggtcta cccaccttgg agcctgcacc agtacggaga gaccgcagca ccagcatcaa   1440
actgcaggaa gcaccttcat ccagtcctga ttcttggaat aatccagtga tgatgaccct   1500
caccaaaagc agatccttta cttcatccta tgctatttct gcagctaacc atgtaaaggc   1560
taaaaagcaa agtcgaccag gtgccctcgc taaaatttca cctctttcat cgccctgctc   1620
ctcacctctc caagggactc ctgccagcag cctggtcagc aaaatttctg cagtgcagtt   1680
tccagaatct gctgacacaa ctgccaaaca aagcctaggt tctcacaggg ccttaactta   1740
cactcagagt gccccagacc tatccctca aatcctgact ccacctgtta tatgtagcag   1800
ctgtggcaga ccatattccc aagggaatcc tgctgatgag cccctggaga gaagtggggt   1860
agccactcgg acaccaagta gaacagatga cactgctcaa gttacctctg attatgaaac   1920
caataacaac agtgacagca gtgacattgt acagaatgaa gatgaaacag agtgcctgag   1980
agagcctctg aggaaagcat cggcttgcag cacctatgct cctgagacca tgatgtttct   2040
ggacaaacca attcttgctc ccgaacctct tgtcatggat aacctggact caattatgga   2100
gcagctaaat acttggaatt ttccaattt tgatttagtg gaaaatatag gaagaaatg   2160 tggccgtatt cttagtcagg tatcttacag acttttgaa gacatgggcc tctttgaagc   2220
ttttaaaatt ccaattaggg aatttatgaa ttatttcat gctttggaga ttggatatag   2280
ggatattcct tatcataaca gaatccatgc cactgatgtt ttacatgctg tttggtatct   2340
tactacacag cctattccag gcctctcaac tgtgattaat gatcatggtt caaccagtga   2400
ttcagattct gacagtggat ttacacatgg acatatggga tatgtattct caaaaacgta   2460
taatgtgaca gatgataaat acggatgtct gtctgggaat atccctgcct ggagttgat   2520 ggcgctgtat gtggctgcag ccatgcacga ttatgatcat ccaggaagga ctaatgcttt   2580
cctggttgca actagtgctc ctcaggcggt gctatataac gatcgttcag ttttggagaa   2640
tcatcacgca gctgctgcat ggaatctttt catgtcccgg ccagagtata acttcttaat   2700
```

```
taaccttgac catgtggaat ttaagcattt ccgtttcctt gtcattgaag caattttggc    2760
cactgacctg aagaaacact ttgacttcgt agccaaattt aatggcaagg taaatgatga    2820
tgttggaata gattggacca atgaaaatga tcgtctactg gtttgtcaaa tgtgtataaa    2880
gttggctgat atcaatggtc cagctaaatg taaagaactc catcttcagt ggacagatgg    2940
tattgtcaat gaattttatg aacagggtga tgaagaggcc agccttggat tacccataag    3000 cccttcatg gatcgttctg ctcctcagct ggccaacctt caggaatcct tcatctctca     3060
cattgtgggg cctctgtgca actcctatga ttcagcagga ctaatgcctg aaaatgggt     3120 ggaagacagc gatgagtcag gagatactga tgacccagaa gagaggagg aagaagcacc     3180 agcaccaaat gaagaggaaa cctgtgaaaa taatgaatct ccaaaaaaga gactttcaa     3240 aaggagaaaa atctactgcc aaataactca gcacctctta cagaaccaca agatgtggaa    3300
gaaagtcatt gaagaggagc aacggttggc aggcatagaa atcaatccc tggaccagac     3360 ccctcagtcg cactcttcag aacagatcca ggctatcaag gaagaagaag aagagaaagg    3420
gaaaccaaga ggcgaggaga taccaaccca aaagccagac cagtgacaat ggatagaatg    3480
ggctgtgttt ccaaacagat tgacttgtca aagactctct tcaagccagc acaacattta    3540
gacacaacac tgtagaaatt tgagatgggc aaatggctat tgcattttgg gattcttcgc    3600 atttgtgtg tatattttta cagtgaggta cattgttaaa aacttttgc tcaaagaagc      3660 tttcacattg caacaccagc ttctaaggat ttttaagga gggaatatat atgtgtgtgt     3720
gtatataagc tcccacatag atacatgtaa aacatattca cacccatgca cgcacacaca    3780
tacacactga aggccacgat tgctggctcc acaatttagt aacatttata ttaagatata    3840
tatatagtgg tcactgtgat ataataaatc ataaggaaa ccaaatcaca aaggagatgg     3900
tgtggcttag caaggaaaca gtgcaggaaa tgtaggttac caactaagca gcttttgctc    3960
ttagtactga gggatgaaag ttccagagca ttatttgaat tctgatacat cctgccaaca    4020
ctgtgtgtgt gtgtgtgtgt gtgtgtgtgt gtgtgtgtgt gtgtgaaaga gagacagaag    4080
ggaatggttt gagagggtgc ttgtgtgcat gtgtgtgcat atgtaaagag attttttgtgg   4140 tttaagtaac tcagaatagc tgtagcaaat gactgaatac atgtgaacaa acagaaggaa    4200
gttcactctg gagtgtcttt gggaggcagc cattccaaat gccctcctcc atttagcttc    4260
aataaagggc ctttttgctga tggagggcac tcaagggctg ggtgagaggg ccacgtgttt    4320
ggtattacat tactgctatg caccacttga aggagctcta tcaccagcct caaacccgaa    4380
agactgaggc attttccagt ctacttgcct aatgaatgta taggaactgt ctatgagtat    4440
ggatgtcact caactaagat caaatcacca tttaagggga tggcattctt tatacctaaa    4500
cacctaagag ctgaagtcag gtctttttaat caggttagaa ttctaaatga tgccagagaa    4560
ggcttgggaa attgtacttc agcgtgatag cctgtgtctt cttaatttgc tgcaaaatat    4620
gtggtagaga aagaaaagga aacagaaaaa tcactctggg ttatatagca agagatgaag    4680
gagaatattt caacacaggg ttttgtgtt gacataggaa aagcctgatt cttggcaact     4740
gttgtagttt gtcttttcagg ggtgaaggtc ccactgacaa cccctgttgt ggtgttccac    4800
acgctgtttg ttggggtagc ttccatcggc agtctggccc attgtcagtc atgcttcttc    4860
tggccgggga gattatagag agattgtttg aagattgggt tattattgaa agtctttttt    4920 tttgttttgtt ttgttttggt ttgtttgttt atctacactt gtttatgctg tgagccaaac   4980
ctctatttaa aaagttgata ctcactttca atattttatt tcatattatt atatatgtca    5040
tgatagttat cttgatgtaa atatgaagat tttttttgttt ctgtagatag taaactcttt   5100
```

```
ttttaaaaaa ggaaaaggga aacatttttta taaagttata tttttaatcac catttttata    5160 cattgtagtt ctctccaagc ccagtaagag aatgatgatt catttgcatg gaggtcgatg    5220
gacaaccaat catctacctt ttctaattta aatgataatc tgatatagtt ttattgccag    5280
ttaaatgagg atgctgcaaa gcatgttttt tcactagtaa cttttgctaa ctgaatgaat    5340
tctgggtcca tatctcccag atgaaaaact gttaaccaat accatatttt atagttggtg    5400
tccatttctt tccaacactg tttgttatga ttcttccttg agtacttata tacagacctg    5460
ctcattatct aaacaatctt accttctaag taaaccttga ttgtgatttc cagtttttat    5520
tttctctgac gtagtagaaa ggaatgttta cattaaaaat acttttgttt ctcataaatg    5580
gatattgtac tccccccttt caaagcatta ttttacaata attcatggca ttttaaaaaa    5640
taaggcaaag ataatacgac aaaaaatata catggtttca aggcaaattc tccaataagt    5700
tggaaaatgt aaaaaggatc aagtggatgc agcctctacc taaataatta aaatatattt    5760
cagtatattt ctgaattaac accaggtctt cattatttag aacttactaa attgttttca    5820
ttttcttagt tttacctgtg tatctccatg tttgcaaaaa ttactataag tcaaattttg    5880
ccagtgaatt taactatttt tcttttccttg caattaaggg gaaaaaagca tttatcttat    5940
cttctcatac cccttgcatc taagtactta gcaaagtcaa tatttttccca ttttccaaat    6000 gcgtccatct ctaacataaa tattaattga acatagagct atgtttggag tgagtggact    6060
ggcaggacag ttggaagtcc atcacagtct attgacagtt tcatcaaagc tgtatagtcc    6120
aactagtggg gcagcttggc tactatggtg gaagtctcag caaactgcct ggttttgttt    6180
gtttgttttg ttttaaggta caggaaataa gaggaataat agtggccaaa gcaattagaa    6240
catcttcatt ccagaactgt gttcagcaat ccaggcagat tgatacattt ttctttaaaa    6300
ataaattgct attacagcta gacgtcaatt gggataaata aagggatgaa gatccactaa    6360
gtttgtgact ttcatacaca cccagtacat ctcaaaggat gctaagggac attttctgcc    6420
agtagagttc tccccctttt tggtgacagc aatattatta tgttcacatc taactccaga    6480
gcttacttcc tgtggtgcca atgtatttgt tgcaatttac tacattttta tatgagccta    6540
tttataggtg ccattaaact caggtctttc aaatgaaaga gtttctagcc cacttaggga    6600
aaaagataat tgtttagaaa accataaaat caatggtagg aaaagttgga actggttacc    6660
tggatgccat ggttctctgt taaataaagt aagagaccag gtgtattctg agtgtcatca    6720
gtgttatttt cagcatgcta ataaatgtct ttccggttat atatctatct aaattaacct    6780
ttaaaatatt ggtttccttg ataaaagcac cacttttgct tttgttagct gtaatatttt    6840
ttgtcattta gataagacct ggtttggctc tcaataaaag atgaagacag tagctctgta    6900
cagggatata tctatattag tcttcatctg atgaatgaag aaattttctc atattatgtt    6960
caagaaagta tttacttcct aaaaatagaa ttcccgattc tgtctatttt ggttgaatac    7020
cagaacaaat cttccgttg caatcccagt aaaacgaaag aaaaggaata tcttacagac    7080
tgttcatatt agatgtatgt agactgttaa tttgcaattt ccccatattt cctgcctatc    7140
ttacccagat aactttcttt gaaggtaaaa gctgtgcaaa aggcatgaga ctcaggccta    7200
ctctttgttt aaatgatgga aaaatataaa ttattttcta agtaataaaa gtataaaaat    7260
tatcattata aataaagtct aaagtttgaa attattaatt taaaaaaaaa aaaaaaaaa    7319

<210> SEQ ID NO 5
<211> LENGTH: 578
<212> TYPE: PRT
```

<213> ORGANISM: Homo sapiens

<400> SEQUENCE: 5

```
Met Asn Ile Ser Val Asp Leu Glu Thr Asn Tyr Ala Glu Leu Val Leu
1               5                   10                  15

Asp Val Gly Arg Val Thr Leu Gly Glu Asn Ser Arg Lys Lys Met Lys
            20                  25                  30

Asp Cys Lys Leu Arg Lys Lys Gln Asn Glu Ser Val Ser Arg Ala Met
        35                  40                  45

Cys Ala Leu Leu Asn Ser Gly Gly Val Ile Lys Ala Glu Ile Glu
    50                  55                  60

Asn Glu Asp Tyr Ser Tyr Thr Lys Asp Gly Ile Gly Leu Asp Leu Glu
65                  70                  75                  80

Asn Ser Phe Ser Asn Ile Leu Leu Phe Val Pro Glu Tyr Leu Asp Phe
                85                  90                  95

Met Gln Asn Gly Asn Tyr Phe Leu Ile Phe Val Lys Ser Trp Ser Leu
            100                 105                 110

Asn Thr Ser Gly Leu Arg Ile Thr Thr Leu Ser Ser Asn Leu Tyr Lys
        115                 120                 125

Arg Asp Ile Thr Ser Ala Lys Val Met Asn Ala Thr Ala Ala Leu Glu
130                 135                 140

Phe Leu Lys Asp Met Lys Lys Thr Arg Gly Arg Leu Tyr Leu Arg Pro
145                 150                 155                 160

Glu Leu Leu Ala Lys Arg Pro Cys Val Asp Ile Gln Glu Gly Asn Asn
                165                 170                 175

Met Lys Ala Leu Ala Gly Val Phe Phe Asp Arg Thr Glu Leu Asp Arg
            180                 185                 190

Lys Glu Lys Leu Thr Phe Thr Glu Ser Thr His Val Glu Ile Lys Asn
        195                 200                 205

Phe Ser Thr Glu Lys Leu Leu Gln Arg Ile Lys Glu Ile Leu Pro Gln
210                 215                 220

Tyr Val Ser Ala Phe Ala Asn Thr Asp Gly Gly Tyr Leu Phe Ile Gly
225                 230                 235                 240

Leu Asn Glu Asp Lys Glu Ile Ile Gly Phe Lys Ala Glu Met Ser Asp
                245                 250                 255

Leu Asp Asp Leu Glu Arg Glu Ile Glu Lys Ser Ile Arg Lys Met Pro
            260                 265                 270

Val His His Phe Cys Met Glu Lys Lys Ile Asn Tyr Ser Cys Lys
        275                 280                 285

Phe Leu Gly Val Tyr Asp Lys Gly Ser Leu Cys Gly Tyr Val Cys Ala
290                 295                 300

Leu Arg Val Glu Arg Phe Cys Cys Ala Val Phe Ala Lys Glu Pro Asp
305                 310                 315                 320

Ser Trp His Val Lys Asp Asn Arg Val Met Gln Leu Thr Arg Lys Glu
                325                 330                 335

Trp Ile Gln Phe Met Val Glu Ala Glu Pro Lys Phe Ser Ser Ser Tyr
            340                 345                 350

Glu Glu Val Ile Ser Gln Ile Asn Thr Ser Leu Pro Ala Pro His Ser
        355                 360                 365

Trp Pro Leu Leu Glu Trp Gln Arg Gln Arg His His Cys Pro Gly Leu
370                 375                 380

Ser Gly Arg Ile Thr Tyr Thr Pro Glu Asn Leu Cys Arg Lys Leu Phe
385                 390                 395                 400
```

```
Leu Gln His Glu Gly Leu Lys Gln Leu Ile Cys Glu Glu Met Asp Ser
                405                 410                 415

Val Arg Lys Gly Ser Leu Ile Phe Ser Arg Ser Trp Ser Val Asp Leu
            420                 425                 430

Gly Leu Gln Glu Asn His Lys Val Leu Cys Asp Ala Leu Leu Ile Ser
        435                 440                 445

Gln Asp Ser Pro Pro Val Leu Tyr Thr Phe His Met Val Gln Asp Glu
    450                 455                 460

Glu Phe Lys Gly Tyr Ser Thr Gln Thr Ala Leu Thr Leu Lys Gln Lys
465                 470                 475                 480

Leu Ala Lys Ile Gly Gly Tyr Thr Lys Lys Val Cys Val Met Thr Lys
            485                 490                 495

Ile Phe Tyr Leu Ser Pro Glu Gly Met Thr Ser Cys Gln Tyr Asp Leu
        500                 505                 510

Arg Ser Gln Val Ile Tyr Pro Glu Ser Tyr Tyr Phe Thr Arg Arg Lys
    515                 520                 525

Tyr Leu Leu Lys Ala Leu Phe Lys Ala Leu Lys Arg Leu Lys Ser Leu
    530                 535                 540

Arg Asp Gln Phe Ser Phe Ala Glu Asn Leu Tyr Gln Ile Ile Gly Ile
545                 550                 555                 560

Asp Cys Phe Gln Lys Asn Asp Lys Lys Met Phe Lys Ser Cys Arg Arg
                565                 570                 575

Leu Thr

<210> SEQ ID NO 6
<211> LENGTH: 2530
<212> TYPE: DNA
<213> ORGANISM: Homo sapiens
<220> FEATURE:
<223> OTHER INFORMATION: transcript variant 1

<400> SEQUENCE: 6
tttgtaactt cacttcagcc tcccattgat cgctttctgc aaccattcag actgatctcg      60
ggctcctatt tcatttacat tgtgtgcaca ccaagtaacc agtgggaaaa ctttagaggg     120
tacttaaacc ccagaaaatt ctgaaaccgg gctcttgagc cgctatcctc gggcctgctc     180
ccaccctgtg gagtgcactt tcgttttcaa taaatctctg cttttgttgc ttcattcttt     240
ccttgctttg tttgtgtgtt tgtccagttc tttgttcaac acgccaagaa cctggacact     300
cttcactggt aacatatttt ggcaagccaa ccaggagaaa agaatttctg cttggacact     360
gcatagctgc tgggaaaatg aacatcagtg ttgatttgga aacgaattat gccgagttgg     420
ttctagatgt gggaagagtc actcttggag agaacagtag gaaaaaaatg aaggattgta     480
aactgagaaa aaagcagaat gaaagtgtct cacgagctat gtgtgctctg ctcaattctg     540 gaggggagt gatcaaggct gaaattgaga atgaagacta tagttataca aagatggaa      600 taggactaga tttggaaaat tcttttagta acattctgtt attgttcct gagtacttag      660 acttcatgca gaatggtaac tactttctga ttttgtgaa gtcatggagc ttgaacacct      720
ctggtctgcg gattaccacc ttgagctcca atttgtacaa agagatata acatctgcaa      780 aagtcatgaa tgccactgct gcactggagt tcctcaaaga catgaaaaag actagaggga      840
gattgtattt aagaccagaa ttgctggcaa agaggccctg tgttgatata caagaagaaa      900
ataacatgaa ggccttggcc gggggttttt ttgatagaac agaacttgat cggaaagaaa      960
aattgacctt tactgaatcc acacatgttg aaattaaaaa cttctcgaca gaaaagttgt     1020
```

```
tacaacgaat taaagagatt ctccctcaat atgtttctgc atttgcaaat actgatggag      1080
gatatttgtt cattggttta aatgaagata aagaaataat tggctttaaa gcagagatga      1140
gtgacctcga tgacttagaa agagaaatcg aaaagtccat taggaagatg cctgtgcatc      1200
acttctgtat ggagaagaag aagataaatt attcatgcaa attccttgga gtatatgata      1260
aaggaagtct tgtggatat gtctgtgcac tcagagtgga gcgcttctgc tgtgcagtgt       1320
ttgctaaaga gcctgattcc tggcatgtga agataaccg tgtgatgcag ttgaccagga       1380
aggaatggat ccagttcatg gtggaggctg aaccaaaatt ttccagttca tatgaagagg      1440
tgatctctca aataaatacg tcattacctg ctcccccacag ttggcctctt ttggaatggc     1500
aacggcagag acatcactgt ccagggctat caggaaggat aacgtatact ccagaaaacc      1560
tttgcagaaa actgttctta caacatgaag gacttaagca attaatatgt gaagaaatgg      1620
actctgtcag aaagggctca ctgatcttct ctaggagctg gtctgtggat ctgggcttgc      1680
aagagaacca caaagtcctc tgtgatgctc ttctgatttc ccaggacagt cctccagtcc      1740
tatacacctt ccacatggta caggatgagg agtttaaagg ctattctaca caaactgccc      1800
taaccttaaa gcagaagctg gcaaaaattg gtggttacac taaaaaagtg tgtgtcatga      1860
caaagatctt ctacttgagc cctgaaggca tgacaagctg ccagtatgat ttaaggtcgc      1920
aagtaattta ccctgaatcc tactatttta caagaaggaa atacttgctg aaagcccttt      1980
ttaaagcctt aaagagactc aagtctctga gagaccagtt ttcctttgca gaaaatctat      2040
accagataat cggtatagat tgctttcaga agaatgataa aaagatgttt aaatcttgtc      2100
gaaggctcac ctgatggaaa atggactggg ctactgagat atttttcatt atatatttga      2160
taacattctc taattctgtg aaaatatttc tttgaaaact ttgcaagtta agcaacttaa      2220
tgtgatgttg gataattggg ttttgtctat tttcacttct ccctaaataa tcttcacaga      2280
tattgtttga gggatattag gaaaattaat ttgttaactc gtctgtgcac agtattattt      2340
actctgtctg tagttcctga ataaattttc ttccatgctt gaactgggaa aattgcaaca      2400
cttttattct taatgacaac agtgaaaatc tcccagcata tacctagaaa acaattataa      2460
cttacaaaag attatccttg atgaaactca gaatttccac agtgggaatg aataagaagg      2520
caaaactcat                                                             2530

<210> SEQ ID NO 7
<211> LENGTH: 3339
<212> TYPE: DNA
<213> ORGANISM: Homo sapiens

<400> SEQUENCE: 7
atgaggaggg acgagcgaga cgccaaagcc atgcggtccc tgcagccgcc ggatggggcc       60
ggctcgcccc ccgagagtct gaggaacggc tacgtgaaga gctgcgtgag ccccttgcgg      120
caggaccctc cgcgcggctt cttcttccac ctctgccgct tctgcaacgt ggagctgcgg      180
ccgccgccgg cctctcccca gcagccgcgg cgctgctccc ccttctgccg ggcgcgcctc      240
tcgctgggcg ccctggctgc ctttgtcctc gccctgctgc tgggcgcgga acccgagagc      300
tgggctgccg gggccgcctg gctgcggacg ctgctgagcg tgtgttcgca cagcttgagc      360
cccctcttca gcatcgccct gccttcttc ttcctcacct gcttcctcac ccggaccaag      420 cggggaccccg gccgggccg gagctgcggc tcctggtggc tgctggcgct gcccgcctgc      480
tgttacctgg gggacttctt ggtgtggcag tggtggtctt ggccttgggg ggatggcgac      540
gcagggtccg cggccccgca cacgccccg gaggcggcag cgggcaggtt gctgctggtg      600
```

```
ctgagctgcg tagggctgct gctgacgctc gcgcacccgc tgcggctccg gcactgcgtt    660
ctggtgctgc tcctggccag cttcgtctgg tgggtctcct tcaccagcct cgggtcgctg    720
ccctccgccc tcaggccgct gctctccggc ctggtggggg gcgctggctg cctgctggcc    780
ctggggttgg atcacttctt tcaaatcagg gaagcgcctc ttcatcctcg actgtccagt    840 gccgccaag aaaaagtgcc tgtgatccga ccccggagga ggtccagctg cgtgtcgtta    900
ggagaaactg cagccagtta ctatggcagt tgcaaaatat tcaggagacc gtcgttgcct    960
tgtatttcca gagaacagat gattctttgg gattgggact taaaacaatg gtataagcct   1020
cattatcaaa attctggagg tgaaatgga gttgatcttt cagtgctaaa tgaggctcgc   1080
aatatggtgt cagatcttct gactgatcca agccttccac cacaagtcat ttcctctcta   1140
cggagtatta gtagcttaat gggtgctttc tcaggttcct gtaggccaaa gattaatcct   1200
ctcacaccat ttcctggatt ttaccccttgt tctgaaatag aggacccagc tgagaaaggg   1260
gatagaaaac ttaacaaggg actaaatagg aatagtttgc caactccaca gctgaggaga   1320
agctcaggaa cttcaggatt gctacctgtt gaacagtctt caaggtggga tcgtaataat   1380
ggcaaaagac ctcaccaaga atttggcatt tcaagtcaag gatgctatct aaatgggcct   1440
tttaattcaa atctactgac tatcccgaag caaaggtcat cttctgtatc actgactcac   1500
catgtaggtc tcagaagagc tggtgttttg tccagtctga gtcctgtgaa ttcttccaac   1560
catggaccag tgtctactgg ctctctaact aatcgatcac ccatagaatt tcctgatact   1620
gctgattttc ttaataagcc aagcgttatc ttgcagagat ctctgggcaa tgcacctaat   1680
actccagatt tttatcagca acttagaaat tctgatagca atctgtgtaa cagctgtgga   1740
catcaaatgc tgaaatatgt ttcaacatct gaatcagatg gtacagattg ctgcagtgga   1800
aaatcaggtg aagaagaaaa catttttctcg aaagaatcat tcaaacttat ggaaactcaa   1860
caagaagagg aaacagagaa gaaagacagc agaaaattat ttcaggaagg tgataagtgg   1920
ctaacagaag aggcacagag tgaacagcaa acaaatattg aacaggaagt atcactggac   1980
ctgattttag tagaagagta tgactcatta atagaaaaga tgagcaactg gaattttcca   2040 attttttgaac ttgtagaaaa gatgggagag aaatcaggaa ggattctcag tcaggttatg   2100 tatacctttat ttcaagacac tggtttattg gaaatatttta aaattcccac tcaacaattt   2160
atgaactatt ttcgtgcatt agaaaatggc tatcgagaca ttccttatca caatcgtata   2220
catgccacag atgtgctaca tgcagtttgg tatctgacaa cacggccagt tcctggctta   2280
cagcagatcc acaatggttg tggaacagga atgaaacag attctgatgg tagaattaac   2340
catgggcgaa ttgcttatat ttcttcgaag agctgctcta atcctgatga gagttatggc   2400
tgcctgtctt caaacattcc tgcattagaa ttgatggctc tatacgtggc agctgccatg   2460
catgattatg atcacccagg gaggacaaat gcatttctag tggctacaaa tgcccctcag   2520
gcagttttat acaatgacag atctgttctg gaaaatcatc atgctgcgtc agcttggaat   2580
ctatatcttt ctcgcccaga atacaacttc cttcttcatc ttgatcatgt ggaattcaag   2640
cgctttcgtt ttttagtcat tgaagcaatc cttgctacgg atcttaaaaa gcattttgat   2700
tttctcgcag aattcaatgc caaggcaaat gatgtaaata gtaatggcat agaatggagt   2760
aatgaaaatg atcgcctctt ggtatgccag gtgtgcatca aactggcaga tataaatggc   2820
ccagcaaaag ttcgagactt gcatttgaaa tggacagaag gcattgtcaa tgaattttat   2880
gagcagggag atgaagaagc aaatcttggt ctgcccatca gtccattcat ggatcgttct   2940
```

-continued

```
tctcctcaac tagcaaaact ccaagaatct tttatcaccc acatagtggg tcccctgtgt    3000
aactcctatg atgctgctgg tttgctacca ggtcagtggt tagaagcaga agaggataat    3060
gatactgaaa gtggtgatga tgaagacggt gaagaattag atacagaaga tgaagaaatg    3120
gaaaacaatc taaatccaaa accaccaaga aggaaaagca gacggcgaat attttgtcag    3180
ctaatgcacc acctcactga aaaccacaag atatggaagg aaatcgtaga ggaagaagaa    3240
aaatgtaaag ctgatgggaa taaactgcag gtggagaatt cctccttacc tcaagcagat    3300
gagattcagg taattgaaga ggcagatgaa gaggaatag                           3339
```

<210> SEQ ID NO 8
<211> LENGTH: 1112
<212> TYPE: PRT
<213> ORGANISM: Homo sapiens

<400> SEQUENCE: 8

```
Met Arg Arg Asp Glu Arg Asp Ala Lys Ala Met Arg Ser Leu Gln Pro
1               5                   10                  15

Pro Asp Gly Ala Gly Ser Pro Glu Ser Leu Arg Asn Gly Tyr Val
                20                  25                  30

Lys Ser Cys Val Ser Pro Leu Arg Gln Asp Pro Pro Arg Gly Phe Phe
            35                  40                  45

Phe His Leu Cys Arg Phe Cys Asn Val Glu Leu Arg Pro Pro Ala
    50                  55                  60

Ser Pro Gln Gln Pro Arg Arg Cys Ser Pro Phe Cys Arg Ala Arg Leu
65                  70                  75                  80

Ser Leu Gly Ala Leu Ala Ala Phe Val Leu Ala Leu Leu Leu Gly Ala
                85                  90                  95

Glu Pro Glu Ser Trp Ala Ala Gly Ala Ala Trp Leu Arg Thr Leu Leu
            100                 105                 110

Ser Val Cys Ser His Ser Leu Ser Pro Leu Phe Ser Ile Ala Cys Ala
        115                 120                 125

Phe Phe Phe Leu Thr Cys Phe Leu Thr Arg Thr Lys Arg Gly Pro Gly
    130                 135                 140

Pro Gly Arg Ser Cys Gly Ser Trp Trp Leu Leu Ala Leu Pro Ala Cys
145                 150                 155                 160

Cys Tyr Leu Gly Asp Phe Leu Val Trp Gln Trp Trp Ser Trp Pro Trp
                165                 170                 175

Gly Asp Gly Asp Ala Gly Ser Ala Ala Pro His Thr Pro Pro Glu Ala
            180                 185                 190

Ala Ala Gly Arg Leu Leu Leu Val Leu Ser Cys Val Gly Leu Leu Leu
        195                 200                 205

Thr Leu Ala His Pro Leu Arg Leu Arg His Cys Val Leu Val Leu Leu
    210                 215                 220

Leu Ala Ser Phe Val Trp Trp Val Ser Phe Thr Ser Leu Gly Ser Leu
225                 230                 235                 240

Pro Ser Ala Leu Arg Pro Leu Leu Ser Gly Leu Val Gly Gly Ala Gly
                245                 250                 255

Cys Leu Leu Ala Leu Gly Leu Asp His Phe Phe Gln Ile Arg Glu Ala
            260                 265                 270

Pro Leu His Pro Arg Leu Ser Ser Ala Ala Glu Glu Lys Val Pro Val
        275                 280                 285

Ile Arg Pro Arg Arg Arg Ser Ser Cys Val Ser Leu Gly Glu Thr Ala
    290                 295                 300
```

```
Ala Ser Tyr Tyr Gly Ser Cys Lys Ile Phe Arg Arg Pro Ser Leu Pro
305                 310                 315                 320

Cys Ile Ser Arg Glu Gln Met Ile Leu Trp Asp Trp Asp Leu Lys Gln
                325                 330                 335

Trp Tyr Lys Pro His Tyr Gln Asn Ser Gly Gly Gly Asn Gly Val Asp
            340                 345                 350

Leu Ser Val Leu Asn Glu Ala Arg Asn Met Val Ser Asp Leu Leu Thr
        355                 360                 365

Asp Pro Ser Leu Pro Pro Gln Val Ile Ser Ser Leu Arg Ser Ile Ser
    370                 375                 380

Ser Leu Met Gly Ala Phe Ser Gly Ser Cys Arg Pro Lys Ile Asn Pro
385                 390                 395                 400

Leu Thr Pro Phe Pro Gly Phe Tyr Pro Cys Ser Glu Ile Glu Asp Pro
                405                 410                 415

Ala Glu Lys Gly Asp Arg Lys Leu Asn Lys Gly Leu Asn Arg Asn Ser
            420                 425                 430

Leu Pro Thr Pro Gln Leu Arg Arg Ser Ser Gly Thr Ser Gly Leu Leu
        435                 440                 445

Pro Val Glu Gln Ser Ser Arg Trp Asp Arg Asn Asn Gly Lys Arg Pro
    450                 455                 460

His Gln Glu Phe Gly Ile Ser Ser Gln Gly Cys Tyr Leu Asn Gly Pro
465                 470                 475                 480

Phe Asn Ser Asn Leu Leu Thr Ile Pro Lys Gln Arg Ser Ser Ser Val
                485                 490                 495

Ser Leu Thr His His Val Gly Leu Arg Arg Ala Gly Val Leu Ser Ser
            500                 505                 510

Leu Ser Pro Val Asn Ser Ser Asn His Gly Pro Val Ser Thr Gly Ser
        515                 520                 525

Leu Thr Asn Arg Ser Pro Ile Glu Phe Pro Asp Thr Ala Asp Phe Leu
    530                 535                 540

Asn Lys Pro Ser Val Ile Leu Gln Arg Ser Leu Gly Asn Ala Pro Asn
545                 550                 555                 560

Thr Pro Asp Phe Tyr Gln Gln Leu Arg Asn Ser Asp Ser Asn Leu Cys
                565                 570                 575

Asn Ser Cys Gly His Gln Met Leu Lys Tyr Val Ser Thr Ser Glu Ser
            580                 585                 590

Asp Gly Thr Asp Cys Cys Ser Gly Lys Ser Gly Glu Glu Glu Asn Ile
        595                 600                 605

Phe Ser Lys Glu Ser Phe Lys Leu Met Glu Thr Gln Gln Glu Glu Glu
    610                 615                 620

Thr Glu Lys Lys Asp Ser Arg Lys Leu Phe Gln Glu Gly Asp Lys Trp
625                 630                 635                 640

Leu Thr Glu Glu Ala Gln Ser Glu Gln Gln Thr Asn Ile Glu Gln Glu
                645                 650                 655

Val Ser Leu Asp Leu Ile Leu Val Glu Glu Tyr Asp Ser Leu Ile Glu
            660                 665                 670

Lys Met Ser Asn Trp Asn Phe Pro Ile Phe Glu Leu Val Glu Lys Met
        675                 680                 685

Gly Glu Lys Ser Gly Arg Ile Leu Ser Gln Val Met Tyr Thr Leu Phe
    690                 695                 700

Gln Asp Thr Gly Leu Leu Glu Ile Phe Lys Ile Pro Thr Gln Gln Phe
705                 710                 715                 720

Met Asn Tyr Phe Arg Ala Leu Glu Asn Gly Tyr Arg Asp Ile Pro Tyr
```

```
                      725                 730                 735
His Asn Arg Ile His Ala Thr Asp Val Leu His Ala Val Trp Tyr Leu
                  740                 745                 750
Thr Thr Arg Pro Val Pro Gly Leu Gln Gln Ile His Asn Gly Cys Gly
              755                 760                 765
Thr Gly Asn Glu Thr Asp Ser Asp Gly Arg Ile Asn His Gly Arg Ile
          770                 775                 780
Ala Tyr Ile Ser Ser Lys Ser Cys Ser Asn Pro Asp Glu Ser Tyr Gly
785                 790                 795                 800
Cys Leu Ser Ser Asn Ile Pro Ala Leu Glu Leu Met Ala Leu Tyr Val
                  805                 810                 815
Ala Ala Ala Met His Asp Tyr Asp His Pro Gly Arg Thr Asn Ala Phe
              820                 825                 830
Leu Val Ala Thr Asn Ala Pro Gln Ala Val Leu Tyr Asn Asp Arg Ser
          835                 840                 845
Val Leu Glu Asn His His Ala Ala Ser Ala Trp Asn Leu Tyr Leu Ser
850                 855                 860
Arg Pro Glu Tyr Asn Phe Leu Leu His Leu Asp His Val Glu Phe Lys
865                 870                 875                 880
Arg Phe Arg Phe Leu Val Ile Glu Ala Ile Leu Ala Thr Asp Leu Lys
                  885                 890                 895
Lys His Phe Asp Phe Leu Ala Glu Phe Asn Ala Lys Ala Asn Asp Val
              900                 905                 910
Asn Ser Asn Gly Ile Glu Trp Ser Asn Glu Asn Asp Arg Leu Leu Val
          915                 920                 925
Cys Gln Val Cys Ile Lys Leu Ala Asp Ile Asn Gly Pro Ala Lys Val
930                 935                 940
Arg Asp Leu His Leu Lys Trp Thr Glu Gly Ile Val Asn Glu Phe Tyr
945                 950                 955                 960
Glu Gln Gly Asp Glu Glu Ala Asn Leu Gly Leu Pro Ile Ser Pro Phe
                  965                 970                 975
Met Asp Arg Ser Ser Pro Gln Leu Ala Lys Leu Gln Glu Ser Phe Ile
              980                 985                 990
Thr His Ile Val Gly Pro Leu Cys Asn Ser Tyr Asp Ala Ala Gly Leu
          995                 1000                1005
Leu Pro Gly Gln Trp Leu Glu Ala Glu Glu Asp Asn Asp Thr Glu
      1010                1015                1020
Ser Gly Asp Asp Glu Asp Gly Glu Glu Leu Asp Thr Glu Asp Glu
  1025                1030                1035
Glu Met Glu Asn Asn Leu Asn Pro Lys Pro Arg Arg Lys Ser
1040                1045                1050
Arg Arg Arg Ile Phe Cys Gln Leu Met His His Leu Thr Glu Asn
  1055                1060                1065
His Lys Ile Trp Lys Glu Ile Val Glu Glu Glu Lys Cys Lys
      1070                1075                1080
Ala Asp Gly Asn Lys Leu Gln Val Glu Asn Ser Ser Leu Pro Gln
  1085                1090                1095
Ala Asp Glu Ile Gln Val Ile Glu Glu Ala Asp Glu Glu
      1100                1105                1110

<210> SEQ ID NO 9
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      PDE3A_sg2 Forward oligonucleotide

<400> SEQUENCE: 9
caccgagaca agcttgctat tccaa                                              25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      PDE3A_sg2 Reverse oligonucleotide

<400> SEQUENCE: 10
aaacttggaa tagcaagctt gtctc                                              25
```

COMPOUNDS, COMPOSITIONS AND METHODS FOR CANCER TREATMENT

This application is the U.S. National Phase application, pursuant to 35 U.S.C. § 371, of PCT International Application Serial No. PCT/EP2018/052491, filed Feb. 1, 2018, designating the United States and published in English, which claims the benefit of and priority to the following U.S. Provisional Application No. 62/454,407, filed Feb. 3, 2017.

STATEMENT OF RIGHTS TO INVENTIONS MADE UNDER FEDERALLY SPONSORED RESEARCH

This invention was made with Government support under Grant No. 3U54HG005032 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 10, 2019, is named 167741.016306_US_SL.txt and is 50,862 bytes in size.

BACKGROUND OF THE INVENTION

Cancer kills over 550,000 people in the United States and over 8 million people world-wide each year. New agents, including small molecules, molecules that impact tissue-specific growth requirements, and immunomodulatory agents, have been shown to benefit a subset of patients whose cancers have unique genomic mutations or other characteristics. Unfortunately, many cancer patients are still left without effective therapeutic options.

One approach to identify new anti-cancer agents is phenotypic screening to discover novel small molecules displaying strong selectivity between cancer cell lines, followed by predictive chemogenomics to identify the cell features associated with drug response. In the 1990s, Weinstein and colleagues demonstrated that the cytotoxic profile of a compound can be used to identify cellular characteristics, such as gene-expression profiles and DNA copy number, that correlate with drug sensitivity. The ability to identify the features of cancer cell lines that mediate their response to small molecules has strongly increased in recent years with automated high-throughput chemosensitivity testing of large panels of cell lines coupled with comprehensive genomic and phenotypic characterization of the cell lines. Phenotypic observations of small molecule sensitivity can be linked to expression patterns or somatic alterations, as in the case of trastuzumab-sensitive HER2-amplified breast cancer or erlotinib-sensitive EGFR-mutant lung cancer.

Savai et al (Expert Opinion on investigational Drugs, Vol. 19, issue 1, 2010, p. 117-131) stated that targeting cancer with phosphodiesterase inhibitors might be a promising approach for the treatment of cancer. However several phosphodiesterase inhibitors have been approved for clinical treatment, including PDE3 inhibitors milrinone, cilostazol, and levosimendan for cardiovascular indications and inhibition of platelet coagulation, as well as the PDE3 inhibitor anagrelide for thrombocythemia but for no cancer indication. The most recent quality review of PDE inhibitors (Nature Reviews Drug Discovery 13, 290-314, (2014)) barely mentions cancer. From WO 2014/164704 some new PDE3 inhibitors for the treatment of cancer are known.

Methods of characterizing malignancies at a molecular level are useful for stratifying patients, thereby quickly directing them to effective therapies. Improved methods for predicting the responsiveness of subjects having cancer are urgently required.

SUMMARY OF THE INVENTION

As described below, the present invention features compounds, methods for their preparation and methods for cancer treatment.

The compounds are suitable for the treatment of a patient having a cancer that is sensitive to treatment with a phosphodiesterase 3A (PDE3A) and/or phosphodiesterase 3B (PDE3B) modulator (e.g., Compounds 1 and 2) by detecting co-expression of PDE3A and/or PDE3B and Schlafen 12 (SLFN12) polynucleotides or polypeptides and/or a lack of decrease in expression of CREB3L1 polynucleotides or polypeptides in a cancer cell derived from such patients.

In one aspect, the invention provides compounds having the structure

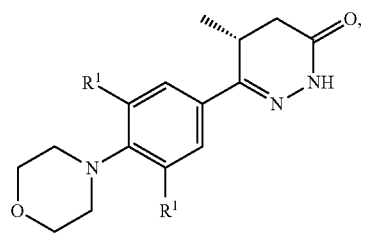

where $R^1$ is the same at each occurrence and is Cl or F or a pharmaceutically acceptable salt, or prodrug thereof.

In a further aspect, the invention provides a compound having the structure:

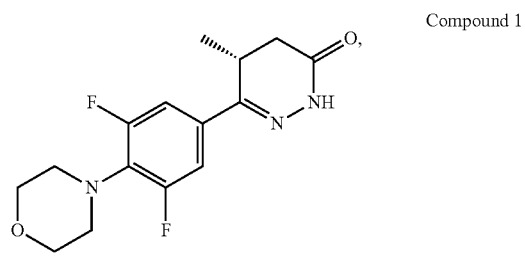 [SMILES: C[C@@H]1CC(=O)NN=C1c1cc(F)c(N2CCOCC2)c(F)c1]

Compound 1 or a pharmaceutically acceptable salt, or prodrug thereof.

In a further aspect, the invention provides compounds having the structure:

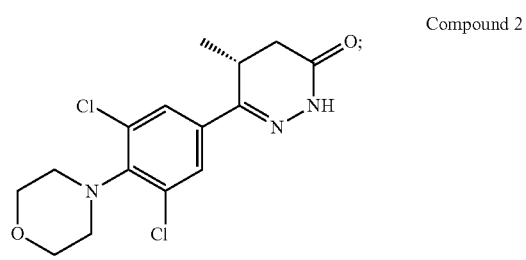 [SMILES: C[C@@H]1CC(=O)NN=C1c1cc(Cl)c(N2CCOCC2)c(Cl)c1]

Compound 2 or a pharmaceutically acceptable salt, or prodrug thereof.

In another aspect, the invention provides a pharmaceutical composition containing one or more pharmaceutically acceptable carriers or excipients and a compound of formula (I)

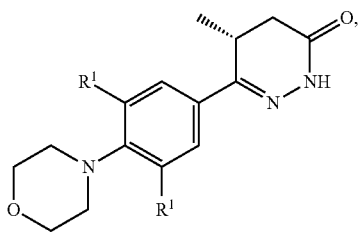

formula (I)

where $R^1$ is the same at each occurrence and is Cl or F or a pharmaceutically acceptable salt, or prodrug thereof.

In another aspect, the invention provides a pharmaceutical composition containing one or more pharmaceutically acceptable carriers or excipients and one of the compounds selected from the group consisting of:

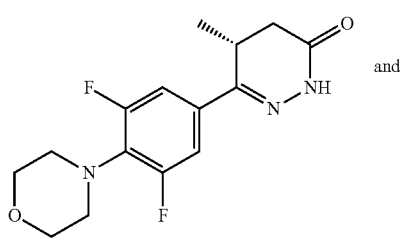

Compound 1 and

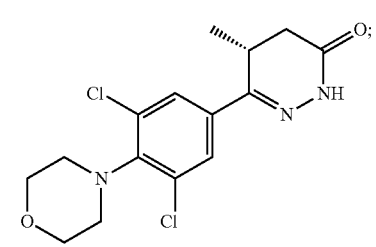

Compound 2 or a pharmaceutically acceptable salt, or prodrug thereof.

In one aspect, the invention provides a method of killing or reducing the survival of a cancer cell selected as responsive to a phosphodiesterase 3A (PDE3A) and/or phosphodiesterase 3B (PDE3B) modulator involving contacting the cell with a PDE3A and/or PDE3B modulator having the structure:

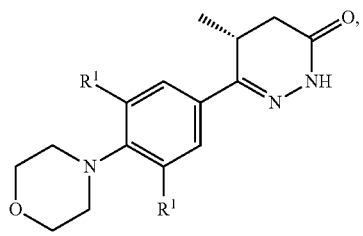

where $R^1$ is the same at each occurrence and is Cl or F or a pharmaceutically acceptable salt, or prodrug thereof.

In some embodiments the cell is selected as having an increase in the level of a PDE3A and/or PDE3B or Schlafen 12 (SLFN12) polypeptide or polynucleotide, or combination thereof, relative to a reference, thereby reducing the survival of the cancer cell.

In another aspect, the invention provides a method of reducing cancer cell proliferation in a subject pre-selected as having a cancer that is responsive to a PDE3A and/or PDE3B modulator involving contacting the cell with a PDE3A and/or PDE3B modulator having the structure:

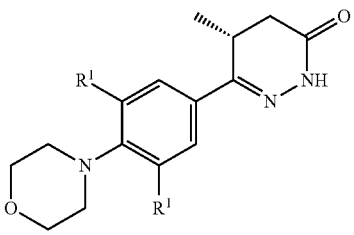

where $R^1$ is the same at each occurrence and is Cl or F or a pharmaceutically acceptable salt, or prodrug thereof, and where the subject is pre-selected by detecting an increase in the level of a PDE3A and/or PDE3B or Schlafen 12 (SLFN12) polypeptide or polynucleotide, or combination thereof, relative to a reference, thereby reducing cancer cell proliferation in said subject.

In some embodiments, the subject is pre-selected by detecting an increase in the level of a PDE3A and/or PDE3B polypeptide or polynucleotide and detecting an increase in the level of SLFN12 polypeptide or polynucleotide, relative to a reference, thereby reducing cancer cell proliferation upon treatment with the compound of formula (I) in said subject. In some embodiments, the subject is pre-selected by detecting an increase in the level of a PDE3A and/or PDE3B polypeptide or polynucleotide and detecting an increase in the level of SLFN12 polypeptide or polynucleotide, relative to a reference, thereby reducing cancer cell proliferation in said subject upon treatment with the compound of formula (I)

In another aspect, the invention provides a method of treating a hyperproliferative disease, particularly cancer, comprising administering to a subject in need thereof a compound of formula (I) having the structure

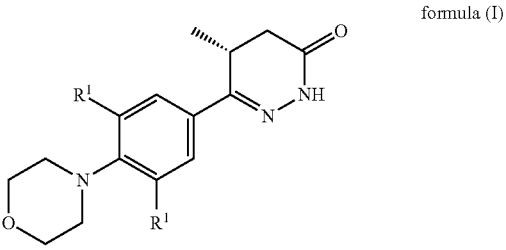

formula (I)

where $R^1$ is the same at each occurrence and is Cl or F or a pharmaceutically acceptable salt, or prodrug thereof.

In another aspect, the invention provides a method of treating a hyperproliferative disease, particularly cancer, comprising administering to a subject in need thereof a compound of formula (I) having the structure

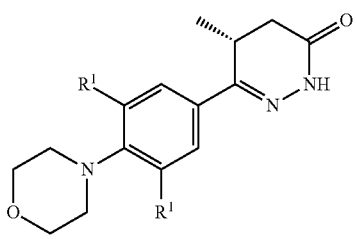

formula (I)

where R¹ is the same at each occurrence and is Cl or F; or a pharmaceutically acceptable salt, or prodrug thereof, wherein said cancer is responsive to a PDE3A and/or PDE3B modulator.

In another aspect, the invention provides a method of treating a hyperproliferative disease, particularly cancer, comprising administering to a subject in need thereof a compound of formula (I) the compound having the structure

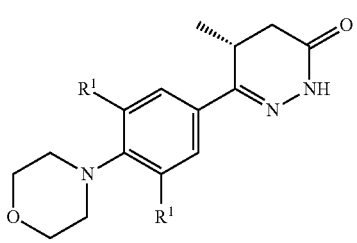

formula (I)

where R¹ is the same at each occurrence and is Cl or F; or a pharmaceutically acceptable salt, or prodrug thereof, wherein said subject has been diagnosed with a cancer responsive to a PDE3A and/or PDE3B modulator.

In another aspect, the invention provides a method of treating a hyperproliferative disease, particularly cancer, comprising administering to a subject in need thereof a compound of formula (I) having the structure

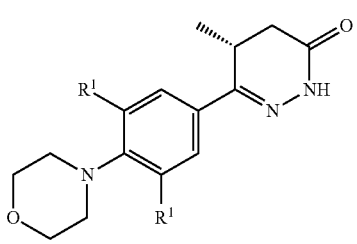

formula (I)

where R¹ is the same at each occurrence and is Cl or F, or a pharmaceutically acceptable salt, or prodrug thereof, wherein said cancer is a bone, breast, cervical, colon, endometrium, gastrointestinal stromal tumor (GIST), head and neck, hematopoetic, kidney, leiomyosarcoma, liver, lung, lymphoid, melanoma, ovarian, pancreas, prostate, skin, soft-tissue sarcoma, thyroid cancer, urinary tract cancer.

In another aspect, the invention provides a kit for decreasing cancer cell proliferation in a subject pre-selected as responsive to a PDE3A and/or PDE3B modulator containing a compound having the structure

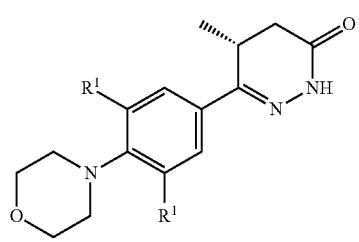

formula (I)

where R¹ is the same at each occurrence and is Cl or F; or a pharmaceutically acceptable salt, or prodrug thereof.

In another aspect, the invention provides use of a PDE3A and/or PDE3B modulator for the manufacture of a medicament for the treatment of cancer, where the PDE3A and/or PDE3B modulator is a compound of formula (I) having the structure

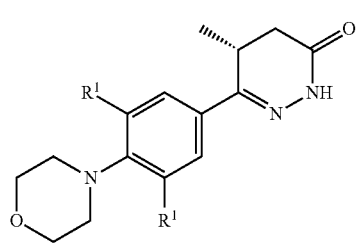

formula (I)

where R¹ is the same at each occurrence and is Cl or F; or a pharmaceutically acceptable salt, or prodrug thereof.

In another aspect, the invention provides a PDE3A and/or PDE3B modulator for use for the treatment of cancer, where the PDE3A and/or PDE3B modulator is a compound of formula (I) having the structure

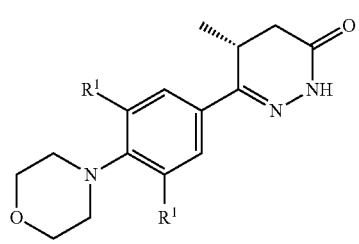

formula (I)

where R¹ is the same at each occurrence and is Cl or F; or a pharmaceutically acceptable salt, or prodrug thereof.

In other embodiments, the invention provides a PDE3A and/or PDE3B modulator for use for the treatment of cancer, where the PDE3A and/or PDE3B modulator is a compound of formula (I) having the structure

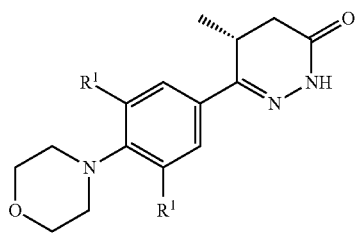

formula (I)

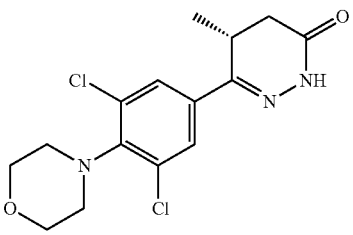

Compound 2 where R[1] is the same at each occurrence and is Cl or F; or a pharmaceutically acceptable salt, or prodrug thereof, whereby the cancer is bone, breast, cervical, colon, endometrium, gastrointestinal stromal tumor (GIST), head and neck, hematopoetic, kidney, leiomyosarcoma, liver, lung, lymphoid, melanoma, ovarian, pancreas, prostate, skin, soft-tissue sarcoma, thyroid cancer, urinary tract cancer.

In various embodiments of any aspect delineated herein, the PDE3A and/or PDE3B modulator reduces an activity of PDE3A and/or PDE3B.

In various embodiments, the PDE3A and/or PDE3B modulators have the structure:

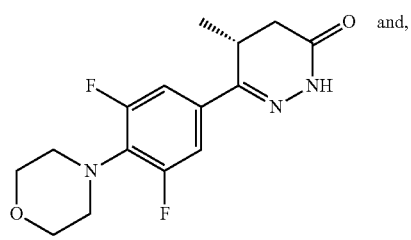

Compound 1 and,

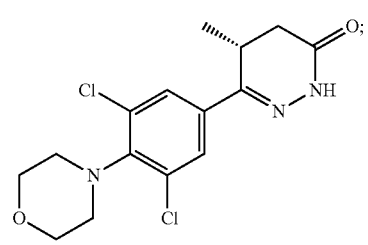

Compound 2

In some other embodiments the invention provides as PDE3A/PDE3B modulator a compound having the structure:

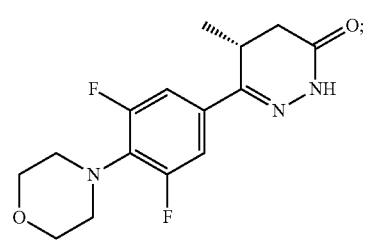

Compound 1 or a pharmaceutically acceptable salt, or prodrug thereof.

In various embodiments the inventions provides composition and methods as described above wherein the PDE3A/PDE3B modulator is Compound 1.

In another aspect the invention provides a compound having the structure:

or a pharmaceutically acceptable salt, or prodrug thereof.

In various embodiments the inventions provides composition and methods as described above wherein the PDE3A and/or PDE3B modulator is Compound 2.

In various embodiments of any aspect delineated herein, the method involves detecting a lack of a decrease in the level of expression of CREB3L1 polypeptide or polynucleotide relative to a reference.

In various embodiments of any aspect delineated herein, the method involves detecting an increase in the level of SLFN12.

In various embodiments of any aspect delineated herein, the biological sample is a tissue sample that includes a cancer cell.

In various embodiments, the level of the PDE3A, PDE3B, SLFN12, or CREB3L1 polypeptide is detected by a method selected from the group consisting of immunoblotting, mass spectrometry, and immunoprecipitation.

In various embodiments, the level of the PDE3A, PDE3B, SLFN12, or CREB3L1 polynucleotide is detected by a method selected from the group consisting of quantitative PCR, RNA sequencing, Northern Blot, microarray, mass spectrometry, and in situ hybridization.

In various embodiments of any aspect delineated herein, the cancer cell selected as responsive to a phosphodiesterase 3A (PDE3A) and/or phosphodiesterase 3B (PDE3B) modulator expresses CREB3L1 or has no loss of CREB3L1 expression relative to a reference.

In various embodiments the cancer cell being selected as responsive to a phosphodiesterase 3A (PDE3A) and/or phosphodiesterase 3B (PDE3B) modulator is a bone, breast, cervical, colon, endometrium, gastrointestinal stromal tumor (GIST), head and neck, hematopoetic, kidney, leiomyosarcoma, liver, lung, lymphoid, melanoma, ovarian, pancreas, prostate, skin, soft-tissue sarcoma, thyroid cancer, urinary tract cancer cell.

Thus in various embodiments of any aspect delineated herein, the methods disclosed above further comprise a lack of decrease in the level of CREB3L1 polypeptide or polynucleotide relative to a reference.

In various embodiments of any aspect delineated herein, the cancer cell that is resistant to a phosphodiesterase 3A (PDE3A) and/or phosphodiesterase 3B (PDE3B) modulator has decreased expression of CREB3L1 and/or SLFN12 or loss of CREB3L1 and/or SLFN12 expression relative to a reference.

In various embodiments, the cancer cell selected as responsive to a phosphodiesterase 3A (PDE3A) and/or phosphodiesterase 3B (PDE3B) modulator is a skin (e.g., melanoma), endometrium, lung, hematopoetic/lymphoid, ovarian, cervical, soft-tissue sarcoma, leiomyosarcoma, urinary tract, pancreas, thyroid, kidney, glioblastoma, or breast cancer cell.

In various embodiments, the cancer cell selected as responsive to a phosphodiesterase 3A (PDE3A) and/or phosphodiesterase 3B (PDE3B) modulator is a bone, breast, cervical, colon, endometrium, gastrointestinal stromal tumor (GIST), head and neck, hematopoetic, kidney, leiomyosarcoma, liver, lung, lymphoid, melanoma, ovarian, pancreas, prostate, skin, soft-tissue sarcoma, thyroid cancer, urinary tract cancer cell.

In various embodiments of any aspect delineated herein, the cancer cell selected as responsive to a phosphodiesterase 3A (PDE3A) and/or phosphodiesterase 3B (PDE3B) modulator has increased expression of PDE3A and/or PDE3B and Schlafen 12 (SLFN12).

In various embodiments of any aspect delineated herein, the cancer cell that is resistant to a phosphodiesterase 3A (PDE3A) modulator has decreased expression of CREB3L1 and/or SLFN12 or loss of CREB3L1 and/or SLFN12 expression relative to a Reference.

"Reference" in this context means an average expression in a representative panel of tumor cells or tumor cell lines.

In various embodiments of any aspect delineated herein, the cancer is responsive to a PDE3A and/or PDE3B modulator.

In various embodiments, the subject has been diagnosed with a cancer responsive to a PDE3A and/or PDE3B modulator.

In various embodiments, the cancer is a melanoma, endometrium, lung, hematopoetic/lymphoid, ovarian, cervical, soft-tissue sarcoma, leiomyosarcoma, urinary tract, pancreas, thyroid, kidney, glioblastoma, or breast cancer.

In various embodiments, the cancer is a skin cancer (e.g., melanoma) or a cervical cancer.

In various embodiments of any aspect delineated herein, the PDE3A and/or PDE3B modulator is administered orally.

In various embodiments of any aspect delineated herein, the PDE3A and/or PDE3B modulator is administered by intravenous injection.

In various embodiments of any aspect delineated herein, the PDE3A/PDE3B modulator is administered orally or by intravenous injection.

The invention provides methods for treating subjects having cancer identified as responsive to treatment with a PDE3A and/or PDE3B modulator selected from Compounds 1-2 by detecting co-expression of PDE3A and/or PDE3B and Schlafen 12 (SLFN12) polynucleotides or polypeptides and/or a lack of decrease in expression of CREB3L1 polynucleotides or polypeptides in the cancer.

Consequently the invention further provides a method of detecting expression of CREB3L1 polynucleotides or polypeptides for patient stratification for treatment with Compound 1 or Compound 2 using expression of CREB3L1 polynucleotides or polypeptides as a biomarker.

The invention further provides a method of detecting expression of PDE3A and/or PDE3B and/or Schlafen 12 (SLFN12) polynucleotides or polypeptides for patient stratification for treatment with Compound 1 or Compound 2 using expression of PDE3A and/or PDE3B and/or Schlafen 12 (SLFN12) polynucleotides or polypeptides as a biomarker.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Compound 1" is meant a small molecule inhibitor having the following structure:

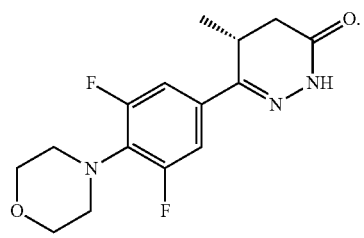

By "Compound 2" is meant a small molecule inhibitor having the following structure:

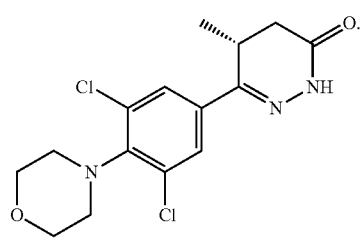

Structures drawn include all permissible rotations about bonds.

In some embodiments, any one of the compounds Compound 1, Compound 2, is a small molecule phosphodiesterase inhibitor.

In some embodiments, combinations of small molecule phosphodiesterase inhibitors or modulators may be used.

In some embodiments, any combination of Compounds 1-2 may be used.

In some embodiments, combinations of small molecule phosphodiesterase inhibitors or modulators, especially compounds 1-2, together with anticancer agents may be used.

Overview about the Synthesis of Compound 1

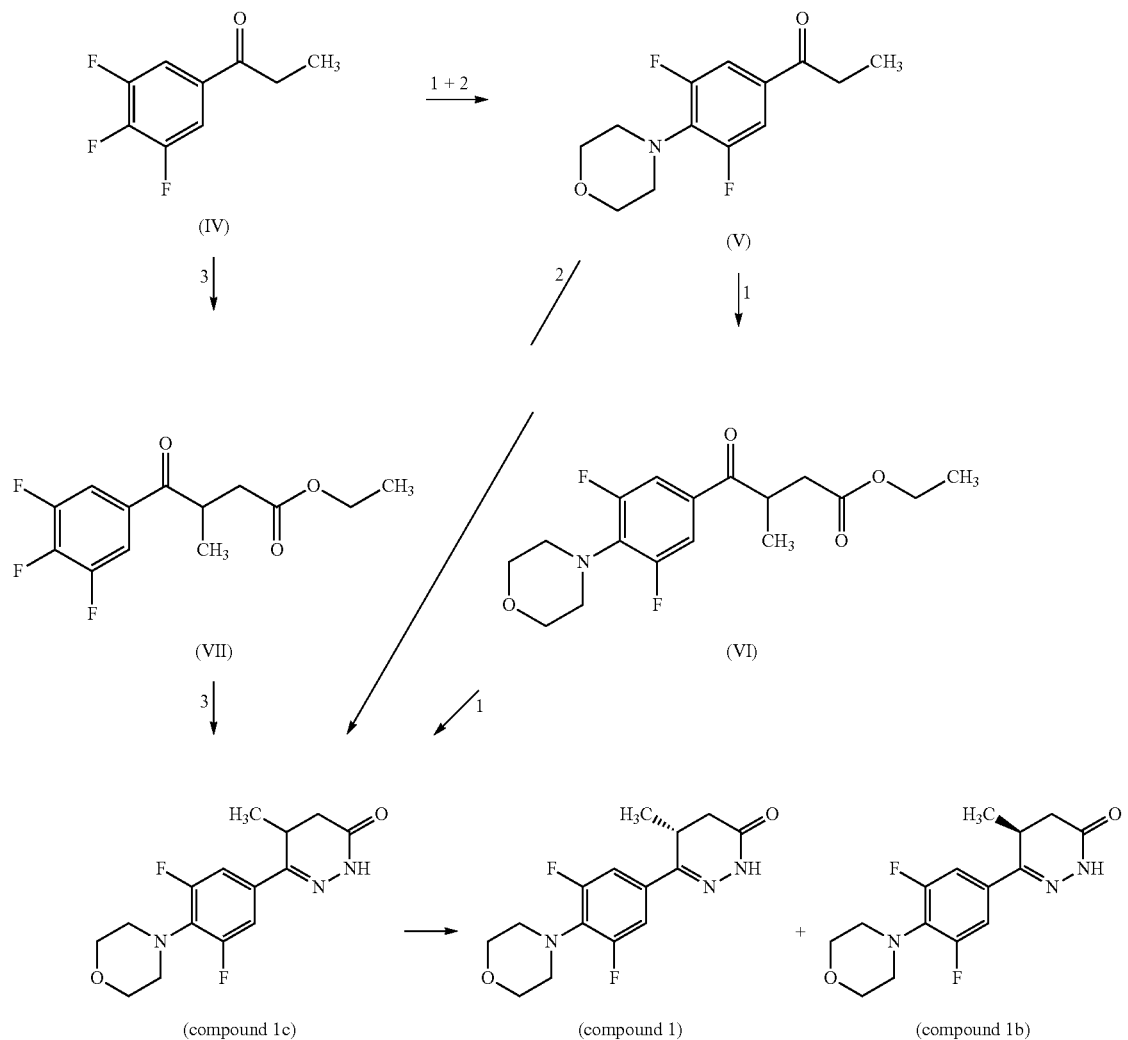

There exist several methods of preparing Compound 1. The numbers shown in the Scheme above refer to the schemes as numbered and provided in the experimental section.

In one embodiment the invention provides a method of preparing compound 1, said method comprising the steps of: reacting a compound of formula (IV)

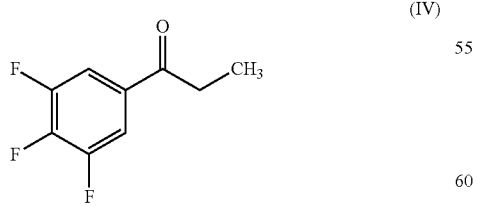

(IV)

with pure morpholine at elevated temperatures, or with morpholine and a base, such as amines or carbonates, especially N,N-diisopropylethylamine, optionally in a polar aprotic solvent, such as alcohols, or $CH_3CN$, at reflux temperature, to obtain Compound (V)

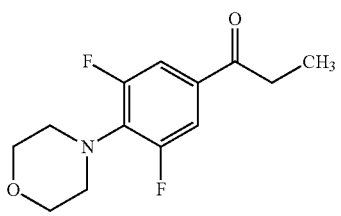

(V)

which then is reacted with a strong base, in a polar aprotic solvent at low temperatures such as −78° to −60° C. followed by addition of ($C_1$-$C_4$-alkyl)bromoacetate or ($C_1$-$C_4$-alkyl)chloroacetate neat or in a polar aprotic solvent, allowing the mixture to warm up from initial low temperature (e.g., −78° C.) to RT, optionally isolating the crude product, and then adding either hydrazine or hydrazine hydrate in a polar protic organic solvent under reflux temperature to obtain the racemic compound (1c)

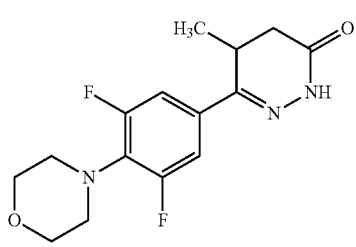

compound (1c)

and subsequently performing a separation of enantiomers of Compound (1c) to obtain Compound 1 and Compound (1a)

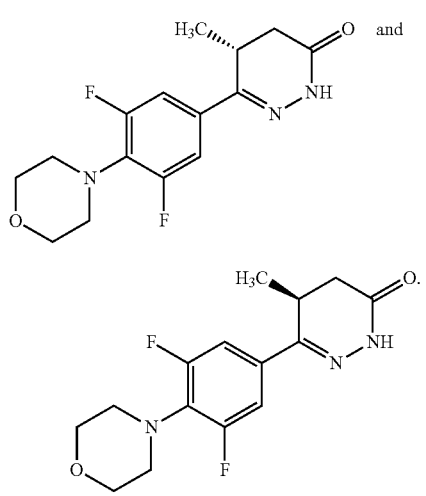

(Compound 1)

and (1a)

whereby optionally compound (1a) is converted into the racemic compound (1c) which could then be separated again in order to obtain Compound 1 and less of the initial amount of compound 1a isolated from the enantomeric separation In another embodiment the invention provides a method for the preparation of Compound 1 whereby compound (IV)

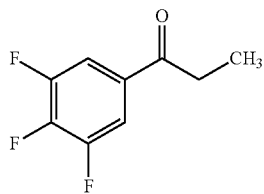

compound (IV)

is reacted with strong base in a polar aprotic solvent at low temperatures from −78° to −60° C., followed by addition of ($C_1$-$C_4$-alkyl)bromoacetate or ($C_1$-$C_4$-alkyl)chloroacetate neat or in a polar aprotic solvent allowing the mixture to warm up from initial low temperature (e.g., −78° C.) to RT, optionally isolating the crude product, and then adding either hydrazine or hydrazine hydrate in a polar protic organic solvent under reflux temperature to produce compound (VII)

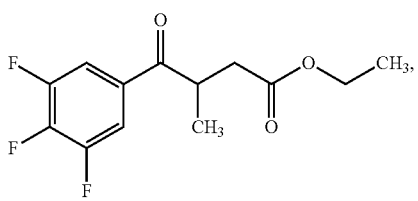

(VII)

and further allowing compound (VII) to react with pure morpholine at elevated temperatures, or with morpholine and a base in a polar aprotic solvent at reflux temperature to obtain Compound (1c)

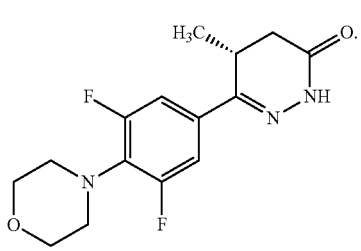

(I)

and subsequently performing a separation of enantiomers of Compound (1c) to obtain Compound 1 and Compound (1a)

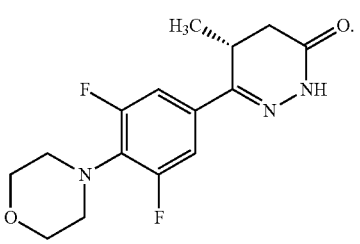

(Compound 1)

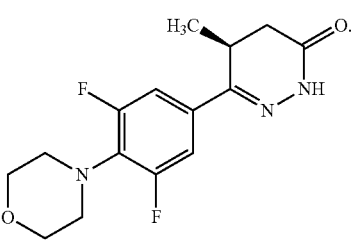

(1a)

whereby optionally compound (1a) is converted into racemic material which could then be separated in order to obtain Compound 1 and less of the initial amount of compound (1a).

In a further embodiment the invention provides the use of the intermediate compounds (IV), (V), (VI), (VII),

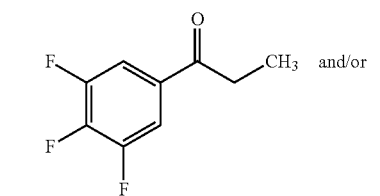
(IV)

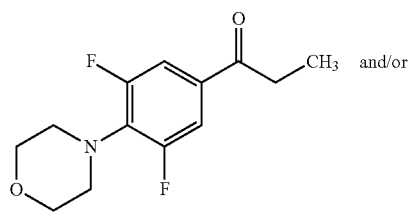
(V)

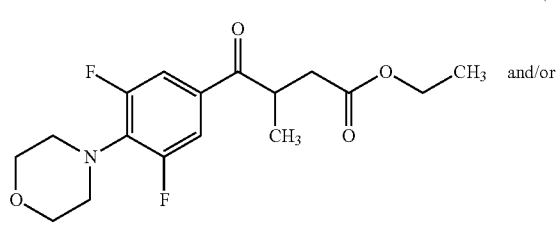
(VI)

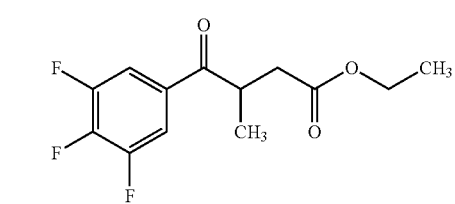
(VII)

for the preparation of compound 1

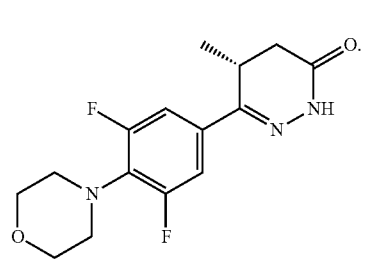 [SMILES: C[C@@H]1CC(=O)NN=C1c1cc(F)c(N2CCOCC2)c(F)c1]
(I)

A further aspect of the invention is a method of preparing compound 1, said method comprising the step of reacting the compound of formula (IV)

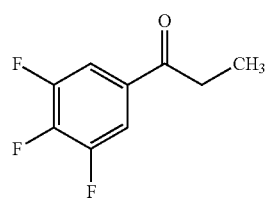
(IV)

with pure morpholine at elevated temperatures, or with morpholine and a base, such as amines e.g. diisopropylamine, triethylamine, diisoproylethylamine or carbonates e.g. sodiumcarbonate, calciumcarbonate, magensiumcarbobante, especially N,N-diisopropylethylamine, optionally in a polar solvent, such as alcohols e.g. methanol, ethanol, propanol, isopropanol, butanol (n-butanol, sec-butanol, tert-butanol), methoxyisobutanol, acetonitril, but especially $CH_3CN$, at reflux temperature to obtain Compound (V)

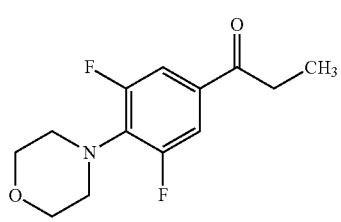
(V)

which then is reacted with a strong base, such as sodium hydride, butyllithium ($^n$BuLi, $^s$BuLi, $^t$-BuLi)), lithiumdiisopropylamide (LDA) or lithiumhexamethyldisilazide (LiHMDS), especially, LiHMDS in a polar aprotic solvent, such as tetrahydrofuran, dioxane, hexane, cyclohexane, toluene, especially tetrahydrofuran, at low temperatures such as −78° to −60° C., preferably at −78° C., followed by addition of ($C_1$-$C_4$-alkyl)bromoacetate or ($C_1$-$C_4$-alkyl)chloroacetate, especially ethyl bromoacetate, neat or in tetrahydrofuran, dioxane, hexane, cyclohexane, or toluene, especially in tetrahydofuran or other solvents, allowing the mixture to warm up from initial −78° C. to RT, optionally isolating the crude product, and then adding either hydrazine or hydrazine hydrate in a polar protic organic solvent, such as water, methanol, ethanol, propanol, isopropanol, butanol or methoxyisobutanol, preferably in ethanol under reflux temperature to obtain the racemic compound 1c

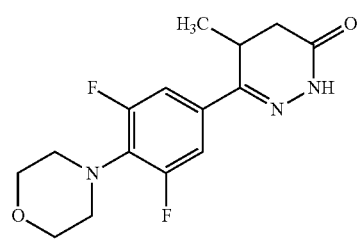
compound 1c and subsequently performing a separation of enantiomers of Compound 1c to obtain Compound 1 and Compound (1a)

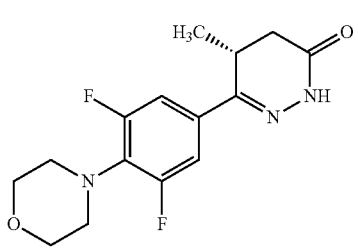
(Compound 1)

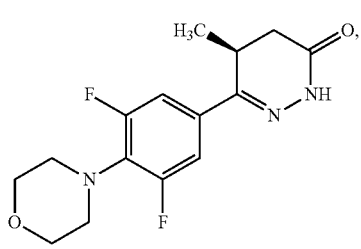

whereby optionally compound 1a is converted into compound 1c which could then be separated in order to obtain Compound 1 and less of the initial amount of compound 1a.

Another aspect of the invention is the use of compounds (V) and/or (VI) or (VII)

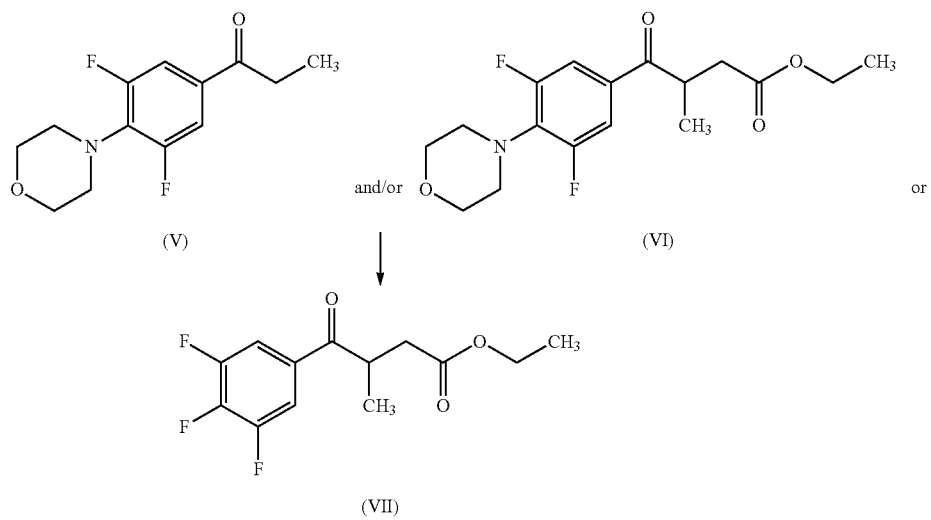

for the preparation of Compound 1

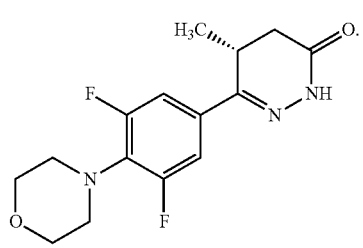

A further aspect of the invention is a method for the preparation of Compound 1 whereby the Compound (IV)

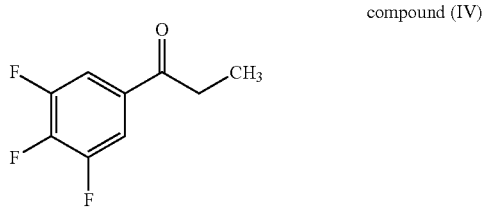

is reacted with a strong base, such as sodium hydride, butyllithium ("BuLi, ⁵BuLi, ʹ-BuLi)), lithiumdiisopropylamide (LDA) or lithiumhexamethyldisilazide (LiHMDS), especially, LiHMDS in a polar aprotic solvent, such as tetrahydrofuran, dioxane, hexane, cyclohexane, toluene, especially tetrahydrofuran, at low temperatures such as −78° to −60° C., preferably at −78° C., followed by addition of ($C_1$-$C_4$-alkyl)bromoacetate or ($C_1$-$C_4$-alkyl)chloroacetate, especially ethyl bromoacetate, neat or in tetrahydofuran, dioxane, hexane, cyclohexane, or toluene, especially in tetrahydofuran or other solvents, allowing the mixture to warm up from initial −78° C. to RT, optionally isolating the crude product, and then adding either hydrazine or hydrazine hydrate in a polar protic organic solvent, such as water, methanol, ethanol, propanol, isopropanol, butanol or methoxyisobutanol, preferably in ethanol under reflux temperature to obtain the racemic compound 1c to produce compound (VII)

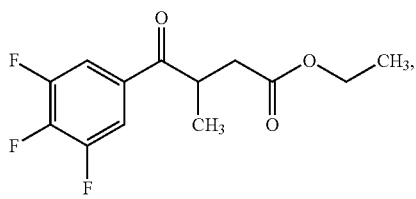

Compound (VII) and further allowing compound (VII) to react with pure morpholine at elevated temperatures, or with morpholine and a base, such as amines e.g. triethylamine, diisoproylamine, N,N-diisopropylethylamine, triethylamine or carbonates e.g. sodiumcarbonate, calciumcarbonate, magnesiumcarbonate, especially N,N-diisopropylethylamine, optionally in a polar aprotic solvent, such as alcohols e.g. methanol, ethanol, propanol, isopropanol, butanol (n-butanol, sec-butanol, tert-butanol), methoxyisobutanol or acetonitril ($CH_3CN$), at reflux temperature to obtain Compound 1c

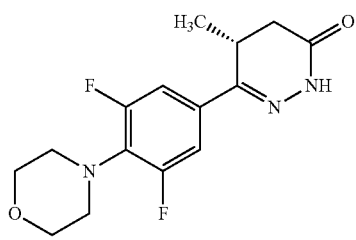
(I)

and subsequently performing a separation of enantiomers of Compound 1c to obtain Compound 1 and Compound (1a)

(Compound 1)

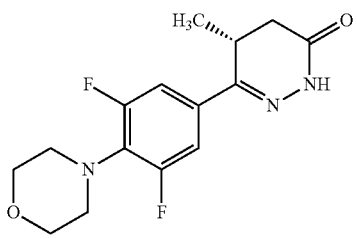

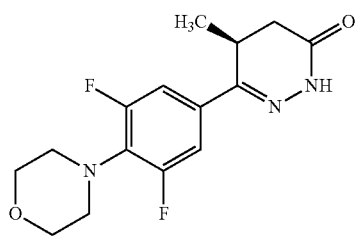
(1a)

whereby optionally compound 1a is converted into compound 1c which could then be separated in order to obtain Compound 1 and less of the initial amount of compound 1a.

Thus a further aspect if the invention is the use of compounds (IV) and (VII) for the preparation of Compound 1.

By "CREB3L1 polypeptide" is meant a protein or fragment thereof having at least 85% amino acid sequence identity to the sequence provided at GenBank Accession No. AAH14097.1 that is cleaved upon endoplasmic reticulum stress and has transcription factor activity. The amino acid sequence provided at GenBank Accession No. AAH14097.1 is shown below.

(SEQ ID NO.: 1)

```
  1 mdavlepfpa drlfpgssfl dlgdlnesdf lnnahfpehl dhftenmedf sndlfssffd
 61 dpvldekspl ldmeldsptp giqaehsysl sgdsapqspl vpikmedttq daehgawalg
121 hklcsimvkq eqspelpvdp laapsamaaa aamattpllg lsplsrlpip hqapgemtql
181 pvikaeplev nqflkvtped lvqmpptpps shgsdsdgsq sprslppssp vrpmarssta
241 istsplltpp hklqgtsgpl llteeekrtl iaegypiptk lpltkaeeka lkrvrrkikn
301 kisaqesrrk kkeyveclek kvetftsenn elwkkvetle nanrtllqql qklqtlvtnk
361 isrpykmaat qtgtclmvaa lcfvlvlgsl vpclpefssg sqtvkedpla adgvytasqm
421 psrsllfydd gaglwedgrs tllpmeppdg weinpggpae grprdhlqhd hldsthettk
481 ylseawpkdg gngtspdfsh skewfhdrdl gpnttikls
```

By "CREB3L1 polynucleotide" is meant any nucleic acid molecule, including DNA and RNA, encoding a CREB3L1 polypeptide or fragment thereof. An exemplary CREB3L1 nucleic acid sequence is provided at NCBI Ref: NM_052854.3. The sequence provided at NCBI Ref: NM_052854.3 is reproduced below:

(SEQ ID NO.: 2)

```
  1 ccagccaggg gttcccggtt tcacagagag gaaagtgaca gaagacgtgc ggagggagac
 61 gcagagacag aggagaggcc ggcagccacc cagtctcggg ggagcactta gctccccgc
121 cccggctccc accctgtccg gggggctcct gaagccctca gccccaaccc cgggctcccc
181 atggaagcca gctgtgcccc aggaggagca ggaggaggtg gagtcggctg aatgcccacg
241 gtgcgcccgg ggccctgag cccatcccgc tcctagccgc tgccctaagg ccccgcgcg
301 ccccgcgccc cccacccggg gccgcgccgc ctccgtccgc ccctccccg gggcttcgcc
361 ccggacctgc ccccgcccg tttgccagcg ctcaggcagg agctctggac tgggcgcgcc
421 gccgccctgg agtgagggaa gcccagtgga aggggtccc gggagccggc tgcgatggac
```

-continued

```
 481 gccgtcttgg aacccttccc ggccgacagg ctgttcccg gatccagctt cctggacttg 541 ggggatctga acgagtcgga cttcctcaac aatgcgcact ttcctgagca cctggaccac 601 tttacggaga acatggagga cttctccaat gacctgttca gcagcttctt tgatgaccct 661 gtgctggatg agaagagccc tctattggac atggaactgg actcccctac gccaggcatc 721 caggcggagc acagctactc cctgagcggc gactcagcgc cccagagccc ccttgtgccc 781 atcaagatgg aggacaccac ccaagatgca gagcatggag catgggcgct gggacacaaa 841 ctgtgctcca tcatggtgaa gcaggagcag agcccggagc tgcccgtgga ccctctggct 901 gcccctcgg ccatggctgc cgcggccgcc atggccacca cccgctgct gggcctcagc 961 cccttgtcca ggctgcccat ccccaccag gccccgggag agatgactca gctgccagtg 1021 atcaaagcag agcctctgga ggtgaaccag ttcctcaaag tgacaccgga ggacctggtg 1081 cagatgcctc cgacgccccc cagcagccat ggcagtgaca gcgacggctc ccagagtccc 1141 cgctctctgc cccctccag ccctgtcagg cccatggcgc gctcctccac ggccatctcc 1201 acctccccac tcctcactgc ccctcacaaa ttacaggga catcagggcc actgctcctg 1261 acagaggagg agaagcggac cctgattgct gagggctacc ccatccccac aaaactcccc 1321 ctcaccaaag ccgaggagaa ggccttgaag agagtccgga ggaaaatcaa gaacaagatc 1381 tcagcccagg agagccgtcg taagaagaag gagtatgtgg agtgtctaga aaagaaggtg 1441 gagacattta catctgagaa caatgaactg tggaagaagg tggagaccct ggagaatgcc 1501 aacaggaccc tgctccagca gctgcagaaa ctccagactc tggtcaccaa caagatctcc 1561 agaccttaca agatggccgc cacccagact gggacctgcc tcatggtggc agccttgtgc 1621 tttgttctgg tgctgggctc cctcgtgccc tgccttcccg agttctcctc cggctcccag 1681 actgtgaagg aagaccccct ggccgcagac ggcgtctaca cggccagcca gatgccctcc 1741 cgaagcctcc tattctacga tgacggggca ggcttatggg aagatggccg cagcaccctg 1801 ctgcccatgg agcccccaga tggctgggaa atcaaccccg gggggccggc agagcagcgg 1861 ccccgggacc acctgcagca tgatcacctg acagcaccc acgagaccac caagtacctg 1921 agtgaggcct ggcctaaaga cggtggaaac ggcaccagcc ccgacttctc ccactccaag 1981 gagtggttcc acgacaggga tctgggcccc aacaccacca tcaaactctc ctaggccatg 2041 ccaagaccca ggacatagga cggaccctg gtacccagaa gaggagttct tgctcactaa 2101 cccggatccg cctcgtgccc ctgcctcctg gagcttccca ttccaggaga aaggctcca 2161 cttcccagcc cttccttgcc cctgacattt ggactcttcc cttgggccga ccactctgtt 2221 ctcattctcc ttcccaccaa catccatccg tccttctcag acaaaccact cactgggtac 2281 cccacctcct ctctcatatg cccaacacga ccactgcctc cctgccccca cctgcacc 2341 caaacagaca catcaacgca ccccactcac agacacccct tacccccacc ccactgtaca 2401 gagaccaaga acagaaattg tttgtaaata atgaacctta ttttttatta ttgccaatcc 2461 cctaagatat tgtattttac aaatctccct cttcccttcg cccctccctt gttttatatt 2521 ttatgaagtt agtgcgggct ttgctgctcc ctggcccagg aaagagggac tacctgaccc 2581 tcacctggca ccccctgct gctgcccaag ccgctgggcc ttttaattg ccaaactgct 2641 ctcttcatca gctcagcaca tgcttaaga aagcaaaacc aaaaaaaaaa aaaaaaagat 2701 gcagcatcaa aaaaaaaaaa aaaaaaaaaa aaaaaaaaa a
```

By "PDE3A polypeptide" is meant a protein or fragment thereof having at least 85% amino acid sequence identity to the sequence provided at NCBI Ref No. NP_000912.3 that catalyzes the hydrolysis of cyclic adenosine monophosphate (cAMP) and cyclic guanosine monophosphate (cGMP). An exemplary human full-length PDE3A amino acid sequence is provided below:

(SEQ ID NO.: 3)
MAVPGDAARVRDKPVHSGVSQAPTAGRDCHHRADPASPRDSGCRGCWGDL

VLQPLRSSRKLSSALCAGSLSELLALLVRLVRGEVGCDLEQCKEAAAAEE

EEAAPGAEGGVFPGPRGGAPGGGARLSPWLQPSALLFSLLCAFFWMGLYL

LRAGVRLPLAVALLAACCGGEALVQIGLGVGEDHLLSLPAAGVVLSCLAA

ATWLVLRLRLGVLMIALTSAVRIVSLISLERFKVAWRPYLAYLAGVLGIL

LARYVEQILPQSAEAAPREHLGSQLIAGTKEDIPVFKRRRRSSSVVSAEM

SGCSSKSHRRISLPCIPREQLMGHSEWDHKRGPRGSQSSGTSITVDIAVM

GEAHGLITDLLADPSLPPNVCISLRAVSNLLSTQLTFQAIHKPRVNPVIS

LSENYTCSDSEESSEKDKLAIPKRLRRSLPPGLLRRVSSTWITTISATGL

PTLEPAPVRRDRSTSIKLQEAPSSSPDSWNNPVMMTLIKSRSFISSYAIS

AANHVKAKKQSRPGALAKISPLSSPCSSPLQGTPASSLVSKISAVQFPES

ADTTAKQSLGSHRALTYTQSAPDLSPQILIPPVICSSCGRPYSQGNPADE

PLERSGVATRIPSRIDDTAQVISDYETNNNSDSSDIVQNEDETECLREPL

RKASACSTYAPETMMFLDKPILAPEPLVMDNLDSIMEQLNIWNFPIFDLV

ENIGRKCGRILSQVSYRLFEDMGLFEAFKIPIREFMNYFHALEIGYRDIP

YHNRIHATDVLHAVWYLITQPIPGLSTVINDHGSTSDSDSDSGFTHGHMG

YVFSKTYNVIDDKYGCLSGNIPALELMALYVAAAMHDYDHPGRINAFLVA

TSAPQAVLYNDRSVLENHHAAAAWNLEMSRPEYNFLINLDHVEFKHERFL

VIEAILAIDLKKHFDFVAKFNGKVNDDVGIDWINENDRLLVCQMCIKLAD

INGPAKCKELHLQWIDGIVNEFYEQGDEEASLGLPISPFMDRSAPQLANL

QESFISHIVGPLCNSYDSAGLMPGKWVEDSDESGDTDDPEEEEEEAPAPN

EEETCENNESPKKKTFKRRKIYCQITQHLLQNHKMWKKVIEEEQRLAGIE

NQSLDQTPQSHSSEQIQAIKEEEEEKGKPRGEEIPTQKPDQ

Three PDE3A isoforms are known: PDE3A1, PDE3A2, and PDE3A3. PDE3A1 comprises amino acids 146-1141, PDE3A2 isoform 2 comprises amino acids 299-1141, and PDE3A3 comprises amino acids 483-1141 of the full-length PDE3A amino acid sequence.

By "PDE3A polynucleotide" is meant any nucleic acid molecule, including DNA and RNA, 25 encoding a PDE3A polypeptide or fragment thereof. An exemplary PDE3A nucleic acid sequence is provided at NCBI Ref: NM_000921.4:

(SEQ ID NO.: 4)
```
   1  gggggccact gggaattcag tgaagagggc accctatacc atggcagtgc ccggcgacgc
  61  tgcacgagtc agggacaagc ccgtccacag tggggtgagt caagccccca cggcgggccg
 121  ggactgccac catcgtgcgg accccgcatc gccgcgggac tcgggctgcc gtggctgctg
 181  gggagacctg gtgctgcagc cgctccggag ctctcggaaa ctttcctccg cgctgtgcgc
 241  gggctccctg tcctttctgc tggcgctgct ggtgaggctg gtccgcgggg aggtcggctg
 301  tgacctggag cagtgtaagg aggcggcggc ggcggaggag gaggaagcag ccccgggagc
 361  agaagggggc gtcttcccgg ggcctcgggg aggtgctccc gggggcggtg cgcggctcag
 421  cccctggctg cagccctcgg cgctgctctt cagtctcctg tgtgccttct tctggatggg
 481  cttgtacctc ctgcgcgccg gggtgcgcct gcctctggct gtcgcgctgc tggccgcctg
 541  ctgcgggggg gaagcgctcg tccagattgg gctgggcgtc ggggaggatc acttactctc
 601  actcccgcc gcggggtgg tgctcagctg cttggccgcc gcgacatggc tggtgctgag
 661  gctgaggctg ggcgtcctca tgatcgcctt gactagcgcg gtcaggaccg tgtccctcat
 721  ttccttagag aggttcaagg tcgcctggag accttacctg gcgtacctgg ccggcgtgct
 781  ggggatcctc ttggccaggt acgtggaaca atcttgccg cagtccgcgg aggcggctcc
 841  aagggagcat ttggggtccc agctgattgc tgggaccaag aagatatcc cggtgtttaa
 901  gaggaggagg cggtccagct ccgtcgtgtc cgccgagatg tccggctgca gcagcaagtc
 961  ccatcggagg acctccctgc cctgtatacc gagggaacag ctcatgggc attcagaatg
1021  ggaccacaaa cgagggccaa gaggatcaca gtcttcagga accagtatta ctgtggacat
1081  cgccgtcatg ggcgaggccc acggcctcat taccgacctc ctggcagacc cttctcttcc
1141  accaaacgtg tgcacatcct tgagagccgt gagcaacttg ctcagcacac agctcacctt
1201  ccaggccatt cacaagccca gagtgaatcc cgtcacttcg ctcagtgaaa actatacctg
```

```
1261  ttctgactct gaagagagct ctgaaaaaga caagcttgct attccaaagc gcctgagaag
1321  gagtttgcct cctggcttgt tgagacgagt ttcttccact tggaccacca ccacctcggc
1381  cacaggtcta cccaccttgg agcctgcacc agtacggaga gaccgcagca ccagcatcaa
1441  actgcaggaa gcaccttcat ccagtcctga ttcttggaat aatccagtga tgatgaccct
1501  caccaaaagc agatccttta cttcatccta tgctatttct gcagctaacc atgtaaaggc
1561  taaaaagcaa agtcgaccag gtgccctcgc taaaatttca cctctttcat cgccctgctc
1621  ctcacctctc caagggactc ctgccagcag cctggtcagc aaaatttctg cagtgcagtt
1681  tccagaatct gctgacacaa ctgccaaaca aagcctaggt tctcacaggg ccttaactta
1741  cactcagagt gccccagacc tatcccctca atcctgact ccacctgtta tatgtagcag
1801  ctgtggcaga ccatattccc aagggaatcc tgctgatgag cccctggaga aagtggggt
1861  agccactcgg acaccaagta gaacagatga cactgctcaa gttacctctg attatgaaac
1921  caataacaac agtgacagca gtgacattgt acagaatgaa gatgaaacag agtgcctgag
1981  agagcctctg aggaaagcat cggcttgcag cacctatgct cctgagacca tgatgtttct
2041  ggacaaacca attcttgctc ccgaacctct tgtcatggat aacctggact caattatgga
2101  gcagctaaat acttggaatt ttccaatttt tgatttagtg aaaatatag gaagaaaatg
2161  tggccgtatt cttagtcagg tatcttacag acttttttgaa gacatgggcc tctttgaagc
2221  ttttaaaatt ccaattaggg aatttatgaa ttattttcat gctttggaga ttggatatag
2281  ggatattcct tatcataaca gaatccatgc cactgatgtt ttacatgctg tttggtatct
2341  tactacacag cctattccag gcctctcaac tgtgattaat gatcatggtt caaccagtga
2401  ttcagattct gacagtggat ttacacatgg acatatggga tatgtattct caaaaacgta
2461  taatgtgaca gatgataaat acgatgtct gtctgggaat atccctgcct tggagttgat
2521  ggcgctgtat gtggctgcag ccatgcacga ttatgatcat ccaggaagga ctaatgcttt
2581  cctggttgca actagtgctc tcaggcggt gctatataac gatcgttcag ttttggagaa
2641  tcatcacgca gctgctgcat ggaatctttt catgtcccgg ccagagtata acttcttaat
2701  taaccttgac catgtggaat ttaagcattt ccgtttcctt gtcattgaag caattttggc
2761  cactgacctg aagaaacact ttgacttcgt agccaaattt aatggcaagg taaatgatga
2821  tgttggaata gattggacca atgaaaatga tcgtctactg gtttgtcaaa tgtgtataaa
2881  gttggctgat atcaatggtc cagctaaatg taaagaactc catcttcagt ggacagatgg
2941  tattgtcaat gaattttatg aacagggtga tgaagaggcc agccttggat tacccataag
3001  ccccttcatg gatcgttctg ctcctcagct ggccaacctt caggaatcct tcatctctca
3061  cattgtgggg cctctgtgca actcctatga ttcagcagga ctaatgcctg aaaatgggt
3121  ggaagacagc gatgagtcag gagatactga tgacccagaa gaagaggagg aagaagcacc
3181  agcaccaaat gaagaggaaa cctgtgaaaa taatgaatct ccaaaaaaga gactttcaa
3241  aaggagaaaa atctactgcc aaataactca gcacctctta cagaaccaca gatgtggaa
3301  gaaagtcatt gaagaggagc aacggttggc aggcatagaa aatcaatccc tggaccagac
3361  ccctcagtcg cactcttcag aacagatcca ggctatcaag gaagaagaag aagagaaagg
3421  gaaaccaaga ggcgaggaga taccaaccca aaagccagac cagtgacaat ggatagaatg
3481  ggctgtgttt ccaaacagat tgacttgtca aagactctct tcaagccagc acaacattta
3541  gacacaacac tgtagaaatt tgagatgggc aaatggctat tgcattttgg gattcttcgc
3601  attttgtgtg tatatttta cagtgaggta cattgttaaa aacttttgc tcaaagaagc
3661  tttcacattg caacaccagc ttctaaggat tttttaagga gggaatatat atgtgtgtgt
```

-continued

```
3721  gtatataagc tcccacatag atacatgtaa aacatattca cacccatgca cgcacacaca
3781  tacacactga aggccacgat tgctggctcc acaatttagt aacatttata ttaagatata
3841  tatatagtgg tcactgtgat ataataaatc ataaaggaaa ccaaatcaca aaggagatgg
3901  tgtggcttag caaggaaaca gtgcaggaaa tgtaggttac caactaagca gcttttgctc
3961  ttagtactga gggatgaaag ttccagagca ttatttgaat tctgatacat cctgccaaca
4021  ctgtgtgtgt gtgtgtgtgt gtgtgtgtgt gtgtgtgtgt gtgtgaaaga gagacagaag
4081  ggaatggttt gagagggtgc ttgtgtgcat gtgtgtgcat atgtaaagag atttttgtgg
4141  tttaagtaac tcagaatagc tgtagcaaat gactgaatac atgtgaacaa acagaaggaa
4201  gttcactctg gagtgtcttt gggaggcagc cattccaaat gccctcctcc atttagcttc
4261  aataaagggc cttttgctga tggagggcac tcaagggctg ggtgagaggg ccacgtgttt
4321  ggtattacat tactgctatg caccacttga aggagctcta tcaccagcct caaacccgaa
4381  agactgaggc attttccagt ctacttgcct aatgaatgta taggaactgt ctatgagtat
4441  ggatgtcact caactaagat caaatcacca tttaagggga tggcattctt tatacctaaa
4501  cacctaagag ctgaagtcag gtcttttaat caggttagaa ttctaaatga tgccagagaa
4561  ggcttgggaa attgtacttc agcgtgatag cctgtgtctt cttaatttgc tgcaaaatat
4621  gtggtagaga aagaaaagga aacagaaaaa tcactctggg ttatatagca agagatgaag
4681  gagaatattt caacacaggg ttttgtgtt gacataggaa aagcctgatt cttggcaact
4741  gttgtagttt gtctttcagg ggtgaaggtc ccactgacaa cccctgttgt ggtgttccac
4801  acgctgtttg ttggggtagc ttccatcggc agtctggccc attgtcagtc atgcttcttc
4861  tggccgggga gattatagag agattgtttg aagattgggt tattattgaa agtcttttt
4921  tttgtttgtt ttgttttggt ttgtttgttt atctacactt gtttatgctg tgagccaaac
4981  ctctatttaa aaagttgata ctcactttca atatttatt tcatattatt atatatgtca
5041  tgatagttat cttgatgtaa atatgaagat ttttttgttt ctgtagatag taaactcttt
5101  ttttaaaaaa ggaaaaggga aacattttta taaagttata ttttaatcac cattttata
5161  cattgtagtt ctctccaagc ccagtaagag aatgatgatt catttgcatg gaggtcgatg
5221  gacaaccaat catctaccct ttctaattta aatgataatc tgatatagtt ttattgccag
5281  ttaaatgagg atgctgcaaa gcatgttttt tcactagtaa cttttgctaa ctgaatgaat
5341  tctgggtcca tatctcccag atgaaaaact gttaaccaat accatatttt atagttggtg
5401  tccatttctt tccaacactg tttgttatga ttcttccttg agtacttata tacagacctg
5461  ctcattatct aaacaatctt accttctaag taaaccttga ttgtgatttc cagttttat
5521  tttctctgac gtagtagaaa ggaatgttta cattaaaaat acttttgttt ctcataaatg
5581  gatattgtac tccccccttt caaagcatta ttttacaata attcatggca ttttaaaaaa
5641  taaggcaaag ataatacgac aaaaaatata catggtttca aggcaaattc tccaataagt
5701  tggaaaatgt aaaaaggatc aagtggatgc agcctctacc taaataatta aaatatattt
5761  cagtatattt ctgaattaac accaggtctt cattatttag aacttactaa attgttttca
5821  ttttcttagt tttacctgtg tatctccatg tttgcaaaaa ttactataag tcaaattttg
5881  ccagtgaatt taactatttt tctttccttg caattaaggg gaaaaaagca tttatcttat
5941  cttctcatac cccttgcatc taagtactta gcaaagtcaa tattttccca ttttccaaat
6001  gcgtccatct ctaacataaa tattaattga acatagagct atgtttggag tgagtggact
6061  ggcaggacag ttggaagtcc atcacagtct attgacagtt tcatcaaagc tgtatagtcc
```

```
6121  aactagtggg gcagcttggc tactatggtg gaagtctcag caaactgcct ggttttgttt 6181  gtttgttttg ttttaaggta caggaaataa gaggaataat agtggccaaa gcaattagaa 6241  catcttcatt ccagaactgt gttcagcaat ccaggcagat tgatacattt ttctttaaaa 6301  ataaattgct attacagcta gacgtcaatt gggataaata aagggatgaa gatccactaa 6361  gtttgtgact ttcatacaca cccagtacat ctcaaaggat gctaagggac attttctgcc 6421  agtagagttc tcccccttt tggtgacagc aatattatta tgttcacatc taactccaga 6481  gcttacttcc tgtggtgcca atgtatttgt tgcaatttac tacatttta tatgagccta 6541  tttataggtg ccattaaact caggtctttc aaatgaaaga gtttctagcc cacttaggga 6601  aaaagataat tgtttagaaa accataaaat caatggtagg aaaagttgga actggttacc 6661  tggatgccat ggttctctgt taaataaagt aagagaccag gtgtattctg agtgtcatca 6721  gtgttatttt cagcatgcta ataaatgtct ttccggttat atatctatct aaattaacct 6781  ttaaaatatt ggtttccttg ataaaagcac cactttgct tttgttagct gtaatatttt 6841  ttgtcattta gataagacct ggtttggctc tcaataaaag atgaagacag tagctctgta 6901  cagggatata tctatattag tcttcatctg atgaatgaag aaatttctc atattatgtt 6961  caagaaagta tttacttcct aaaaatagaa ttcccgattc tgtctatttt ggttgaatac 7021  cagaacaaat ctttccgttg caatcccagt aaaacgaaag aaaaggaata tcttacagac 7081  tgttcatatt agatgtatgt agactgttaa tttgcaattt ccccatattt cctgcctatc 7141  ttacccagat aactttctt gaaggtaaaa gctgtgcaaa aggcatgaga ctcaggccta 7201  ctctttgttt aaatgatgga aaaatataaa ttattttcta agtaataaaa gtataaaaat 7261  tatcattata aataaagtct aagtttgaa attattaatt taaaaaaaaa aaaaaaaaa
```

By "Schlafen 12 (SLFN12) polypeptide" is meant a protein or fragment thereof having at least 85% amino acid sequence identity to the sequence provided at NCBI Ref No. NP_060512.3 that interacts with PDE3A when bound to one of the compounds described herein. An exemplary human SLFN12 amino acid sequence is provided below:

(SEQ ID NO.: 5)
MNISVDLETNYAELVLDVGRVTLGENSRKKMKDCKLRKKQNESVSRAMCA
LLNSGGGVIKAEIENEDYSYTKDGIGLDLENSFSNILLFVPEYLDFMQNG
NYFLIFVKSWSLNTSGLRITTLSSNLYKRDITSAKVMNATAALEFLKDMK
KTRGRLYLRPELLAKRPCVDIQEENNMKALAGVFFDRIELDRKEKLTFTE
STHVEIKNFSTEKLLQRIKEILPQYVSAFANIDGGYLFIGLNEDKEIIGF
KAEMSDLDDLEREIEKSIRKMPVHHFCMEKKKINYSCKFLGVYDKGSLCG
YVCALRVERFCCAVFAKEPDSWHVKDNRVMQLTRKEWIQFMVEAEPKFSS
SYEEVISQINTSLPAPHSWPLLEWQRQRHHCPGLSGRITYTPENLCRKLF
LQHEGLKQLICEEMDSVRKGSLIFSRSWSVDLGLQENHKVLCDALLISQD
SPPVLYTFHMVQDEEFKGYSTQTALTLKQKLAKIGGYIKKVCVMTKIFYL
SPEGMTSCQYDLRSQVIYPESYYFTRRKYLLKALFKALKRLKSLRDQFSF
AENLYQIIGIDCFQKNDKKMFKSCRRLT

By "Schlafen 12 (SLFN12) polynucleotide" is meant any nucleic acid molecule, including DNA and RNA, encoding a SLFN12 polypeptide or fragment thereof. An exemplary SLFN12 nucleic acid sequence is provided at NCBI Ref: NM_018042.4:

```
                                              (SEQ ID NO.: 6)
  1  tttgtaactt cacttcagcc tcccattgat cgctttctgc aaccattcag actgatctcg 61  ggctcctatt tcatttacat tgtgtgcaca ccaagtaacc agtgggaaaa ctttagaggg 121  tacttaaacc ccagaaaatt ctgaaaccgg gctcttgagc cgctatcctc gggcctgctc 181  ccaccctgtg gagtgcactt tcgttttcaa taaatctctg cttttgttgc ttcattcttt 241  ccttgctttg tttgtgtgtt tgtccagttc tttgttcaac acgccaagaa cctggacact 301  cttcactggt aacatatttt ggcaagccaa ccaggagaaa agaatttctg cttggacact 361  gcatagctgc tgggaaaatg aacatcagtg ttgatttgga aacgaattat gccgagttgg 421  ttctagatgt gggaagagtc actcttggag agaacagtag gaaaaaaatg aaggattgta
```

-continued

```
 481 aactgagaaa aaagcagaat gaaagtgtct cacgagctat gtgtgctctg ctcaattctg
 541 gagggggagt gatcaaggct gaaattgaga atgaagacta tagttataca aaagatggaa
 601 taggactaga tttggaaaat tcttttagta acattctgtt atttgttcct gagtacttag
 661 acttcatgca gaatggtaac tactttctga ttttgtgaa gtcatggagc ttgaacacct
 721 ctggtctgcg gattaccacc ttgagctcca atttgtacaa aagagatata acatctgcaa
 781 aagtcatgaa tgccactgct gcactggagt tcctcaaaga catgaaaaag actagaggga
 841 gattgtattt aagaccagaa ttgctggcaa agaggccctg tgttgatata caagaagaaa
 901 ataacatgaa ggccttggcc ggggtttttt ttgatagaac agaacttgat cggaaagaaa
 961 aattgacctt tactgaatcc acacatgttg aaattaaaaa cttctcgaca gaaaagttgt
1021 tacaacgaat taaagagatt ctccctcaat atgtttctgc atttgcaaat actgatggag
1081 gatatttgtt cattggttta aatgaagata agaaataat tggctttaaa gcagagatga
1141 gtgacctcga tgacttagaa agagaaatcg aaaagtccat taggaagatg cctgtgcatc
1201 acttctgtat ggagaagaag aagataaatt attcatgcaa attccttgga gtatatgata
1261 aaggaagtct ttgtggatat gtctgtgcac tcagagtgga gcgcttctgc tgtgcagtgt
1321 ttgctaaaga gcctgattcc tggcatgtga agataaccg tgtgatgcag ttgaccagga
1381 aggaatggat ccagttcatg gtggaggctg aaccaaaatt ttccagttca tatgaagagg
1441 tgatctctca aataaatacg tcattacctg ctcccccacag ttggcctctt ttggaatggc
1501 aacggcagag acatcactgt ccagggctat caggaaggat aacgtatact ccagaaaacc
1561 tttgcagaaa actgttctta caacatgaag gacttaagca attaatatgt gaagaaatgg
1621 actctgtcag aaagggctca ctgatcttct ctaggagctg gtctgtggat ctgggcttgc
1681 aagagaacca caaagtcctc tgtgatgctc ttctgatttc ccaggacagt cctccagtcc
1741 tatacacctt ccacatggta caggatgagg agtttaaagg ctattctaca caaactgccc
1801 taaccttaaa gcagaagctg gcaaaaattg gtggttacac taaaaaagtg tgtgtcatga
1861 caaagatctt ctacttgagc cctgaaggca tgacaagctg ccagtatgat ttaaggtcgc
1921 aagtaattta ccctgaatcc tactatttta caagaaggaa atacttgctg aaagcccttt
1981 ttaaagcctt aaagagactc aagtctctga gagaccagtt ttcctttgca gaaaatctat
2041 accagataat cggtatagat tgcttttcaga agaatgataa aaagatgttt aaatcttgtc
2101 gaaggctcac ctgatggaaa atggactggg ctactgagat atttttcatt atatatttga
2161 taacattctc taattctgtg aaaatatttc tttgaaaact ttgcaagtta agcaacttaa
2221 tgtgatgttg gataattggg ttttgtctat tttcacttct ccctaaataa tcttcacaga
2281 tattgtttga gggatattag gaaaattaat ttgttaactc gtctgtgcac agtattattt
2341 actctgtctg tagttcctga ataaattttc ttccatgctt gaactgggaa aattgcaaca
2401 cttttattct taatgacaac agtgaaaatc tcccagcata tacctagaaa acaattataa
2461 cttacaaaag attatccttg atgaaactca gaatttccac agtgggaatg aataagaagg
2521 caaaactcat
```

By "PDE3B polynucleotide" is meant any nucleic acid molecule, including DNA and RNA, encoding a PDE3B polypeptide or fragment thereof. An exemplary PDE3B nucleic acid sequence is provided at NCBI Ref: NM_000922.3:

(SEQ ID NO.: 7)
ATGAGGAGGGACGAGCGAGACGCCAAAGCCATGCGGTCCCTGCAGCCGCCGGATGGGGCCGGCTCGCC

CCCCGAGAGTCTGAGGAACGGCTACGTGAAGAGCTGCGTGAGCCCCTTGCGGCAGGACCCTCCGCGCG

GCTTCTTCTTCCACCTCTGCCGCTTCTGCAACGTGGAGCTGCGGCCGCCGCCGGCCTCTCCCCAGCAG

CCGCGGCGCTGCTCCCCCTTCTGCCGGGCGCGCCTCTCGCTGGGCGCCTGGCTGCCTTTGTCCTCGC

CCTGCTGCTGGGCGCGGAACCCGAGAGCTGGGCTGCCGGGGCCGCCTGGCTGCGGACGCTGCTGAGCG

TGTGTTCGCACAGCTTGAGCCCCCTCTTCAGCATCGCCTGTGCCTTCTTCTTCCTCACCTGCTTCCTC

ACCCGGACCAAGCGGGGACCCGGCCCGGGCCGGAGCTGCGGCTCCTGGTGGCTGCTGGCGCTGCCCGC

CTGCTGTTACCTGGGGACTTCTTGGTGTGGCAGTGGTGGTCTTGGCCTTGGGGGGATGGCGACGCAG

GGTCCGCGGCCCCGCACACGCCCCGGAGGCGGCAGCGGGCAGGTTGCTGCTGGTGCTGAGCTGCGTA

GGGCTGCTGCTGACGCTCGCGCACCCGCTGCGGCTCCGGCACTGCGTTCTGGTGCTGCTCCTGGCCAG

CTTCGTCTGGTGGGTCTCCTTCACCAGCCTCGGGTCGCTGCCCTCCGCCCTCAGGCCGCTGCTCTCCG

GCCTGGTGGGGGCGCTGGCTGCCTGCTGGCCCTGGGGTTGGATCACTTCTTTCAAATCAGGGAAGCG

CCTCTTCATCCTCGACTGTCCAGTGCCGCCGAAGAAAAAGTGCCTGTGATCCGACCCCGGAGGAGGTC

CAGCTGCGTGTCGTTAGGAGAAACTGCAGCCAGTTACTATGGCAGTTGCAAAATATTCAGGAGACCGT

CGTTGCCTTGTATTTCCAGAGAACAGATGATTCTTTGGGATTGGGACTTAAAACAATGGTATAAGCCT

CATTATCAAAATTCTGGAGGTGGAAATGGAGTTGATCTTTCAGTGCTAAATGAGGCTCGCAATATGGT

GTCAGATCTTCTGACTGATCCAAGCCTTCCACCACAAGTCATTTCCTCTCTACGGAGTATTAGTAGCT

TAATGGGTGCTTTCTCAGGTTCCTGTAGGCCAAAGATTAATCCTCTCACACCATTTCCTGGATTTTAC

CCCTGTTCTGAAATAGAGGACCCAGCTGAGAAAGGGGATAGAAAACTTAACAAGGGACTAAATAGGAA

TAGTTTGCCAACTCCACAGCTGAGGAGAAGCTCAGGAACTTCAGGATTGCTACCTGTTGAACAGTCTT

CAAGGTGGGATCGTAATAATGGCAAAAGACCTCACCAAGAATTTGGCATTTCAAGTCAAGGATGCTAT

CTAAATGGGCCTTTTAATTCAAATCTACTGACTATCCCGAAGCAAAGGTCATCTTCTGTATCACTGAC

TCACCATGTAGGTCTCAGAAGAGCTGGTGTTTTGTCCAGTCTGAGTCCTGTGAATTCTTCCAACCATG

GACCAGTGTCTACTGGCTCTCTAACTAATCGATCACCCATAGAATTTCCTGATACTGCTGATTTTCTT

AATAAGCCAAGCGTTATCTTGCAGAGATCTCTGGGCAATGCACCTAATACTCCAGATTTTTATCAGCA

ACTTAGAAATTCTGATAGCAATCTGTGTAACAGCTGTGGACATCAAATGCTGAAATATGTTTCAACAT

CTGAATCAGATGGTACAGATTGCTGCAGTGGAAAATCAGGTGAAGAAGAAAACATTTTCTCGAAAGAA

TCATTCAAACTTATGGAAACTCAACAAGAAGAGGAAACAGAGAAGAAAGACAGCAGAAAATTATTTCA

GGAAGGTGATAAGTGGCTAACAGAAGAGGCACAGAGTGAACAGCAAACAAATATTGAACAGGAAGTAT

CACTGGACCTGATTTTAGTAGAAGAGTATGACTCATTAATAGAAAAGATGAGCAACTGGAATTTTCCA

ATTTTTGAACTTGTAGAAAAGATGGGAGAGAAATCAGGAAGGATTCTCAGTCAGGTTATGTATACCTT

ATTTCAAGACACTGGTTTATTGGAAATATTTAAAATTCCCACTCAACAATTTATGAACTATTTTCGTG

CATTAGAAAATGGCTATCGAGACATTCCTTATCACAATCGTATACATGCCACAGATGTGCTACATGCA

GTTTGGTATCTGACAACACGGCCAGTTCCTGGCTTACAGCAGATCCACAATGGTTGTGGAACAGGAAA

TGAAACAGATTCTGATGGTAGAATTAACCATGGGCGAATTGCTTATATTTCTTCGAAGAGCTGCTCTA

ATCCTGATGAGAGTTATGGCTGCCTGTCTTCAAACATTCCTGCATTAGAATTGATGGCTCTATACGTG

GCAGCTGCCATGCATGATTATGATCACCCAGGGAGGACAAATGCATTTCTAGTGGCTACAAATGCCCC

TCAGGCAGTTTTATACAATGACAGATCTGTTCTGGAAAATCATCATGCTGCGTCAGCTTGGAATCTAT

ATCTTTCTCGCCCAGAATACAACTTCCTTCTTCATCTTGATCATGTGGAATTCAAGCGCTTTCGTTTT

TTAGTCATTGAAGCAATCCTTGCTACGGATCTTAAAAAGCATTTTGATTTTCTCGCAGAATTCAATGC

-continued

```
CAAGGCAAATGATGTAAATAGTAATGGCATAGAATGGAGTAATGAAAATGATCGCCTCTTGGTATGCC

AGGTGTGCATCAAACTGGCAGATATAAATGGCCCAGCAAAAGTTCGAGACTTGCATTTGAAATGGACA

GAAGGCATTGTCAATGAATTTTATGAGCAGGGAGATGAAGAAGCAAATCTTGGTCTGCCCATCAGTCC

ATTCATGGATCGTTCTTCTCCTCAACTAGCAAAACTCCAAGAATCTTTTATCACCCACATAGTGGGTC

CCCTGTGTAACTCCTATGATGCTGCTGGTTTGCTACCAGGTCAGTGGTTAGAAGCAGAAGAGGATAAT

GATACTGAAAGTGGTGATGATGAAGACGGTGAAGAATTAGATACAGAAGATGAAGAAATGGAAAACAA

TCTAAATCCAAAACCACCAAGAAGGAAAAGCAGACGGCGAATATTTTGTCAGCTAATGCACCACCTCA

CTGAAAACCACAAGATATGGAAGGAAATCGTAGAGGAAGAAGAAAAATGTAAAGCTGATGGGAATAAA

CTGCAGGTGGAGAATTCCTCCTTACCTCAAGCAGATGAGATTCAGGTAATTGAAGAGGCAGATGAAGA

GGAATAG
```

By "PDE3B polypeptide" is meant a protein or fragment thereof having at least 85% amino acid sequence identity to the sequence provided at NCBI Ref No. NP_000913.2. An exemplary human PDE3B amino acid sequence is provided below:

(SEQ ID NO: 8)
```
MRRDERDAKAMRSLQPPDGAGSPPESLRNGYVKSCVSPLRQDPPRGFFFH

LCRFCNVELRPPPASPQQPRRCSPFCRARLSLGALAAFVLALLLGAEPES

WAAGAAWLRTLLSVCSHSLSPLFSIACAFFFLTCFLTRTKRGPGPGRSCG

SWWLLALPACCYLGDFLVWQWWSWPWGDGDAGSAAPHTPPEAAAGRLLLV

LSCVGLLLTLAHPLRLRHCVLVLLLASFVWWVSFTSLGSLPSALRPLLSG

LVGGAGCLLALGLDHFFQIREAPLHPRLSSAAEEKVPVIRPRRRSSCVSL

GETAASYYGSCKIFRRPSLPCISREQMILWDWDLKQWYKPHYQNSGGGNG

VDLSVLNEARNMVSDLLTDPSLPPQVISSLRSISSLMGAFSGSCRPKINP

LTPFPGFYPCSEIEDPAEKGDRKLNKGLNRNSLPTPQLRRSSGTSGLLPV

EQSSRWDRNNGKRPHQEFGISSQGCYLNGPFNSNLLTIPKQRSSSVSLTH

HVGLRRAGVLSSLSPVNSSNHGPVSTGSLTNRSPIEFPDTADFLNKPSVI

LQRSLGNAPNTPDFYQQLRNSDSNLCNSCGHQMLKYVSTSESDGTDCCSG

KSGEEENIFSKESFKLMETQQEEETEKKDSRKLFQEGDKWLTEEAQSEQQ

TNIEQEVSLDLILVEEYDSLIEKMSNWNFPIFELVEKMGEKSGRILSQVM

YTLFQDTGLLEIFKIPTQQFMNYFRALENGYRDIPYHNRIHATDVLHAVW

YLTTRPVPGLQQIHNGCGTGNETDSDGRINHGRIAYISSKSCSNPDESYG

CLSSNIPALELMALYVAAAMHDYDHPGRTNAFLVATNAPQAVLYNDRSVL

ENHHAASAWNLYLSRPEYNFLLHLDHVEFKRFRFLVIEAILATDLKKHFD

FLAEFNAKANDVNSNGIEWSNENDRLLVCQVCIKLADINGPAKVRDLHLK

WTEGIVNEFYEQGDEEANLGLPISPFMDRSSPQLAKLQESFITHIVGPLC

NSYDAAGLLPGQWLEAEEDNDTESGDDEDGEELDTEDEEMENNLNPKPPR

RKSRRRIFCQLMHHLTENHKIWKEIVEEEEKCKADGNKLQVENSSLPQAD

EIQVIEEADEEE*
```

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this invention The symbol ≈≈≈ denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the compound of the invention can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, in one embodiment an alteration includes an about 10% change in expression levels, preferably an about 25% change, more preferably an about 40% change, and most preferably an about 50% or greater change in expression levels. In certain embodiments an alteration includes a 10% or less (including 10%) change in expression levels, preferably a 25% or less (including 25%) change, more preferably a 40% or less (including 40%) change, and most preferably a 50% or less (including 50%) or greater change in expression levels. In other embodiments an alteration includes a 9%-11% (including 9% and 11%) change in expression levels, preferably a 10%-25% (including 10% and 25%) change, more preferably a 25%-40% (including 25% and 40%) change, and most preferably a 40%-50% (including 40%-50%) or greater than 50% (including 50%) change in expression levels. In other certain embodiments an alteration includes a 9%-11% (including 9% and 11%) change in expression levels, preferably a 22%-28% (including 22% and 28%) change, more preferably a 35%-45% (including 35% and 45%) change, and most preferably a 45%-55% (including 45%-55%) or a greater or equal to 55% change in expression levels By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In particular embodiments, the analyte is a PDE3A or PDE3B or SLFN12 polypeptide.

By "disease" is meant any condition or disorder that damages or interferes with the normal function of a cell, tissue, or organ. Examples of diseases include melanoma, adenocarcinoma, lung cancer, cervical cancer, liver cancer and breast cancer.

By "effective amount" is meant the amount of a compound described herein required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In still other embodiments, the PDE3A and/or PDE3B modulator is Compound 1, Compound 2.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least about 10%, about 20%, about 30%, about 40%, about 50%, about 60%, about 70%, about 80%, or about 90% of the entire length of the reference nucleic acid molecule or polypeptide. In certain embodiments this portion contains, preferably, at least 9%-11% (including 9% and 11%), 18%-22% (including 18% ands 22%), 27%-33% (including 27% and 33%), 36%-44% (including 36% and 44%), 45%-55% (including 45% and 55%), 54%-66% (including 54% and 66%), 63%-77% (including 63% and 77%), 72%-88% (including 72% and 88%), or 81%-99% (including 81% and 99%) of the entire length of the reference nucleic acid molecule or polypeptide A fragment may contain about 10, about 20, about 30, about 40, about 50, about 60, about 70, about 80, about 90, about 100, about 200, about 300, about 400, about 500, about 600, about 700, about 800, about 900, or about 1000 nucleotides or amino acids. In certain embodiments a fragment may contain 9-11, about 18-22, 27-33, 36-44, 45-55, 54-66, 63-77, 72-88, 81-99, 90-110, 180-220, 270-330, 360-440, 450-550, 540-660, 630-770, 720-880, 810-990, or 900-1100 nucleotides or amino acids (including for each the mentioned limitation e.g. for "9-11" means including 9 and 11.

"Hematological tumors" include aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

"Hyperproliferative disease" includes for example psoriasis, keloids and other hyperplasias which affect the skin, benign hyperproliferative diseases, hematopoietic hyperproliferative diseases, cancer (e.g., metastatic or malignant tumors, solid tumors, and haematological tumors).

"Benign hyperproliferative diseases" include for example, endometriosis, leiomyoma and benign prostate hyperplasia.

"Hematopoietic hyperproliferative diseases" also known as myoproliferative disorders include e.g. polycythemia vera, essential thrombocytosis, thrombocytosis, primary myelofibrosis, and others.

By "marker" or "biomarker" is meant any protein or polynucleotide having an alteration in expression level or activity (e.g., at the protein or mRNA level) that is associated with a disease or disorder. In particular embodiments, a marker of the invention is PDE3A or PDE3B or SLFN12 or CREB3L1.

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide. In some embodiments, a modulator of PDE3A/PDE3B polypeptide is DNMDP. In some other embodiments, the modulator of PDE3A/PDE3B polypeptide is anagrelide or zardaverine. In still other embodiments, the modulator of PDE3A/PDE3B polypeptide is Compound 1, Compound 2.

The term "prodrugs" or "prodrug" designates compounds which themselves can be biologically active or inactive, but are converted (for example metabolically or hydrolytically) into compounds according to the invention during their residence time in the body. Derivatives of the compound 1 and the salts thereof which are converted into compound 1 or a salt thereof in a biological system (bioprecursors or pro-drugs) are covered by the invention. Said biological system may be, for example, a mammalian organism, particularly a human subject. The bioprecursor is, for example, converted into the compound 1 or 2 or a salt thereof by metabolic processes.

By "reference" is meant a standard or control condition.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu·g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "Solid tumors" include for example, tumors of the breast, the respiratory tract, the brain, the bones, the central and peripheral nervous system, the colon, the rectum, the anus, the reproductive organs (e.g., cervix, ovary, prostate), the gastrointestinal tract, the urogenital tract, the endocrine glands (e.g., thyroid and adrenal cortex), the thyroid gland, the parathyroid gland, the esophagus, the endometrium, the eye, the germ cells, the head and the neck, the kidney, the liver, the larynx and hypopharynx, the lung, the mesothelioma, the pancreas, the prostate, the rectum, the kidney, the small intestine, the skin, the soft tissue, the stomach, the testis, ureter, vagina and vulva and the connective tissue and metastases of these tumors. Malignant neoplasias include inherited cancers exemplified by Retinoblastoma and Wilms tumor.

"Breast tumors" that can be treated include, for example, mammary carcinoma with positive hormone receptor status, mammary carcinoma with negative hormone receptor status, Her-2-positive mammary carcinoma, hormone receptor- and Her-2-negative mammary carcinoma, BRCA-associated mammary carcinoma and inflammatory mammary carcinoma.

"Tumors of the respiratory tract" that can be treated include, for example, non-small-cell bronchial carcinoma and small-cell bronchial carcinoma, non-small cell lung cancer, and small cell lung cancer.

"Brain tumors" that can be treated include, for example, glioma, glioblastoma, astrocytoma, meningioma and medulloblastoma.

"Tumors of the male reproductive organs" that can be treated include, for example, prostate carcinoma, malignant epididymal tumors, malignant testicular tumors and penile carcinoma.

"Tumors of the female reproductive organs" that can be treated include, for example, endometrial carcinoma, cervical carcinoma, ovarian carcinoma, vaginal carcinoma and vulvar carcinoma.

"Tumors of the gastrointestinal tract" that can be treated include, for example, colorectal carcinoma, anal carcinoma, gastric carcinoma, pancreatic carcinoma, oesophageal carcinoma, gallbladder carcinoma, small-intestinal carcinoma, salivary gland carcinoma, neuroendocrine tumors and gastrointestinal stromal tumors.

"Tumors of the urogenital tract" that can be treated include, for example, urinary bladder carcinoma, renal cell carcinoma, and carcinoma of the renal pelvis and of the urinary tract.

"Tumors of the eye" that can be treated include, for example, retinoblastoma and intraocular melanoma.

"Tumors of the liver" that can be treated include, for example, hepatocellular carcinoma and cholangiocellular carcinoma.

"Tumors of the skin" that can be treated include, for example, malignant melanoma, basalioma, spinalioma, Kaposi's sarcoma and Merkel cell carcinoma.

"Tumors of the head and neck" that can be treated include, for example, laryngeal carcinoma and carcinoma of the pharynx and of the oral cavity.

"Sarcomas" that can be treated include, for example, soft tissue sarcoma, synovial sarcoma, rhabdoid sarcoma and osteosarcoma.

Lymphomas that can be treated include, for example, non-Hodgkin's lymphoma, Hodgkin's lymphoma, cutaneous lymphoma, lymphoma of the central nervous system and AIDS-associated lymphoma.

Leukaemias that can be treated include, for example, acute myeloid leukaemia, chronic myeloid leukaemia, acute lymphatic leukaemia, chronic lymphatic leukaemia and hair cell leukaemia.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about. Unless specifically stated or obvious from context, as used herein, if a range is provided, the upper and lower limit are always meant to be included.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

Compositions and articles defined by the invention were isolated or otherwise manufactured in connection with the examples provided below. Other features and advantages of the invention will be apparent from the detailed description, and from the claims.

DETAILED DESCRIPTION

Figure 1:
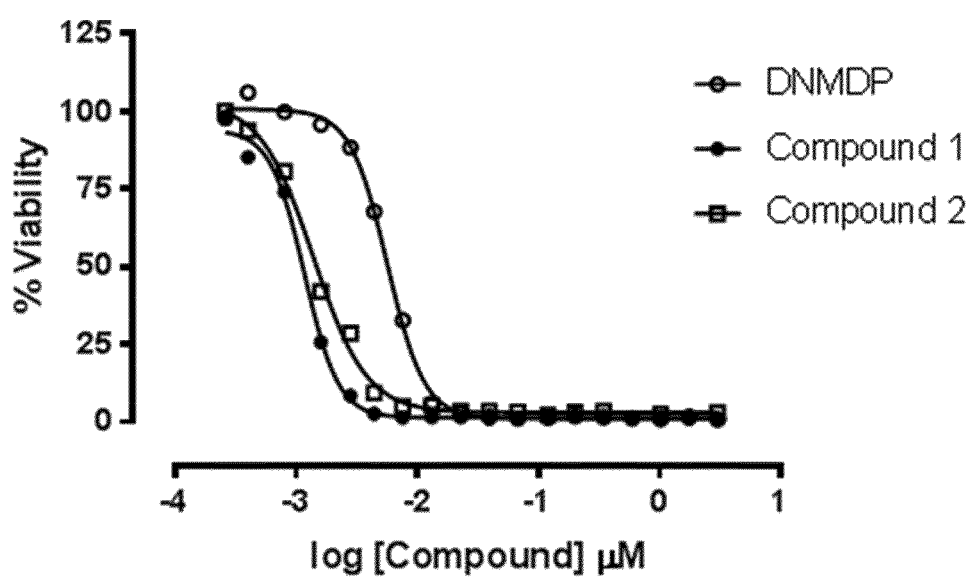
FIG. 1 provides the dose response curves for compound 1 and compound 2 in HeLa cells as obtained by the method disclosed in example 2.

The invention is based at least in part on the discovery that compounds 1 and 2 do have sensitivity to phosphodiesterase 3A modulation (PDE3A modulation) and/or phosphodiesterase 3B PDE3B modulation and do have increased stability in human hepatocytes and/or reduced clearance in dogs.

Accordingly, the invention provides methods of selecting a subject as having a cancer that responds to a PDE3A/PDE3B modulator, especially Compound 1 and/or Compound 2, where the selection method involves detecting co-expression of PDE3A and/or PDE3B and Schlafen 12 (SLFN12) polypeptides or polynucleotides, in a cancer cell derived from such subjects.

In one particular embodiment, expression of CREB3L1 and/or SLFN12 polynucleotide or polypeptide is reduced or is undetectable in a cancer cell that has acquired resistance to a PDE3A/PDE3B modulator.

PDE3A/PDE3B Modulator

The identification of PDE3A/PDE3B modulators was made in connection with a phenotypic screen designed to identify cytotoxic small molecules in a mutant tp53 background. A predictive chemogenomics approach complements target-driven drug development programs, which consists of extensive in vitro and in vivo target validation, and can also be referred to as reverse chemogenomics (Zheng et al., Curr Issues Mol Biol 4, 33-43, 2002). Many U.S. Food and Drug Administration (FDA)-approved targeted therapies have been developed this way, among them small-molecule kinase inhibitors that target oncogenic somatic driver mutations (Moffat et al., Nat Rev Drug Discov 13, 588-602, 2014). However, the discovery and development of targeted therapies is often hampered by limitations in knowledge of the biological function of the target, its mechanism of action, and the available chemical matter to selectively inhibit the target.

Phenotypic screening can discover novel targets for cancer therapy whose specific molecular mechanism is often elucidated by future studies (Swinney et al., Nat Rev Drug Discov 10, 507-519, 2011). In recent years, two classes of anti-cancer drugs found by unbiased phenotypic screening efforts have been approved by the FDA. Lenalidomide and pomalidomide were found to be modulators of an E3-ligase that alter the affinity of its target, leading to degradation of lineage specific transcription factors (Kronke et al., Science 343, 301-305, 2014; Lu et al., Science 343, 305-309, 2014), whereas romidepsin and vorinostat were later identified as histone deacetylase (HDAC) inhibitors (Moffat et al., Nat Rev Drug Discov 13, 588-602, 2014; Nakajima et al., Exp. Cell Res. 241, 126-133, 1998, Marks et al., Nat Biotechnol 25, 84-90, 2007).

Tumor suppressor alterations are suitable targets for phenotypic screening as they are not directly targetable with small molecules, although synthetic lethal approaches such as olaparib treatment of BRCA1/BRCA2 mutant cancers have proven to be effective. According to current knowledge, the tp53 tumor suppressor gene is the most frequently mutated across human cancer, with somatic mutations detected in 36% of 4742 cancers subjected to whole exome sequencing. Despite many attempts, no compounds that selectively kill tp53 mutant cells have been identified.

A phenotypic screen developed to identify small molecules causing synthetic lethality in tp53 mutant cancer cells enabled the serendipitous discovery of a class of cancer-selective cytotoxic agents which act as modulators of phosphodiesterase 3A (PDE3A) and phosphodiesterase 3B (PDE3B), as described herein below. Cyclic nucleotide phosphodiesterases catalyze the hydrolysis of second messenger molecules cyclic adenosine monophosphate (cAMP) and cyclic guanosine monophosphate (cGMP), and are important in many physiological processes. Several phosphodiesterase inhibitors have been approved for clinical treatment, including PDE3 inhibitors milrinone, cilostazol, and levosimendan for cardiovascular indications and inhibition of platelet coagulation, as well as the PDE3 inhibitor anagrelide for thrombocythemia. Further PDE3A inhibitors are known from WO 2014/164704. PDE5 inhibitors, e.g. vardenafil, are used for smooth muscle disorders including erectile dysfunction and pulmonary arterial hypertension, and the PDE4 inhibitor roflumilast reduces exacerbations from chronic obstructive pulmonary disease (COPD).

Phosphodiesterase inhibitors act by direct inhibition of their targets or by allosteric modulation; for example, structural analysis of PDE4 has led to the design of PDE4D and PDE4B allosteric modulators (Burgin et al., Nat Biotechnol 28, 63-70, 2010; Gurney et al., Neurotherapeutics 12, 49-56, 2015). The data provided herein below indicates that the cancer cytotoxic phosphodiesterase modulator DNMDP likely acts through a similar allosteric mechanism.

Accordingly, the invention provides methods for identifying subjects that have a malignancy that is likely to respond to PDE3A/PDE3B modulator treatment, especially a treatment with Compound 1 and/or Compound 2, based on the level of PDE3A and SLFN12 expression in a subject biological sample comprising a cancer cell.

In particular embodiments, the invention provides methods for identifying subjects that have a malignancy that is resistant to PDE3A modulator treatment, especially to the treatment of Compound 1 and or Compound 2, based on a loss or reduction in the level of CREB3L1 and/or SLFN12 expression relative to a reference.

Compound Forms and Salts

The compounds of the present invention include the compounds themselves, as well as their salts and their prodrugs, if applicable.

A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts.

Further, another suitably pharmaceutically acceptable salt of a compound 1-2, especially of compound 1, which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

In certain embodiments salts are derived from appropriate bases include alkali metal (e.g., sodium), alkaline earth metal (e.g., magnesium), ammonium and N-(alkyl)$_4^+$ salts. The present invention also envisions the quatemization of any basic nitrogen-containing groups of the compounds disclosed herein. Water or oil-soluble or dispersible products may be obtained by such quatemization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties. Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that undergo chemical changes under physiological conditions to provide the compounds of the present invention.

Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention, particularly deuterium-containing compounds.

The term "Isotopic variant" of a compound or a reagent is defined as a compound exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds 1 and 2, especially of compound 1, preferably contain deuterium ("deuterium-containing"). Isotopic variants of the compounds 1 and 2, especially of compound 1, in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound 1 and 2, especially in compound 1. These isotopic variants of the compounds 1 and 2 are useful for in vivo imaging applications. Deuterium-containing and $^{13}C$-containing compounds 1 and 2 can be used in mass spectrometry analyses in the context of preclinical or clinical studies.

Isotopic variants of the compounds land 2 can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compounds 1 and 2" is defined as a compound, in which one or more hydrogen atom(s) is/are replaced by one or more deuterium atom(s) and in which the abundance of deuterium at each deuterated position of anyone of the compounds 1-2 is higher than the natural abundance of deuterium, which is about 0.015%. Particularly, in anyone of deuterium-containing compounds 1-2 the abundance of deuterium at each deuterated position of the compound is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into anyone of a compound 1 and 2 may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

The compounds 1 and 2 may have multiple potential sites of attack for metabolism. To optimize the above-described effects on physicochemical properties and metabolic profile, deuterium-containing compounds 1-2 having a certain pattern of one or more deuterium-hydrogen exchange(s) can be selected. Particularly, the deuterium atom(s) of deuterium-containing compound(s) 1-2 is/are attached to a carbon atom and/or is/are located at those positions of the compound 1-2, which are sites of attack for metabolizing enzymes such as e.g. cytochrome P450.

Pharmaceutical Composition

It is possible for the compounds 1 and 2, especially for Compound 1, to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds 1 and 2 to be administered in suitable administration forms.

For oral administration, it is possible to formulate the compounds 1 and 2 to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds 1-2 in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal).

Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound 1 and 2, especially compound 1, conventionally together with one or more pharmaceutically suitable excipient(s), and to their use according to the present invention.

Thus in one embodiment the present invention relates to compound 1 or compound 2

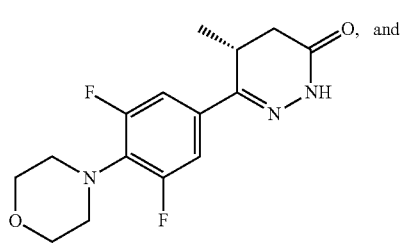

Compound 1 and

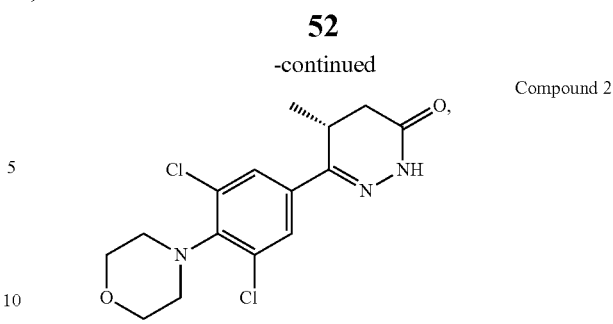

Compound 2 or a pharmaceutically acceptable salt, or prodrug thereof, and one or more pharmaceutically acceptable carriers or excipients.

In another embodiment the present invention relates to compound 1

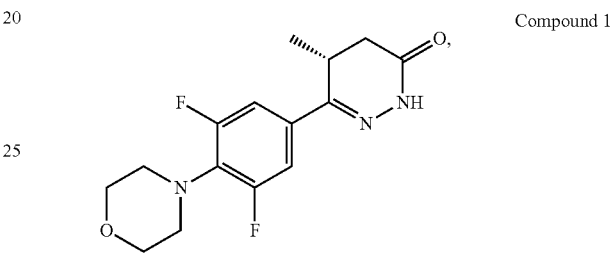

Compound 1 or a pharmaceutically acceptable salt, or prodrug thereof, and one or more pharmaceutically acceptable carriers or excipients.

In another embodiment the present invention relates to compound 2

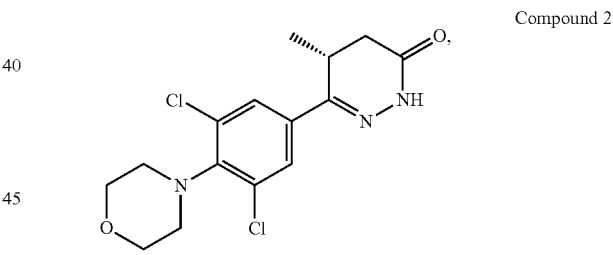

Compound 2 or a pharmaceutically acceptable salt, or prodrug thereof, and one or more pharmaceutically acceptable carriers or excipients.

Combinations

In accordance with another aspect, the present invention covers pharmaceutical combinations, in particular medicaments, comprising at least one of the compound 1 and 2, especially compound 1 and at least one or more further active ingredients, in particular for the treatment and/or prophylaxis of a hyperproliferative disease, especially cancer.

Particularly, the present invention covers a pharmaceutical combination, which comprises:

one or more first active ingredients, in particular one of the compounds 1 and 2, especially compound 1, as defined supra, and one or more further active ingredients, in particular a hyperproliferative disease, especially cancer The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more of compounds 1-2, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects.

The present invention also covers such pharmaceutical combinations. For example, the compounds of the present invention can be combined with known anticancer agents and agents ameliorating potential side effects these anticancer agents may have. Examples of these agents include: 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Utility

Compound 1 and Compound 2 are PDE3A/PDE3B modulators and thus according to the fact that targeting cancer with phosphodiesterase modulators might be a promising approach, Compound 1 and Compound 2, especially Compound 1, are useful for the treatment of cancer.

A further aspect of the invention is Compound 1 and Compound 2 for use in the treatment of hyperproliferative diseases.

A further aspect of the invention is Compound 1 and Compound 2 for use in the treatment of hyperproliferative diseases or hematopoietic hyperproliferative diseases including polycythemia vera, essential thrombocytosis, primary myelofibrosis, and others.

A further aspect is the method of prophylaxis and/or treatment, especially a method of treatment, of hyperproliferative diseases comprising administering an effective amount of Compound 1 and/or Compound 2, especially Compound 1, e.g. a method of treatment of cancer.

Yet a further aspect is the method of treating a hyperproliferative disease comprising administering to a subject in need thereof one of the compounds selected from the group consisting of

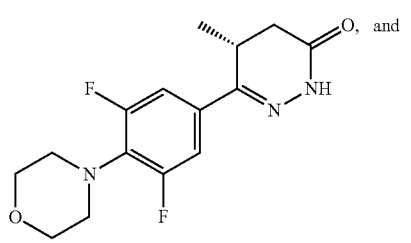

Compound 1

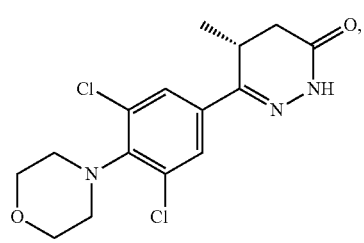

Compound 2 or a pharmaceutically acceptable salt, or prodrug thereof.

In another aspect the invention relates to a method of using one of the compounds selected from the group consisting of

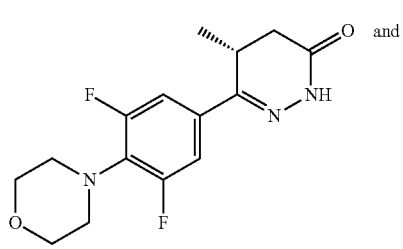

Compound 1

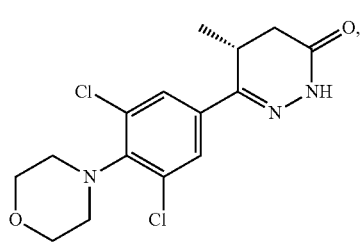 [SMILES: C[C@@H]1CC(=O)NN=C1c1cc(Cl)c(N2CCOCC2)c(Cl)c1]

Compound 2 or a pharmaceutically acceptable salt, or prodrug thereof for treating a hyperproliferative disease, more specifically where the hyperproliferative disease is cancer.

In one aspect of the invention said cancer is a bone, breast, cervical, colon, endometrium, gastrointestinal stromal tumor (GIST), head and neck, hematopoetic, kidney, leiomyosarcoma, liver, lung, lymphoid, melanoma, ovarian, pancreas, prostate, soft-tissue sarcoma, thyroid cancer, or urinary tract cancer.

The Compound 1 and/or Compound 2, especially Compound 1, are also suitable for prophylaxis and/or treatment of benign hyperproliferative diseases, for example endometriosis, leiomyoma and benign prostate hyperplasia.

Thus a further aspect is that the hyperproliferative disease is a benign hyperproliferative disease.

Another aspect of the present invention is Compound 1 and/or Compound 2, especially Compound 1, for use in the treatment of cancer. They are particular useful in treating metastatic or malignant tumors.

Thus another aspect of the invention is a method of treatment of cancer comprising administering an effective amount of at least one Compound 1 and/or 2, especially Compound 1.

A further aspect of the invention is a method of treatment of metastatic or malignant tumors comprising administering an effective amount of Compound 1 and/or 2, especially Compound 1.

Another aspect of the invention is the use of Compound 1 and/or 2, especially Compound 1 for the treatment of solid tumors.

A further aspect of the invention is the Compound 1 and/or 2, especially Compound 1 for use in the treatment of solid tumors.

A further aspect of the invention is a method of treatment of solid tumors comprising administering an effective amount of Compound 1 and/or 2, especially Compound 1.

A further aspect of the invention is the use of Compound 1 and/or 2, especially Compound 1 for the treatment of solid tumors that can be treated as tumors of the breast, the respiratory tract, the brain, the bones, the central and peripheral nervous system, the colon, the rectum, the anus, the reproductive organs (e.g., cervix, ovary, prostate), the gastrointestinal tract (including gastrointestinal stromal tumors), the urogenital tract, the endocrine glands (e.g., thyroid and adrenal cortex), the thyroid gland, the parathyroid gland, the esophagus, the endometrium, the eye, the germ cells, the head and the neck, the kidney, the liver, the larynx and hypopharynx, the lung, the mesothelioma, the pancreas, the prostate, the rectum, the kidney, the small intestine, the skin, the soft tissue, the stomach, the testis, ureter, vagina and vulva and the connective tissue and metastases of these tumors. Malignant neoplasias include inherited cancers exemplified by Retinoblastoma and Wilms tumor.

Still another aspect of the invention is a method of treatment of the tumors mentioned above comprising administering an effective amount of Compound 1 and/or 2, especially Compound 1.

Another aspect of the invention is the use of compound 1 and/or compound 2 for the treatment of hematological tumors.

A further aspect of the invention is the Compound 1 and/or 2, especially Compound 1 for use in the treatment of hematological tumors.

A further aspect of the invention is a method of treatment of hematological tumors comprising administering an effective amount of Compound 1 and/or 2, especially Compound 1.

Another aspect of the invention is the use of Compound 1 and/or 2, especially Compound 1 for the treatment of cancer whereby the cancer type is a bone, breast, cervical, colon, endometrium, gastrointestinal stromal tumor (GIST), head and neck (e.g., head, glioma, glioblastoma), hematopoetic, kidney, leiomyosarcoma, liver, lung, lymphoid, melanoma ovarian, pancreas, prostate, soft-tissue sarcoma, thyroid cancer, urinary tract cancer.

Still another aspect of the invention is the use of Compound 1 and/or 2, especially Compound 1 for the treatment of melanoma, adenocarcinoma, breast, cervical, endometrium, glioblastoma, hematopoetic/lymphoid, kidney, leiomyosarcoma, liver, lung, ovarian, pancreas, soft-tissue sarcoma, thyroid, or urinary tract cancer.

Another aspect of the invention is the use of Compound 1 and/or 2, especially Compound 1 for the treatment of cancer whereby the cancer type is a melanoma, endometrium, lung, hematopoetic, lymphoid, ovarian, cervical, soft-tissue sarcoma, leiomyosarcoma, urinary tract, pancreas, thyroid cancer.

Yet another aspect of the invention is the use of Compound 1 and/or 2, especially Compound 1 for the treatment of skin cancer (e.g., melanoma), lung cancer (e.g., lung adenocarcinoma) and cervical cancer.

Yet another aspect of the invention is the use of Compound 1 and/or 2, especially Compound 1 for the treatment of skin cancer (e.g., melanoma) and cervical cancer.

A further aspect of the invention is the use of Compound 1 and/or 2, especially Compound 1 for the treatment of cancer of bone, central nervous system (e.g., glioblastoma multiforme and glioma), colon, hematopoietic and lymphoid tissue (e.g., erythroleucemia and T-cell lymphoma), liver, lung (e.g., lung adenocarcinoma and small cell lung cancer (SCLC)), ovary, skin (e.g., melanoma).

Yet a further aspect of the invention is the use of a PDE3A and/or PDE3B modulator for the manufacture of a medicament for the treatment of cancer, where the PDE3A and/or PDE3B modulator is one of the compounds selected from the group consisting of

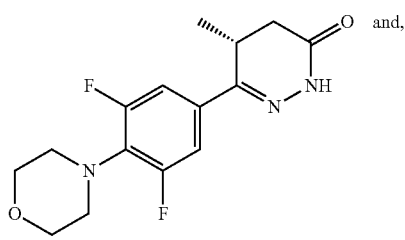

Compound 1 and,

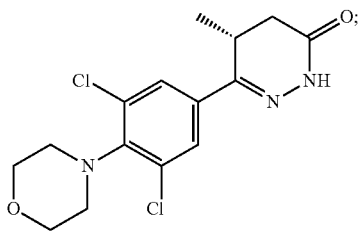

Compound 2 or a pharmaceutically acceptable salt, or prodrug thereof

Yet a further aspect of the invention is the use of a PDE3A and/or PDE3B modulator for the manufacture of a medicament for the treatment of cancer, where the PDE3A and/or PDE3B modulator is one of the compounds selected from the group consisting of Compound 1 and Compound 2 or a pharmaceutically acceptable salt, or prodrug thereof and wherein the cancer is a bone, breast, cervical, colon, endometrium, gastrointestinal stromal tumor (GIST), head and neck, hematopoetic, kidney, leiomyosarcoma, liver, lung, lymphoid, skin, melanoma, ovarian, pancreas, prostate, soft-tissue sarcoma, thyroid cancer, or urinary tract cancer, more specifically melanoma or cervical cancer.

The compounds disclosed herein may also be used in a method of reducing cancer cell proliferation in a subject.

In some embodiments, the method of reducing cancer cell proliferation in a subject comprises administering to the subject a PDE3A and/or PDE3B modulator thereby reducing cancer proliferation in the subject. The subject may be pre-selected (e.g., selected prior to administration), by detecting an increase in the level of PDE3A and/or PDE3B polypeptide or polynucleotide in a cell from the subject's cancer relative to a reference.

In some embodiments, the pre-selection of the subject may occur by detecting a decrease in the level of SLFN12 in a cell from the subject's cancer relative to a reference. In some embodiments, the pre-selection of the subject may occur by detecting a increase in the level of SLFN12 in a cell from the subject's cancer relative to a reference.

In some embodiments, the survival of the cancer cell selected as responsive to a phosphodiesterase 3A (PDE3A) and/or PDE3B modulator involving contacting the cell with one or more PDE3A and/or PDE3B modulators where the cell was selected as having an increase in the level of a PDE3A and/or PDE3B polypeptide or polynucleotide, or combination thereof, relative to a reference, thereby reducing the survival of the cancer cell.

In some embodiments a method of killing or reducing the survival of a cancer cell selected as responsive to a phosphodiesterase 3A (PDE3A) and/or PDE3B modulator is provided, wherein the method may involve contacting the cell with one or more PDE3A and/or PDE3B modulators where the cell was selected as having an increase in the level of a PDE3A and/or PDE3B polypeptide or polynucleotide, or combination thereof, relative to a reference, thereby reducing the survival of the cancer cell. Typically, the PDE3A and/or PDE3B modulator reduces the enzymatic activity of PDE3A and/or PDE3B In some embodiments, the cancer is melanoma, prostate cancer or lymphoma.

In some embodiments, the method of reducing cancer cell proliferation in a subject comprises administering to the subject a PDE3A and/or PDE3B modulator thereby reducing cancer proliferation in the subject. The subject may be pre-selected (e.g., selected prior to administration), by detecting an increase in the level of PDE3A and/or PDE3B polypeptide or polynucleotide and/or Schlafen 12 (SLFN12) in a cell from the subject's cancer relative to a reference.

In some embodiments, the survival of the cancer cell selected as responsive to a phosphodiesterase 3A (PDE3A) and/or PDE3B modulator involving contacting the cell with one or more PDE3A and/or PDE3B modulators where the cell was selected as having an increase in the level of a PDE3A and/or PDE3B polypeptide or polynucleotide or Schlafen 12 (SLFN12), or combination thereof, relative to a reference, thereby reducing the survival of the cancer cell.

In some embodiments a method of killing or reducing the survival of a cancer cell selected as responsive to a phosphodiesterase 3A (PDE3A) and/or PDE3B modulator is provided, wherein the method may involve contacting the cell with one or more PDE3A and/or PDE3B modulators where the cell was selected as having an increase in the level of a PDE3A and/or PDE3B polypeptide or polynucleotide or Schlafen 12 (SLFN12), or combination thereof, relative to a reference, thereby reducing the survival of the cancer cell upon treatment. Typically, the PDE3A and/or PDE3B modulator reduces the activity of PDE3A and/or PDE3B.

In yet further embodiments the (PDE3A) and/or PDE3B modulator used in a method mentioned herein of killing a cancer cell or reducing survival of a cancer cell is compound 1 and/or compound 2.

Thus in a further aspect the invention relates to a method of reducing cancer cell proliferation in a subject pre-selected as having a cancer that is responsive to one or more PDE3A and/or PDE3B modulators having the structure:

Compound 1

Compound 2 comprising administering to the subject the PDE3A/PDE3B modulator, where the subject is pre-selected by detecting an increase in the level of a PDE3A or PDE3B or Schlafen 12 (SLFN12) polypeptide or polynucleotide, or combination thereof, in a cell from the subject's cancer relative to a reference, thereby reducing cancer cell proliferation in said subject.

In further embodiments the (PDE3A) and/or PDE3B modulator used in said methods reduces an activity of PDE3A and/or PDE3B.

The preselection of the subject in a method mentioned herein may be performed by obtaining a biological sample (e.g. a tissue sample) of the tumor comprising the cancer cell.

In a further aspect a method as mentioned herein further comprises a step of detecting a lack of decrease in the level of expression of CREB3L1 polypeptide or polynucleotide relative to a reference.

In a further aspect a method as mentioned herein further comprises a step of detecting a lack of decrease in the level of expression of CREB3L1 polypeptide or polynucleotide relative to a reference further comprising the step of detecting a decrease in the level of SLFN12.

In one aspect for the methods disclosed herein, wherein the level of the PDE3A, PDE3B SLFN12, or CREB3L1 polypeptide is detected, this detection is made by a method selected from the group consisting of immunoblotting, mass spectrometry, and immunoprecipitation.

In one aspect for the methods disclosed herein, wherein the level of the PDE3A, PDE3B, SLFN12, or CREB3L1 polynucleotide is detected, this detection is made by a method selected from the group consisting of quantitative PCR, RNA sequencing, Northern Blot, microarray, mass spectrometry, and in situ hybridization.

In a further aspect the invention relates to a method of reducing cancer cell proliferation in a pre-selected subject, the method comprising administering to the subject one or more PDE3A and/or PDE3B modulators, wherein the subject is pre-selected by detecting an increase in the level of PDE3A and/or PDE3B polypeptide or polynucleotide in a sample derived from the subject relative to a reference, thereby reducing cancer cell proliferation in said subject.

In a further aspect the invention relates to a method of reducing cancer cell proliferation in a pre-selected subject, the method comprising administering to the subject one or more PDE3A and/or PDE3B modulators, wherein the subject is pre-selected by detecting an increase in the level of PDE3A and/or PDE3B polypeptide or polynucleotide in a sample derived from the subject relative to a reference, further comprising detecting an increase in the level of SLFN12, thereby reducing cancer cell proliferation in said subject.

In a further aspect the invention relates to a method of killing or reducing the survival of a cancer cell comprising contacting the cell with one or more PDE3A and/or PDE3B modulators, wherein the cell has an increase in the level of a PDE3A and/or PDE3B polypeptide or polynucleotide relative to a reference, thereby reducing the survival of the cancer cell.

In a further aspect the invention relates to a method of killing or reducing the survival of a cancer cell comprising contacting the cell with one or more PDE3A and/or PDE3B modulators, wherein the cell has an increase in the level of a PDE3A and/or PDE3B polypeptide or polynucleotide relative to a reference, further comprising detecting an increase in the level of SLFN12, thereby reducing the survival of the cancer cell.

In a further aspect the invention relates to a method of using compound 1 and Compound 2 for the treatment of PDE3B and SLFN 12 sensitive cancer.

In a further aspect the invention relates to a method of using compound 1 and Compound 2 for the treatment of PDE3B and SLFN12 sensitive to melanoma, prostate cancer, cervical cancer, or lymphoma.

Diagnostics

The present invention features diagnostic assays for the characterization of cancer. In one embodiment, levels of PDE3A, PDE3B, Schlafen 12 (SLFN12), or CREB3L1 polynucleotides or polypeptides are measured in a subject sample and used as an indicator of cancer that is responsive to treatment with Compound 1 and/or 2, more specifically Compound 1.

In another embodiment, the level of a CREB3L1 polynucleotide or polypeptide is measured in a biological sample of the subject. A loss of or reduction in the level of CREB3L1 or SLFN12 polynucleotide or polypeptide expression in a biological sample of the subject (e.g., a biological sample comprising a cancer cell) relative to a reference indicates that the cancer is resistant to treatment with a PDE3A and/or PDE3B modulator. Levels of PDE3A, PDE3B, SLFN12 and/or CREB3L1 polynucleotides may be measured by standard methods, such as quantitative PCR, RNA sequencing, Northern Blot, microarray, mass spectrometry, and in situ hybridization. Standard methods may be used to measure levels of PDE3A, SLFN12, and/or CREB3L1 polypeptides in a biological sample derived from a tumor. Such methods include immunoassay, ELISA, western blotting using an antibody that binds PDE3A, PDE3B, SLFN12 and/or CREB3L1, and radioimmunoassay. Elevated levels of PDE3A and SLFN12 polynucleotides or polypeptides relative to a reference are considered a positive indicator of cancer that is responsive to treatment with a PDE3A and/or PDE3B modulator. Reduced levels of a CREB3L1 or SLFN12 polynucleotide or polypeptide are considered an indicator of cancer that is resistant to treatment with Compound 1 and/or 2, especially Compound 1.

Types of Biological Samples

In characterizing the responsiveness of a malignancy in a subject to Compound 1 and/or 2, especially Compound 1 treatment, the level of PDE3A, PDE3B, SLFN12 and/or CREB3L1 expression is measured in different types of biologic samples. In one embodiment, the biologic sample is a tumor sample.

PDE3A, PDE3B and/or SLFN12 expression is higher in a sample obtained from a subject that is responsive to PDE3A and/or PDE3B modulator treatment than the level of expression in a non-responsive subject. In another embodiment, PDE3A and/or PDE3B and/or SLFN12 is at least about 5, 10, 20, or 30-fold higher in a subject with a malignancy than in a healthy control. Fold change values are determined using any method known in the art. In one embodiment, CREB3L1 or SLFN12 expression is reduced or undetectable relative to a reference.

In particular embodiments, CREB3L1 or SLFN12 expression is reduced by about 10%, 25%, 50%, 75%, 85%, 95% or more.

In one embodiment, change is determined by calculating the difference in expression of PDE3A, PDE3B SLFN12 and/or CREB3L1 in a cancer cell vs the level present in a non-responsive cancer cell or the level present in a corresponding healthy control cell.

Selection of a Treatment Method

As reported herein below, subjects suffering from a hyperproliferative disease may be tested for PDE3A, PDE3B, SLFN12 and/or CREB3L1 expression in the course of selecting a treatment method. Patients characterized as having increased PDE3A and/or SLFN12 relative to a reference level are identified as responsive to PDE3A and/or PDE3B modulator, especially to Compound 1 and/or 2, more especially to Compound 1 treatment. Subjects having reduced or undetectable levels of SLFN12 or CREB3L1 expression relative to a reference are identified as resistant to PDE3A and/or PDE3B modulator, especially to Compound 1 and/or 2, more especially to Compound 1 treatment.

Kits

The invention provides kits for characterizing the responsiveness or resistance of a subject to PDE3A and/or PDE3B modulator, especially to Compound 1 and/or 2, more especially to Compound 1 treatment.

Also provided herein are kits that can include a therapeutic composition containing an effective amount of a PDE3A and/or PDE3B modulator in, e.g., unit dosage form.

In some embodiments, the kit comprises a sterile container which includes a therapeutic or diagnostic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

In one embodiment, a kit of the invention comprises reagents for measuring PDE3A, SLFN12 and/or CREB3L1 levels. If desired, the kit further comprises instructions for measuring PDE3A and/or SLFN12 and/or instructions for administering the PDE3A/PDE3B modulator to a subject having a malignancy, e.g., a malignancy selected as responsive to PDE3A/PDE3B modulator treatment. In particular embodiments, the instructions include at least one of the following: description of the therapeutic agent; dosage schedule and administration for treatment or prevention of malignancy or symptoms thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

In one embodiment, a kit of the invention comprises reagents for measuring PDE3A/PDE3B, SLFN12 and/or CREB3L1 levels.

In one embodiment, a kit of the invention comprises reagents for measuring, SLFN12 and/or CREB3L1 levels.

In one embodiment, a kit of the invention comprises a capture reagent that binds CREB3L1 polypeptide or polynucleotide and/or a capture reagent that binds SLFN12 polypeptide or polynucleotide.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of the invention.

EXAMPLES

Chemistry Experimental Methods

| | |
|---|---|
| [α] | specific rotation value |
| EtOH | Ethanol |
| THF | Tetrahydrofurane |
| DAD | Diode array detector |
| δ | NMR shift in ppm |
| d | doublet (NMR coupling pattern) |
| DMSO | dimethylsulfoxide |
| M | Molar or molecular Mass |
| ESI | electrospray ionisation (MS) |
| LiHMDS | Lithium 1,1,1,3,3,3-hexamethyldisilazan-2-ide |
| LC-MS | liquid chromatography coupled to mass spectrometry |
| m | multiplet (NMR coupling pattern) |
| MS | mass spectrometry |
| MHz | Megahertz |
| NMR | nuclear magnetic resonance |
| q | quartet (NMR coupling pattern) |
| $R_t$ | retention time |
| RT | room temperature |
| s | singlet (NMR coupling pattern) |
| t | triplet (NMR coupling pattern) |
| UPLC | Ultra Performance Liquid Chromatography |
| UV | ultraviolet |
| WL | wavelength |

LC-MS-Methods:
Method 1:
Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.
Method 2:
Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.
NMR-Data
The 1H-NMR data of selected compounds are listed in the form of 1H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: δ1 (intensity1), δ2 (intensity2), . . . , δi (intensityi), . . . , δn (intensityn).
The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A 1H-NMR peaklist is similar to a classical 1H-NMR readout, and thus usually contains all the peaks listed in a classical NMR interpretation. Moreover, similar to classical 1H-NMR printouts, peaklists can show solvent signals, signals derived from stereoisomers of the particular target compound, peaks of impurities, 13C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound 1 as required, optionally using additional intensity filters. Such an operation would be similar to peak-picking in classical 1H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

General Details

All reactions were carried out under nitrogen (N2) atmosphere. All reagents and solvents were purchased from commercial vendors and used as received. Nuclear magnetic resonance (NMR) spectra were recorded on a Bruker (300 or 400 MHz $^1$H, 75 or 101 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Flash chromatography was performed using 40-60 μm Silica Gel (60 Å mesh) on a Teledyne Isco Combiflash Rf. Tandem Liquid Chromatography/Mass Spectrometry (LC/MS) was performed on a Waters 2795 separations module and 3100 mass detector with a Waters Symmetry C18 column (3.5 μm, 4.6×100 mm) with a gradient of 0-100% CH3CN in water over 2.5 min with constant 0.1% formic acid. Analytical thin layer chromatography (TLC) was performed on EM Reagent 0.25 mm silica gel 60-F plates. Elemental analysis was performed by Robertson Microlit Laboratories, Ledgewood N.J.

Scheme 1: Synthesis of 6-[3,5-difluoro-4-(morpholin-4-yl)phenyl]-5-methyl-4,5-dihydropyridazin-3(2H)-one:

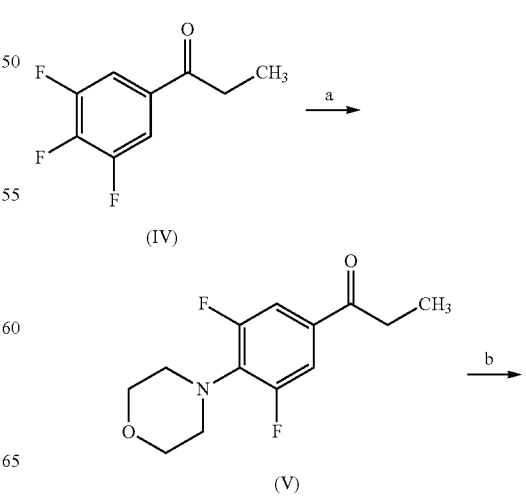

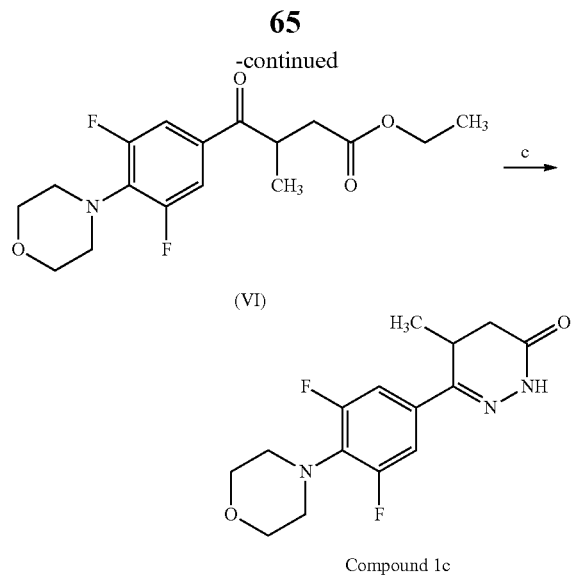

Compound 1c a) morpholine, N,N-diisopropylethylamine, CH₃CN, reflux; b) LiHMDS, THF, -78° C., then ethyl bromoacetate, THF, -78° C. to RT; c) hydrazine, EtOH, reflux.

Step a: 1-[3,5-difluoro-4-(morpholin-4-yl)phenyl]propan-1-one

A solution of 7.0 g of 1-(3,4,5-trifluorophenyl)propan-1-one (37 mmol), 32.5 mL of morpholine (372 mmol) and 13.2 mL of N,N-diisopropylethylamine (77.4 mmol) in 70 mL of CH₃CN was heated at reflux temperature overnight. The reaction was cooled and concentrated, water was added and rinsed with CH₂Cl₂. The CH₂Cl₂ was dried (MgSO₄) and concentrated. The crude product was dissolved in a mixture of CH₂Cl₂ and hexane. Rotary evaporation resulted in copious solid formation before concentration was complete and evaporation was halted. The solids were filtered and rinsed with hexanes yielding 6.06 g of product as an off-white solid which was clean by LC and NMR analysis. The mother liquors were concentrated and recrystallized from hexane yielding another 1.67 g of product as a yellow solid, the total yield was 7.73 g (81%). $^1$H NMR (300 MHz, CDCl₃) δ 7.46 (d, J=10.8 Hz, 2H), 3.89-3.75 (m, 4H), 3.41-3.24 (m, 4H), 2.90 (q, J=7.2 Hz, 2H), 1.21 (t, J=7.2 Hz, 3H). $^{19}$F NMR (376 MHz, CDCl₃) δ-119.79. Mass 256 (M+1).

Step b: ethyl 4-[3,5-difluoro-4-(morpholin-4-yl)phenyl]-3-methyl-4-oxobutanoate A 1.0 M solution of LiHMDS (28.8 mL, 28.8 mmol) in THF was added to 30 mL of THF and cooled with a dry ice/isopropanol bath. To this was slowly added a solution of 7.42 g of 1-[3,5-difluoro-4-(morpholin-4-yl)phenyl]propan-1-one (29.2 mmol) in 20 mL of THF via syringe. After stirring cold for 1 h, a solution of 3.85 mL (34.6 mmol) of ethyl bromoacetate in 10 mL of tetrahydrofuran was added slowly via syringe and the reaction mixture was allowed to warm to room temperature overnight. The next day the reaction was quenched with NH₄Cl$_{(aq)}$, EtOAc was added, separated and rinsed with brine. After drying and concentrating, the product was chromatographed with 0-10% EtOAc in hexane to yield 6.20 g (63%) of product as an oil. $^1$H NMR (400 MHz, CDCl₃) δ 7.51 (d, J=10.7 Hz, 2H), 4.11 (q, J=7.1 Hz, 2H), 3.81 (dd, J=16.8, 5.0 Hz, 5H), 3.33 (s, 4H), 2.96 (dd, J=16.9, 8.9 Hz, 1H), 2.45 (dd, J=16.9, 5.3 Hz, 1H), 1.27-1.18 (m, 6H). Mass 342 (M+1).

Step c: 6-[3,5-difluoro-4-(morpholin-4-yl)phenyl]-5-methyl-4,5-dihydropyridazin-3(2H)-one To a solution of 6.20 g of ethyl 4-[3,5-difluoro-4-(morpholin-4-yl)phenyl]-3-methyl-4-oxobutanoate in 100 mL EtOH was added 2.84 mL of hydrazine (90.5 mmol) and the reaction was heated at reflux temperature overnight. The next morning the solution was cooled to room temperature producing white crystals which were filtered and rinsed with EtOH yielding 1.8 g of clean product as determined by LC and NMR analysis. $^1$H NMR (400 MHz, CDCl₃) δ 8.84 (s, 1H), 7.28 (d, J=11.1 Hz, 2H), 3.91-3.79 (m, 4H), 3.30-3.26 (m, 4H), 3.26-3.20 (m, 1H), 2.72 (dd, J=17.0, 6.9 Hz, 1H), 2.50 (d, J=16.9 Hz, 1H), 1.25 (d, J=7.4 Hz, 3H). $^{19}$F NMR (376 MHz, CDCl₃) δ-119.69. Mass 310 (M+1). The mother liquors were concentrated by half and refluxed 6 h. Cooling produced crystals which were filtered and rinsed with EtOH yielding another 910 mg of product containing small amounts of impurities. Total yield 2.71 g (48%).

The enantiomers were separated by means of chiral super critical fluid chromatography: Column: ChiralPak AS-H, 250×4.6 mm, 5 um, Mobile Phase Modifier: 100% Methanol, Gradient: 5 to 50% Methanol over 10 minutes, Flow Rate: 4 mL/min, Back Pressure: 100 bar, Column Temperature: 40° C. UV detection was from 200-400 nm. The more active (R)-enantiomer (ret. time 7.08 min) was named Compound 1. Compound 1 was tested in the HeLa cell viability assay and its EC₅₀ was determined to be 1.1 nM. Compound 1 inhibited PDE3A with an IC₅₀ of 5 nM, and Compound 1 inhibited PDE3B with an IC₅₀ of 12 nM.

Scheme 2: Synthesis of (5R)-6-[3,5-difluoro-4-(morpholin-4-yl)phenyl]-5-methyl-4,5-dihydropyridazin-3(2H)-one and (5S)-6-[3,5-difluoro-4-(morpholin-4-yl)phenyl]-5-methyl-4,5-dihydropyridazin-3(2H)-one:

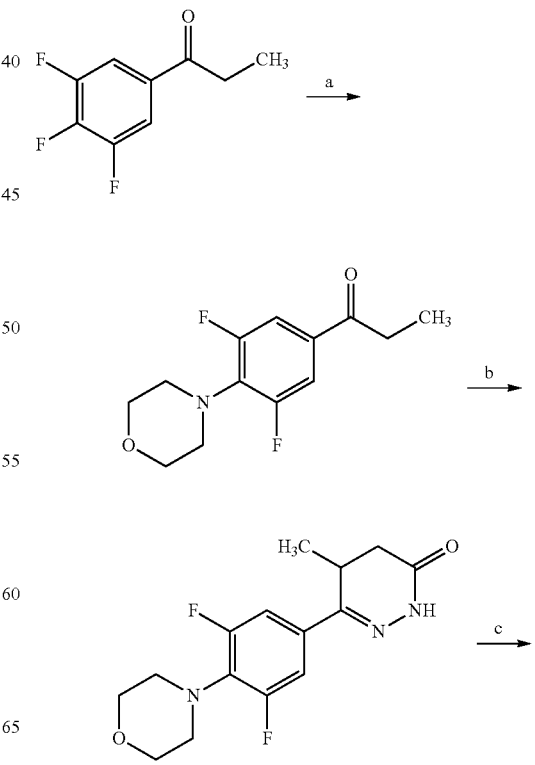

-continued

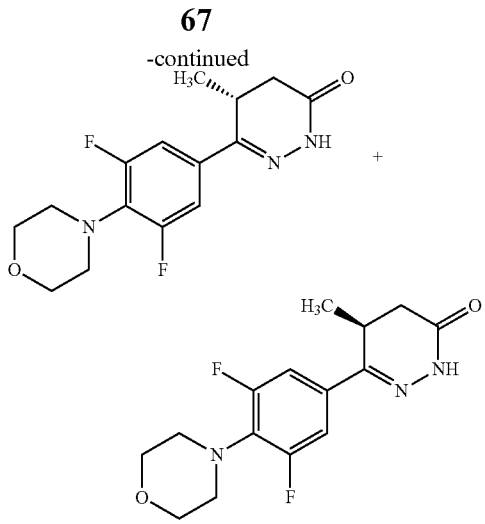

a) morpholine, N,N-diisopropylethylamine, CH₃CN, reflux; b) LiHMDS, THF, -78° C., then ethyl bromoacetate, THF, -78° C. to RT; then hydrazine hydrate, EtOH, reflux; c) separation of enantiomers.

Step a: 1-[3,5-difluoro-4-(morpholin-4-yl)phenyl]propan-1-one. Two parallel reactions were conducted in the following way: In a nitrogen atmosphere 1-(3,4,5-trifluorophenyl)propan-1-one (110 ml, 740 mmol) was dissolved in acetonitrile (1.4 l, 27 mol). Morpholine (490 ml, 5.6 mol) and N,N-diisopropylethylamine (200 ml, 1.1 mol) were added and the mixture stirred for 4h at 100° C. The solvents were removed and the crude products of two such reactions were combined. Dichloromethane (1000 mL) was added and washed five times with H₂O (400 mL), and saturated aqueous sodium chloride solution (300 mL). The organic phase was dried with Magnesium sulfate, filtered and dried in vacuo to afford the title compound (383.29 g, 100% of theory) in a purity of 90%. $^1$H-NMR (400 MHz, DMSO-d6) δ[ppm] 1.03 (t, J=7.22 Hz, 3H) 2.72 (q, J=7.18 Hz, 2H) 3.14 (m, 4H) 3.58-3.67 (m, 4H) 7.19-7.34 (m, 2H).

Step b: 6-[3,5-difluoro-4-(morpholin-4-yl)phenyl]-5-methyl-4,5-dihydropyridazin-3(2H)-one. Lithium 1,1,1,3,3,3-hexamethyldisilazan-2-ide (510 ml, 1.0 M in THF, 510 mmol) was added to THF (560 mL) and cooled to −78° C., then 1-[3,5-difluoro-4-(morpholin-4-yl)phenyl]propan-1-one (128 g, 501 mmol), dissolved in THF (850 mL), was added slowly. The reaction was stirred for 1 h at −70° C. Ethyl bromoacetate (67 ml, 600 mmol), dissolved in THF (110 mL), was added slowly. The mixture was stirred for 30 min at −70° C. The cooling bath was removed and the mixture stirred for 16h. Aqueous ammonium chloride solution (100 mL) and ethyl acetate (100 mL) were added. The aqueous phase was extracted two times with ethyl acetate (500 mL). All collected organic phases were dried with saturated aqueous sodium chloride solution (500 mL) and over magnesium sulfate, filtered and dried in vacuo. Crude ethyl 4-[3,5-difluoro-4-(morpholin-4-yl)phenyl]-3-methyl-4-oxobutanoate (181 g, 530.6 mmol, quant.) was obtained and 50 g were directly subjected to the next reaction. Thus, in a nitrogen atmosphere crude ethyl 4-[3,5-difluoro-4-(morpholin-4-yl)phenyl]-3-methyl-4-oxobutanoate (50.0 g, 146 mmol) was dissolved in ethanol (310 ml, 5.3 mol). Hydrazine hydrate (22 ml, 65% purity, 290 mmol) was added and the mixture was stirred for 16h under reflux. Water (1000 mL) was added and the organic phase was extracted three times with ethyl acetate (300 mL). The organic phases were washed with saturated aqueous sodium chloride solution, dried with sodium sulfate, filtered and further dried in vacuo. The crude product was purified by chromatography (silica, dichloromethane/ethyl acetate gradient) to afford the title compound (9.78 g, 22% of theory) in a purity of 95%. LC-MS (Method 2): Rt=0.96 min; MS (ESIpos): m/z=310 [M+H]⁺. $^1$H-NMR (400 MHz, DMSO-d6) δ[ppm]: 1.03 (d, J=7.35 Hz, 3H) 2.15-2.27 (m, 1H) 2.60-2.74 (m, 1H) 3.09-3.20 (m, 4H) 3.37 (m, 1H) 3.65-3.73 (m, 4H) 7.42 (d, J=11.66 Hz, 2H) 11.04 (s, 1H).

Step c: Separation of 6-[3,5-difluoro-4-(morpholin-4-yl)phenyl]-5-methyl-4,5-dihydropyridazin-3(2H)-one (8.0 g, 25.86 mmol) to (5R)-6-[3,5-difluoro-4-(morpholin-4-yl)phenyl]-5-methyl-4,5-dihydropyridazin-3(2H)-one (Compound 1) and (5S)-6-[3,5-difluoro-4-(morpholin-4-yl)phenyl]-5-methyl-4,5-dihydropyridazin-3(2H)-one (Compound 1a).

Instrument: Labomatic HD5000, Labocord-5000; Gilson GX-241, Labcol Vario 4000, column: YMC Amylose SA 5μ 250×50 mm; solvent A: dichlormethane; solvent B: Ethanol; Isocratic: 80% A+20% B; flow 100.0 ml/min; UV 325 nm.

(5R)-6-[3,5-difluoro-4-(morpholin-4-yl)phenyl]-5-methyl-4,5-dihydropyridazin-3(2H)-one. 3.77 g (95% purity, 45% yield). LC-MS (Method 1): Rt=0.99 min; MS (ESIpos): m/z=310 [M+H]⁺. $^1$H-NMR (500 MHz, DMSO-d6) δ[ppm]: 1.024 (15.88), 1.038 (16.00), 2.209 (3.09), 2.242 (3.49), 2.357 (0.46), 2.361 (0.65), 2.365 (0.48), 2.514 (2.20), 2.518 (1.98), 2.522 (1.56), 2.631 (0.54), 2.635 (0.75), 2.643 (2.60), 2.657 (2.91), 2.676 (2.45), 2.690 (2.28), 3.146 (6.85), 3.154 (9.80), 3.163 (7.30), 3.352 (1.66), 3.354 (1.66), 3.366 (2.32), 3.369 (2.28), 3.381 (1.56), 3.382 (1.47), 3.395 (0.40), 3.679 (11.05), 3.688 (11.70), 3.697 (10.24), 5.758 (1.59), 7.395 (0.53), 7.400 (1.00), 7.412 (7.35), 7.434 (7.49), 7.446 (0.94), 7.451 (0.61), 11.038 (8.10). [α]²⁰=−377.7° (DMSO) WL=589 nm.

(5S)-6-[3,5-difluoro-4-(morpholin-4-yl)phenyl]-5-methyl-4,5-dihydropyridazin-3 (2H)-one. 3.92 g (95% purity, 47% yield). LC-MS (Method 1): Rt=0.99 min; MS (ESIpos): m/z=310 [M+H]⁺. $^1$H-NMR (500 MHz, DMSO-d6) δ[ppm]: 1.024 (15.91), 1.038 (16.00), 2.209 (3.44), 2.242 (3.87), 2.361 (0.71), 2.518 (2.69), 2.522 (2.03), 2.635 (0.91), 2.643 (2.77), 2.657 (2.97), 2.676 (2.50), 2.690 (2.34), 3.154 (11.36), 3.352 (2.22), 3.366 (2.70), 3.381 (1.81), 3.394 (0.47), 3.679 (11.54), 3.688 (13.11), 3.697 (10.77), 5.758 (0.69), 7.395 (0.60), 7.400 (1.08), 7.412 (7.61), 7.434 (7.72), 7.445 (1.07), 7.451 (0.68), 11.038 (8.42). [α]²⁰=+356.9° (DMSO) WL=589 nm.

Scheme 3: Synthesis of 6-[3,5-difluoro-4-(morpholin-4-yl)phenyl]-5-methyl-4,5-dihydropyridazin-3(2H)-one:

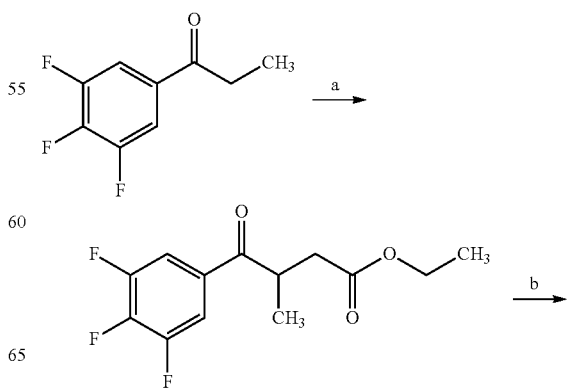

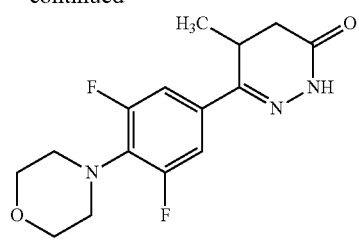

a) LiHMDS, THF, -78° C., then ethyl bromoacetate, THF, -70° C. to RT; b) morpholine, N,N-diisopropylethylamine, then hydrazine hydrate, 100° C.

Step a: Ethyl 3-methyl-4-oxo-4-(3,4,5-trifluorophenyl)butanoate

Lithium 1,1,1,3,3,3-hexamethyldisilazan-2-ide (12 ml, 1.0 M in THF, 12 mmol) was added to THF (10 mL) and cooled to −70° C., then 1-(3,4,5-trifluorophenyl)propan-1-one (1.7 ml, 12 mmol), dissolved in THF (8 mL), was added slowly. The reaction was stirred for 1.5 h at −70° C. Ethyl bromoacetate (1.6 ml, 14 mmol), dissolved in THF (3 mL), was added slowly. The mixture was stirred for 30 min at −70° C. The cooling bath was removed and the mixture stirred for 16h. The mixture was added to an aqueous hydrochloric acid solution (200 mL, 1M in H$_2$O) and extracted three times with dichloromethane. All collected organic phases were dried over magnesium sulfate, evaporated and dried in vacuo. Purification via column chromatography (silica gel, hexane/ethyl acetate, gradient) afforded the title compound (1.75 g, 46% of theory) in a purity of 85%. LC-MS (Method 1): Rt=0.1.31 min; MS (ESIpos): m/z=275.3 [M+H]$^+$.

Step b: 6-[3,5-difluoro-4-(morpholin-4-yl)phenyl]-5-methyl-4,5-dihydropyridazin-3(2H)-one To a solution of ethyl 3-methyl-4-oxo-4-(3,4,5-trifluorophenyl)butanoate (110 mg, 401 µmol) in N,N-diisopropylethylamine was added morpholine (70 µl, 800 µmol). The mixture was stirred at 100° C. for 16h. After cooling to RT, hydrazine hydrate (1:1) (240 µl, 80% purity, 4.0 mmol) was added and the mixture stirred for 3h at 100° C. Water was added slowly to the warm mixture and stirring was continued for 30 min. The precipitate was filtered, washed with water and dried in vacuo to afford the title compound (65 mg, 50% of theory) in a purity of 95%. LC-MS (Method 1): Rt=0.99 min; MS (ESIpos): m/z=310 [M+H]$^+$.

$^1$H-NMR (400 MHz, DMSO-d6) δ[ppm]: 1.022 (15.91), 1.040 (16.00), 2.205 (3.14), 2.245 (3.67), 2.322 (0.60), 2.326 (0.84), 2.332 (0.60), 2.518 (3.03), 2.522 (1.99), 2.637 (2.53), 2.655 (2.96), 2.664 (0.77), 2.668 (0.96), 2.673 (0.86), 2.679 (2.51), 2.697 (2.25), 3.143 (7.04), 3.154 (10.24), 3.166 (7.62), 3.348 (1.74), 3.351 (1.77), 3.366 (2.35), 3.370 (2.34), 3.384 (1.61), 3.403 (0.41), 3.677 (11.35), 3.689 (12.18), 3.700 (10.28), 7.388 (0.58), 7.395 (1.07), 7.409 (7.78), 7.438 (8.13), 7.452 (1.03), 7.459 (0.68), 11.038 (8.33).

Synthesis of Compound 2

6-[3,5-dichloro-4-(morpholin-4-yl)phenyl]-5-methyl-4,5-dihydropyridazin-3(2H)-one

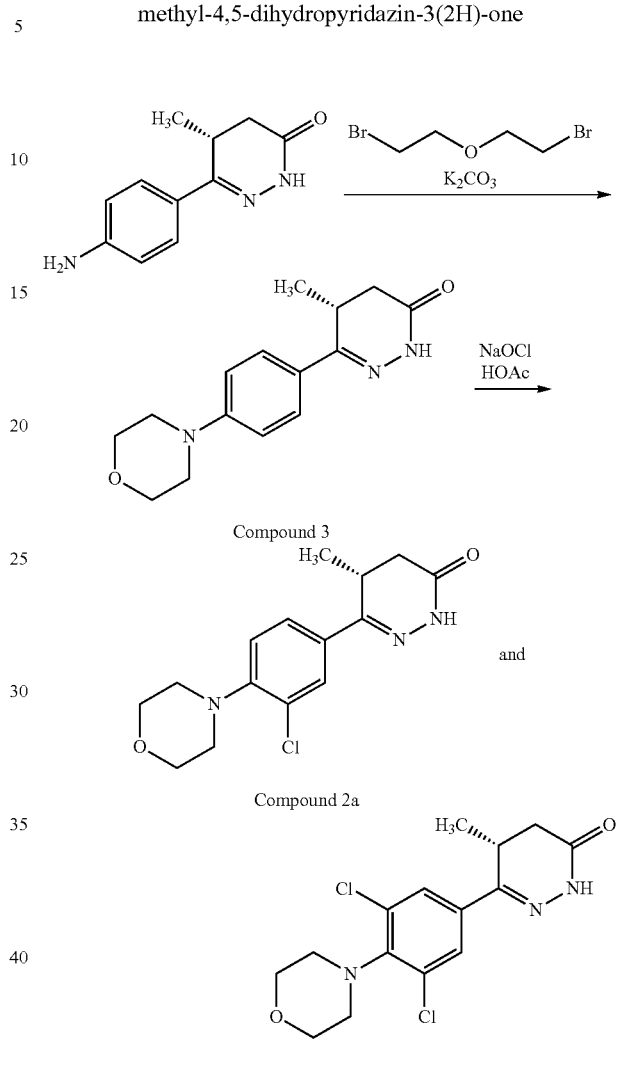

Compound 2
Step 1):

To 200 mg (0.984 mmol) of (R)-6-(4-aminophenyl)-5-methyl-4,5-dihydropyridazin-3(2H)-one dissolved in 1 mL of DMF was added 250 µL (2.00 mmol) of bis (2-bromoethyl) ether and 400 mg of K$_2$CO$_3$ and the mixture was stirred overnight at 60° C. The next day another 250 µL of bis (2-bromoethyl) ether and 170 mg of K$_2$CO$_3$ was added. After 3 h, EtOAc and water were added, the water was rinsed with EtOAc, the combined EtOAc washes were dried and concentrated. Chromatography with 0-4% MeOH in CH$_2$Cl$_2$ yielded 125 mg of product Compound 3 (46%). 1H NMR (300 MHz, CDCl$_3$) δ 8.61 (s, 1H), 7.68 (d, J=8.8, 2H), 6.92 (d, J=8.8, 2H), 3.99-3.76 (m, 4H), 3.44-3.31 (m, 1H), 3.29-3.22 (m, 4H), 2.70 (dd, J=6.7, 16.8, 1H), 2.46 (d, J=16.7, 1H), 1.24 (d, J=7.3, 3H). $^{13}$C NMR (75 MHz, CDCl$_3$) δ 166.64, 154.05, 152.18, 127.10, 125.33, 114.73, 66.69, 48.33, 33.93, 27.94, 16.36. MS: 274 (M+1). Anal. Calcd. for C$_{15}$H$_{19}$N$_3$O$_2$: C, 65.91; H, 7.01; N, 15.37; Found. 65.81, H, 6.66, N, 15.26.

Compound 2a and Compound 2
Step 2

A solution of 300 mg of compound 3 (1.10 mmol) dissolved in 5 mL of HOAc was stirred vigorously and cooled in a cold water bath ca. 10-15° C. such that no freezing occurred. To this was added a total of 2.2 mL of 10-15% NaOCl (aq) was added via syringe over ca. 30 min before LC indicated disappearance of Compound 3. The reaction was transferred to a separatory funnel, water was added and rinsed several times with $CH_2C_2$. The combined $CH_2C_2$ was rinsed with aqueous solutions of $NaHSO_3$ and $NaHCO_3$ before drying and chromatography with 0-60% EtOAc in hexane to isolate 140 mg of Compound 2 (35%, faster eluting product) and 135 mg (40%) of Compound 2a. Each product was recrystallized from MeOH.

Compound 2a: 1H NMR (400 MHz, $CDCl_3$) δ 8.58 (s, 1H), 7.80 (d, J=2.2 Hz, 1H), 7.60 (dd, J=8.2, 2.5 Hz, 1H), 7.04 (d, J=8.4 Hz, 1H), 4.02-3.76 (m, 4H), 3.38-3.22 (m, 1H), 3.23-3.02 (m, 4H), 2.70 (dd, J=17.0, 6.8 Hz, 1H), 2.48 (d, J=17.6 Hz, 1H), 1.24 (d, J=7.3 Hz, 3H). $^{13}C$ NMR (101 MHz, $CDCl_3$) δ 166.65, 152.50, 150.20, 130.02, 128.81, 128.39, 125.25, 119.96, 66.99, 51.40, 33.80, 27.92, 16.27. Mass 308 (M+1). Anal. Calc. for $C_{15}H_{18}ClN_3O_2$: C, 58.54; H, 5.89; N, 13.65. Found: C, 58.30; H, 5.99; N, 13.63.

Compound 2: $^1H$ NMR (400 MHz, $CDCl_3$) δ 8.95 (s, 1H), 7.67 (s, 2H), 3.90-3.75 (m, 4H), 3.35-3.17 (m, 5H), 2.70 (dd, J=17.0, 6.7 Hz, 1H), 2.49 (d, J=17.0 Hz, 1H), 1.24 (d, J=7.3 Hz, 3H). $^{13}C$ NMR (101 MHz, $CDCl_3$) δ 166.38, 151.17, 145.62, 134.83, 132.35, 126.65, 67.64, 49.97, 33.72, 27.85, 16.19. Mass 342 (M+1). Anal. Calcd. For $C_{15}H_{17}Cl_2N_3O_2$: C, 52.64; H, 5.01; N, 12.28. Found: C, 52.68; H, 4.90; N, 12.28.

Compound 2 was tested in the HeLa cell viability assay and its $EC_{50}$ was determined to be 1.9 nM. Compound 2 inhibited PDE3A with an $IC_{50}$ of 4 nM, and Compound 2 inhibited PDE3B with an $IC_{50}$ of 11 nM.

The Following Methods and Materials were Used or May be Used in Order to Obtain Data Supporting the Activity of Compounds 1 and 2:

Example 1

Cell Proliferation Measurement

The antiproliferative activity of the compounds of the general formula (I) was examined in vitro in human cancer cells. For this purpose, 1000 cells, including HuT78 cells, 500 HeLa cells, or 500 A2058 cells, were plated in 384-well plates with appropriate growth medium and incubated at 37° C. overnight. After 24 h, the cells on the test plate were treated with the compounds of the general formula (I) as and incubated at 37° C. for 72 h. The compounds were added to the cells by means of an HP D300 digital dispenser in a 10 (or more)—step dilution series. As control, the cells were treated with vehicle (DMSO at 0.3% final concentration). After 72 h, the cells were treated with 20 l/well of 50% CTG solution in PBS (Promega Cell Titer Glo (catalogue # G755B and G756B)) and incubated at room temperature for 10 min, and luminescence was measured by means of a VICTOR V (Perkin Elmer), in order to determine cell viability at the end of treatment. The percentage effect on cell growth and the $IC_{50}$ derived therefrom were determined for each test substance using the values from untreated wells (=percent viability). The $IC_{50}$ values were calculated using a 4-parameter fit.

TABLE 2

Cell proliferation results for Compound 1

| Cell line | Indication | IC50[M] |
|---|---|---|
| IGR37 | Melanoma | 2.19 E-9 |
| A549 | Lung adenocarcinoma | >6.00 E-7 (inactive) |
| SKMEL3 | Melanoma | 1.01 E-9 |
| HeLa | Cervical Cancer | 8.52 E-10 |

Thus another aspect of the invention is the use of Compound 1 and/or Compound 2, especially Compound 1 for the treatment of skin cancer, (e.g., melanoma), and cervical cancer.

Example 2

Compound Sensitivity Testing in Cell Lines

1000 HeLa (DMEM), cells were plated in a 384-well plate in 40 μl of corresponding growth media supplemented with 10% Fetal Bovine Serum. 24 hours after plating, indicated compounds were added at indicated concentrations and incubated for 48 hours. Cell viability was assessed as described in Compound library screening in NCI-H1734 and A549 cell lines. As shown in FIG. 1, Compounds 1 and 2 had similar dose response curves in HeLa cells. Compound 1 was tested in the HeLa cell viability assay and its EC50 was determined to be 1.1 nM. Compound 1 inhibited PDE3A with an IC50 of 5 nM, and Compound 1 inhibited PDE3B with an IC50 of 12 nM Compound 2 was tested in the HeLa cell viability assay and its EC50 was determined to be 1.9 nM. Compound 2 inhibited PDE3A with an IC50 of 4 nM, and Compound 2 inhibited PDE3B with an IC50 of 11 nM.

Figure 2:
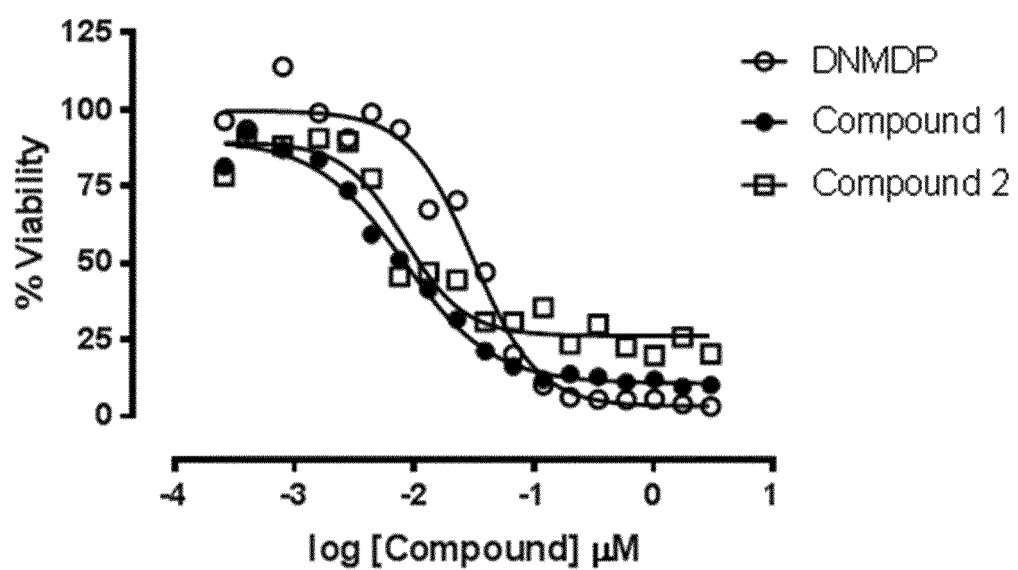
FIG. 2 provides the dose response curves for compound 1 and compound 2 in HuT78 cells, which lack PDE3A expression but express elevated levels of PDE3B and SLFN12.

FIG. 2 shows the dose response curves for compound 1 and compound 2 in HUT78 cells, which lack PDE3A expression, but express elevated levels of PDE3B and SLFN12.

Caspase Activity in HeLa Cells

1000 HeLa cells were plated in 384-well plate in 40 μl of corresponding growth media supplemented with 10% Fetal Bovine Serum. 24 hours after plating, indicated compounds are added at indicated concentrations and incubviabilityated for 48 hours. Caspase-Glo from Promega is added and luminescence read according to the manufacturers recommendations.

Correlation of Sensitivity Measurements with Basal Gene Expression

Gene-centric robust multichip average (RMA)-normalized basal mRNA gene expression data measured on the Affymetrix GeneChip Human Genome U133 Plus 2.0 Array are downloaded from the Cancer Cell Line Encyclopedia (CCLE, a detailed genetic characterization of a large panel of human cancer cell lines; Barretina et al., Nature 483, 603-607, 2012). Pearson correlation coefficients are calculated between gene expression (18,988 transcripts) and areas under the curve (AUCs) across 760 overlapping CCLs. For comparisons across small molecules exposed to differing numbers of CCLs, correlation coefficients are transformed using Fisher's transformation.

Example 3

Immunoblotting

Whole cell lysates were separated by standard SDS-PAGE. PDE3A protein was detected with anti-PDE3A A302-740A from Bethyl Laboratories. PDE3B protein was detected with anti-PDE3B A303-743A from Bethyl Laboratories.

Figure 3:
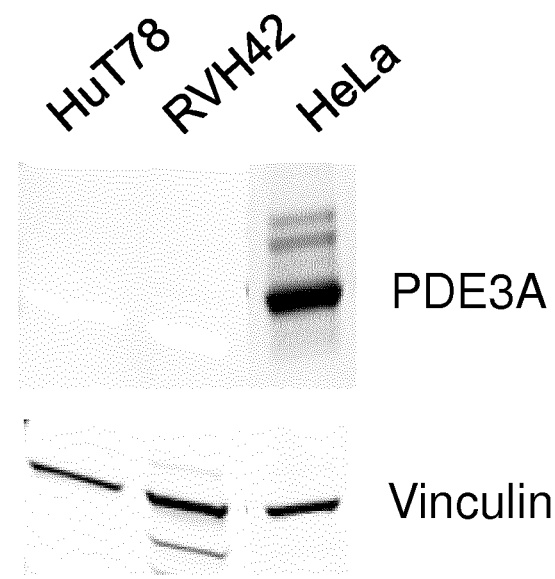
FIG. 3 is an immunoblot showing lack of endogenous PDE3A protein expression in the compound-sensitive cell lines HuT78 and RVH421, in contrast to high expression of PDE3A in HeLa cells. Vinculin is detected as a loading control.

FIG. 3 shows the immunoblot of endogenous PDE3A protein expression in HuT78, RVH42, and HeLa cell lines. As can be seen, HeLa cells have high expression of PDE3A as compared to HuT78 and RVH42 cells. Vinculin is detected in the immunoblots as a loading control.

Example 4

Method for PDE3A Enzyme Inhibition

The commercially available $^3$H-cAMP Scintillation Proximity Assay (SPA, Perkin Elmer) system was used for enzyme inhibition studies. For the determination of the in vitro effect of test substances on the PDE3A reactions 2 µl of the respective test compound solution in DMSO (serial dilutions) were placed in wells of microtiter plates (Isoplate-96/200W; Perkin Elmer). 50 µl of a dilution of PDE3A cell extract from Sf9 cells overexpressing human full length PDE3A (SB Drug Discovery, UK) in buffer A (50 mM Tris/HCl pH 7.5, 8.3 mM MgCl$_2$, 1.7 mM EDTA, 0.2% BSA) was added. The dilution of the PDE3A cell extract was chosen such that the reaction kinetics was linear and less than 70% of the substrate was consumed (typical dilution 1:5000). The reaction was started by addition of 50 µl (0.025 µCi) of 1:2000 in buffer A w/o BSA diluted substrate [8-$^3$H] adenosine 3', 5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). IC$_{50}$ values were determined from sigmoidal curves by plotting percentage PDE3A activity vs log compound concentration.

PDE3B Enzyme Inhibition

The commercially available $^3$H-cAMP Scintillation Proximity Assay (SPA, Perkin Elmer) system was used for enzyme inhibition studies. For the determination of the in vitro effect of test substances on the PDE3B reactions 2 µl of the respective test compound solution in DMSO (serial dilutions) were placed in wells of microtiter plates (Isoplate-96/200W; Perkin Elmer). 50 µl of a dilution of PDE3B cell extract from Sf9 cells overexpressing human full length PDE3B (SB Drug Discovery, UK) in buffer A (50 mM Tris/HCl pH 7.5, 8.3 mM MgCl$_2$, 1.7 mM EDTA, 0.2% BSA) was added. The dilution of the PDE3B cell extract was chosen such that the reaction kinetics was linear and less than 70% of the substrate was consumed (typical dilution 1:6000). The reaction was started by addition of 50 µl (0.025 µCi) of 1:2000 in buffer A w/o BSA diluted substrate [8-$^3$H] adenosine 3', 5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). IC$_{50}$ values were determined from sigmoidal curves by plotting percentage PDE3B activity vs log compound concentration.

For Compound 1, the IC50 values were 4.6 nM (PDE3A IC50) and 5.6 nM (PDE3B IC50) respectively.

Example 5

Method for Human Cryo Hepatocytes:

Investigation of In Vitro Metabolic Stability in Cryopreserved Human Hepatocytes (Including Calculation of Hepatic In Vivo Blood Clearance (CL) and Maximal Oral Bioavailability (Fmax))

Cryopreserved Hepatocytes (e.g. purchased from Celsis InVitroTechnologies) were briefly thawed, washed with 45 mL pre-warmed in in vitro GRO HT medium and centrifuged for 5 min at 50×g. The cell pellet was resuspended in 5 ml of Krebs-Henseleit Butter (KHB). Cell viability was determined by trypan blue exclusion.

For the metabolic stability assay liver cells were distributed in WME containing 5% FCS to glass vials at a density of 1.0×106 vital cells/ml. The test compound was added to a final concentration of 1 µM. During incubation, the hepatocyte suspensions were continuously shaken at 580 rpm and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1290 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability (Fmax) was calculated. The hepatic in vivo blood clearance (CLblood) and the maximal oral bioavailability (Fmax) was calculated using the following formulae: CL'intrinsic [ml/(min*kg)]=kel [1/min]/((cellno/volume of incubation [ml])*fu,inc)*(cellno/liver weight [g])*(specific liver weight [g liver/kg body weight]); CLblood well-stirred [L/(h*kg)]=(QH [L/(h*kg)]*fu, blood*CL'intrinsic [L/(h*kg)])/(QH [L/(h*kg)]+fu, blood*CL'intrinsic [L/(h*kg)]); Fmax=1-CLblood/QH and using the following parameter values: Liver blood flow—1.32 L/h/kg human; specific liver weight—21 g/kg body weight; liver cells in vivo—1.1×10$^8$ cells/g liver, liver cells in vitro—1.0×10$^6$/ml.; fu,inc and fu,blood is taken as 1.

(5R)-6-[3,5-difluoro-4-(morpholin-4-yl)phenyl]-5-methyl-4,5-dihydropyridazin-3 (2H)-one displays increased stability in human Hepatocytes (mean metabolic stability (Fmax)=66%) in comparison to (5R)-6-[3-fluoro-4-(morpholin-4-yl)phenyl]-5-methyl-4,5-dihydropyridazin-3(2H)-one (mean metabolic stability (Fmax)=49%).

Example 6

In Vivo Pharmacokinetics in Non-Rodents (e.g. Dogs)

For in vivo pharmacokinetic experiments test compounds were administered to non-rodents (e.g. female Beagle dogs) intravenously at doses of 0.1 to 1 mg/kg and intragastral at doses of 0.3 to 3 mg/kg formulated as solutions using solubilizers such as PEG400 in well-tolerated amounts and are usually given as short term infusion (15 min).

Blood samples were taken e.g. at 2 min, 8 min, 15 min, 30 min, 45 min, 1 h, 2 h, 4 h, 6 h, 8 h and 24 h after dosing from the vena saphena. Depending on the expected half-life additional samples were taken at later time points (e.g. 48 h, 72 h).

For pharmacokinetics after intragastral administration test compounds were given intragastral to fasted non-rodents (e.g. dogs). Blood samples were taken e.g. at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparin tubes (Monovetten®, Sarstedt) and centrifuged for 15 min at 3000 rpm. A small aliquot (e.g. 100 µL) from the supernatant (plasma) was taken and precipitated by addition of an aliquot ice cold acetonitril (e.g. of 400 µL) and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (abbreviation: CLp;) in L/kg/h) with Cp/Cb being the ratio of concentrations in plasma and blood.

PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0h to infinity (extrapolated) divided by the administered dose (in kg*h/L); AUC(0-tlast) norm: Area under the concentration-time curve from t=0h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

(5R)-6-[3,5-difluoro-4-(morpholin-4-yl)phenyl]-5-methyl-4,5-dihydropyridazin-3 (2H)-one displays reduced clearance in dogs (CLp=0.77 L/h/kg) in comparison to (5R)-6-[3-fluoro-4-(morpholin-4-yl)phenyl]-5-methyl-4,5-dihydropyridazin-3(2H)-one (CLp=1.7 L/h/kg).

Targeting PDE3A Locus Using CRISPR

CRISPR target sites were identified using the MIT CRISPR Design Tool (online MIT CRISPR design portal). For cloning of sgRNAs, forward and reverse oligonucleotides (oligos) were annealed, phosphorylated and ligated into BsmBI-digested pXPR_BRD001. Oligo sequences are as follows:

| sgRNA | Forward oligo | Reverse oligo |
|---|---|---|
| PDE3A_sg2 | CACCGAGACAAGCTTGCTA TTCCAA (SEQ ID NO.: 9) | AAACTTGGAATAGCAAGCT TGTCTC (SEQ ID NO.: 10) |

To produce lentivirus, 293T cells were co-transfected with pXPR_BRD001, psPAX2 and pMD2.G using calcium phosphate. Infected A2058 and HeLa cells were selected with 2 µg/ml of puromycin.

Figure 4:
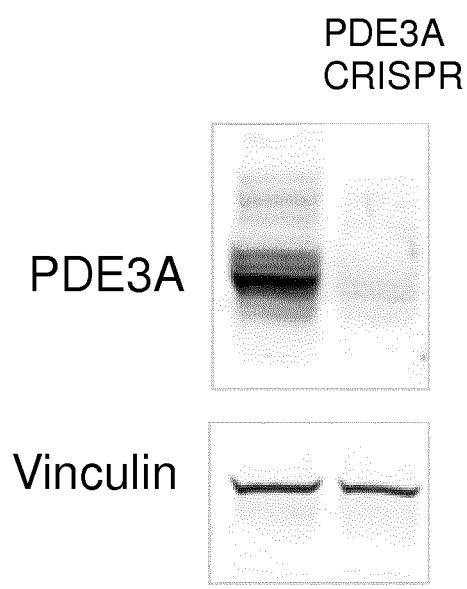
FIG. 4 is an immunoblot showing loss of expression of PDE3A in the PDE3A-CRISPR A2058 cells. Vinculin is detected as a loading control.
Figure 5:
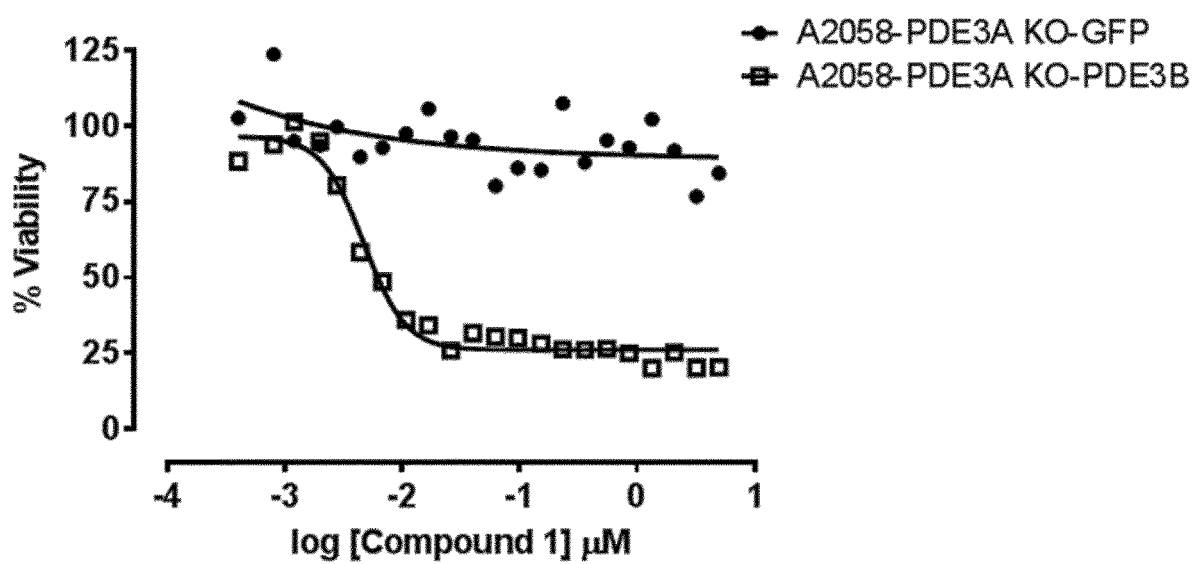
FIG. 5 shows the dose response curve for compound 1 in sensitive cell line A2058 made resistant by CRISPR knock-out of endogenous PDE3A. Whereas ectopic expression of GFP had no effect on lack of response to Compound 1, ectopic expression of PDE3B re-sensitized the A2058 cells lacking PDE3A to Compound 1 cytotoxic effects.

FIG. 4 shows the immunoblot of the sensitive A2058 cell line with and without CRISPR knockout of PDE3A. Immunoblotting with anti-PDE3A shows greatly decreased expression of PDE3A protein in PDE3A-CRISPR A2058 cells. As can be seen in the dose response curve shown in FIG. 5, the ectopic expression of PDE3B restores sensitivity to compound 1 in cells with little or no PDE3A expression.

Table 1 shows PDE3A, PDE3B, and SLFN12 RNA expression values for sensitive cell line A2058, expressing elevated PDE3A; sensitive cell line HuT78, expressing little PDE3A but elevated levels of PDE3B; and insensitive cell line A549, which expresses only low levels of SLFN12. As can be seen, both PDE3A and SLFN12 are elevated in cell line A2058 which showed sensitivity to the compound. Moreover, insensitive cell line A549 expresses only moderate levels of PDE3A and almost no SLFN12. Sensitive cell line HUT78 has elevated SLFN12 expression, but not have elevated PDE3A expression. Instead, cell line HUT78 has elevated SLFN12 expression and PDE3B expression.

TABLE 1

| Cell Line | PDE3A_ log2 (RPKM+1) | PDE3B_ log2 (RPKM+1) | SLFN12_ log2 (RPKM+1) | Compound Sensitivity |
|---|---|---|---|---|
| A2058 | 4.64 | 1.32 | 2.02 | sensitive |
| A549 | 2.61 | 0.85 | 0.06 | not sensitive |
| HUT78 | 0.08 | 3.84 | 5.48 | sensitive |

Example 7

In Vivo Xenotransplantation Models

The anti-tumor activity of Compound 1 was examined in murine xenotransplantation models of human cancer. For this purpose, mice were implanted subcutaneously with tumor cells. At a mean tumor size of 20-40 mm$^2$ animals were randomized into treatment and control groups (at least n=10 animals/group) and treatment started with vehicle only or Compound 1 (formulation: 90% PEG400/10% Ethanol; application route: per os ("p.o."), orally). The oral application volume was 10 ml/kg. In the case of twice daily treatments, the time interval between two applications per day was 6-7h. The tumor size and the body weight were determined at least weekly. The tumor area was detected by means of an electronic caliper [length (mm)×width (mm)]. The experiment was ended when the tumors of the vehicle control reached the pre-determined ethical endpoint based on German and European animal welfare regulations. In vivo anti-tumor efficacy is presented as T/C ratio at study end (Treatment/Control; mean tumor area or weight of treatment group/mean tumor area or weight of control group) in Table 7. A compound having a T/C below 0.5 is defined as active (i.e., effective). Statistical analysis was assessed using SigmaStat software. A one-way analysis of variance was performed and differences to the control were compared by a pair-wise comparison procedure (Dunn's method).

Results (Table 7):

Compound 1 showed potent anti-tumor efficacy in different xenograft models of human tumors upon monotherapy treatment. Specifically, Compound 1 was effective in reduction of tumor area in cervical cancer and melanoma.

TABLE 7

Anti-tumor activity of Compound 1 in different human cancer xenograft models in mice.

| Xenograft Model | Indication | Dose and schedule | T/C |
|---|---|---|---|
| HeLa | Cervical cancer | 10 mg/kg 2QD p.o. | 0.01a)* |
| IGR-37 | Melanoma | 40 mg/kg 2QD p.o. | 0.11b)* |
| SK-MEL3 | Melanoma | 40 mg/kg 2QD p.o. | 0.05b)* |
| A2058 | Melanoma | 40 mg/kg 2QD p.o. | 0.07b)* |

*P < 0.05 treatment vs control at study end
a)T/C = ratio of the mean tumor area of treatment versus mean tumor area of control group.
b)T/C = ratio of mean final tumor weight of treatment group versus mean final tumor weight of control group
The abbreviation 2QD means twice per day, p.o. means per os or-oral.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents and publications mentioned in this specification are herein incorporated by reference to the same extent as if each independent patent and publication was specifically and individually indicated to be incorporated by reference.

---

What is claimed is:

1. A compound having the structure:

Compound 1

Compound 2 or a pharmaceutically acceptable salt, or prodrug thereof.

2. A pharmaceutical composition containing a compound of claim 1 or a pharmaceutically acceptable salt, or prodrug thereof, and one or more pharmaceutically acceptable carriers or excipients.

3. A method of killing or reducing the survival of a cancer cell selected as responsive to a phosphodiesterase 3A (PDE3A) and/or (PDE3B) modulator involving contacting the cell with a compound of claim 1 where the cell was selected as having an increase in the level of a PDE3A and/or PDE3B or Schlafen 12 (SLFN12) polypeptide or polynucleotide, or combination thereof, relative to a reference, thereby reducing the survival of the cancer cell.

4. A method of reducing cancer cell proliferation in a subject pre-selected as having a cancer that is responsive to one or more PDE3A and/or PDE3B modulators comprising administering to the subject a compound of claim 1, where the subject is pre-selected by detecting an increase in the level of a PDE3A and/or PDE3B and Schlafen 12 (SLFN12) polypeptide or polynucleotide, or combination thereof, in a cell from the subject's cancer relative to a reference, thereby reducing cancer cell proliferation in said subject.

5. A method for treating a hyperproliferative disease responsive to a PDE3A and/or PDE3B modulator in a subject in need thereof comprising administering a compound of claim 1; or a pharmaceutically acceptable salt, or prodrug thereof to the subject.

6. The method according to claim 5 where the hyperproliferative disease is cancer.

7. The method according to claim 6 wherein said cancer is a bone, breast, cervical, colon, endometrium, gastrointestinal stromal tumor (GIST), head and neck, hematopoietic, kidney, leiomyosarcoma, liver, lung, lymphoid, melanoma, ovarian, pancreas, prostate, soft-tissue sarcoma, thyroid cancer, or urinary tract cancer.

8. The composition according to claim 2 wherein the compound is

9. The method of claim 3, further comprising detecting a lack of decrease in the level of expression of CREB3L1 polypeptide or polynucleotide relative to a reference and/or a decrease in the level of SLFN12.

10. The method according to claim 3, wherein the compound is

11. A kit for decreasing cancer cell proliferation in a subject pre-selected as having a cancer that is responsive to a PDE3A/PDE3B modulator containing one of the compounds of claim 1;

or a pharmaceutically acceptable salt, or prodrug thereof.

12. A method for the manufacture of a pharmaceutical composition for the treatment of cancer responsive to a PDE3A and/or PDE3B modulator, comprising mixing a PDE3A and/or PDE3B modulator with one or more pharmaceutically acceptable excipients, where the PDE3A and/or PDE3B modulator is a compound of claim 1;

or a pharmaceutically acceptable salt, or prodrug thereof.

13. The method of claim 12, wherein the cancer is a bone, breast, cervical, colon, endometrium, gastrointestinal stromal tumor (GIST), head and neck, hematopoietic, kidney, leiomyosarcoma, liver, lung, lymphoid, skin, melanoma, ovarian, pancreas, prostate, soft-tissue sarcoma, thyroid cancer, or urinary tract cancer.

14. The method of claim 13, wherein the cancer is melanoma or cervical cancer.

15. A method of preparing compound 1, said method comprising the steps of reacting a compound of formula (IV)

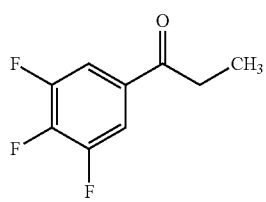

(IV)

with pure morpholine at elevated temperatures, or with morpholine and a base, optionally in a polar aprotic solvent, at reflux temperature, to obtain Compound (V)

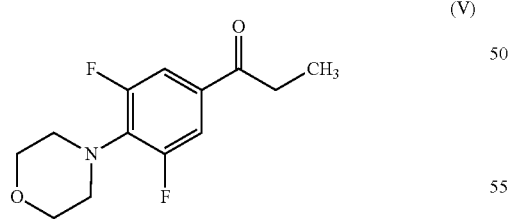

(V)

which then is reacted with a strong base, in a polar aprotic solvent at low temperatures followed by addition of ($C_1$-$C_4$-alkyl)bromoacetate or ($C_1$-$C_4$-alkyl)chloroacetate neat or in a polar aprotic solvent, allowing the mixture to warm up from initial −78° C. to RT, optionally isolating the crude product, and then adding either hydrazine or hydrazine hydrate in a polar protic organic solvent under reflux temperature to obtain the racemic compound 1c

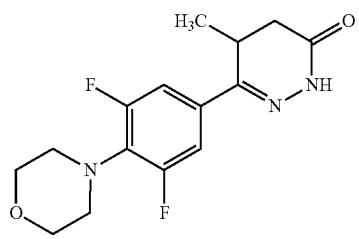

compound 1c and subsequently performing a separation of enantiomers of Compound 1c to obtain Compound 1 and Compound (1a)

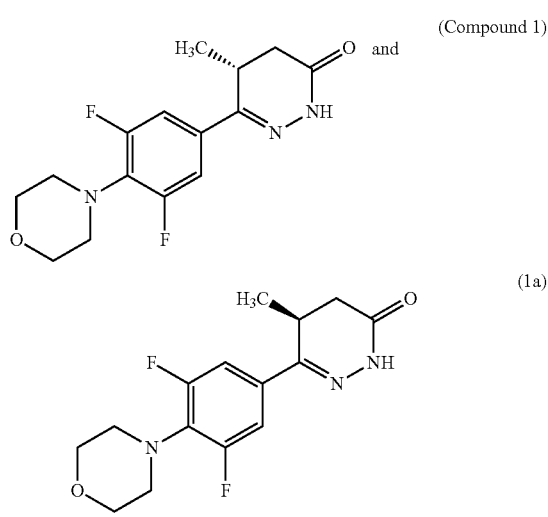

(Compound 1)

(1a)

whereby optionally compound (1a) is converted into the racemic compound (1c) which could then be separated again in order to obtain Compound 1 and less of the initial amount of compound 1a isolated from the enantiomeric separation.

16. A method for the preparation of Compound 1 whereby compound (IV)

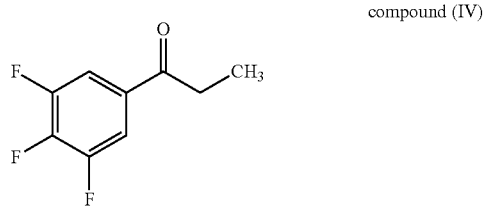

compound (IV)

is reacted with strong base in a polar aprotic solvent at low temperatures −78° to −60° C., followed by addition of ($C_1$-$C_4$-alkyl)bromoacetate or ($C_1$-$C_4$-alkyl)chloroacetate neat or in a polar aprotic solvent allowing the mixture to warm up from initial −78° C. to RT, optionally isolating the crude product, and then adding either hydrazine or hydrazine hydrate in a polar protic organic solvent under reflux temperature to produce compound (VII)

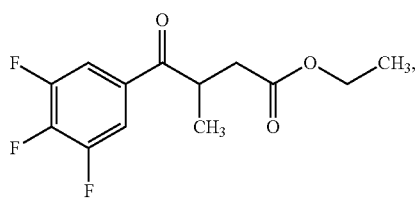 [SMILES: CCOC(=O)CC(C)C(=O)c1cc(F)c(F)c(F)c1]

(VII)

and further allowing compound (VII) to react with pure morpholine at elevated temperatures, or with morpholine and a base in a polar aprotic solvent at reflux temperature to obtain Compound 1c

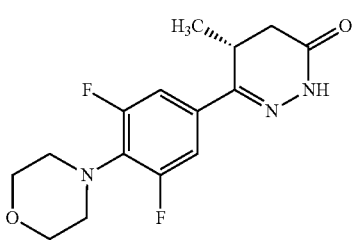

Compound 1c and subsequently performing a separation of enantiomers of Compound 1c to obtain Compound 1 and Compound (1a)

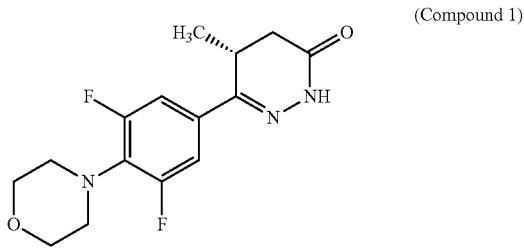

(Compound 1)

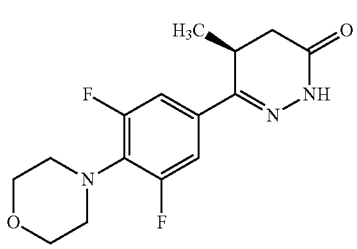

(1a)

whereby optionally compound 1a is converted into racemic material which could then be separated in order to obtain Compound 1 and less of the initial amount of compound 1a.

* * * * *